(12) United States Patent
Kapur et al.

(10) Patent No.: US 7,160,687 B1
(45) Date of Patent: Jan. 9, 2007

(54) MINIATURIZED CELL ARRAY METHODS AND APPARATUS FOR CELL-BASED SCREENING

(75) Inventors: Ravi Kapur, Gibsonia, PA (US); Kenneth Giuliano, Pittsburgh, PA (US)

(73) Assignee: Cellomics, Inc., Pittsburgh, PA (US)

( * ) Notice: Subject to any disclaimer, the term of this patent is extended or adjusted under 35 U.S.C. 154(b) by 857 days.

(21) Appl. No.: 09/624,131

(22) Filed: Jul. 21, 2000

Related U.S. Application Data

(63) Continuation-in-part of application No. 09/540,862, filed on Mar. 31, 2000, now Pat. No. 6,548,263, which is a continuation-in-part of application No. 09/401,212, filed on Sep. 22, 1999, now abandoned, which is a continuation-in-part of application No. 08/865,341, filed on May 29, 1997, now Pat. No. 6,103,479, application No. 09/624,131, which is a continuation-in-part of application No. 09/513,783, filed on Feb. 25, 2000, now Pat. No. 6,146,959.

(60) Provisional application No. 60/145,757, filed on Jul. 27, 1999.

(51) Int. Cl.
G01N 33/533 (2006.01)

(52) U.S. Cl. .............. 435/7.2; 435/7.1; 435/7.21; 435/29; 435/40.5; 435/40.51; 435/287.8; 435/287.9; 435/288.3; 435/288.4; 422/50; 422/57; 422/60; 422/63; 436/63; 436/164; 436/172; 436/518; 436/546; 436/800; 436/809; 356/300; 356/326

(58) Field of Classification Search ............... 435/7.1, 435/7.2, 7.21, 29, 40.5, 40.51, 288.3, 288.4, 435/287.8, 287.9; 422/50, 57, 60, 63; 436/546, 436/172, 800, 809, 63, 518, 164; 356/300, 356/326
See application file for complete search history.

(56) References Cited

U.S. PATENT DOCUMENTS

| 5,355,215 | A | | 10/1994 | Schroeder et al. |
|---|---|---|---|---|
| 5,436,128 | A | * | 7/1995 | Harpold et al. ............. 435/6 |
| 5,548,661 | A | | 8/1996 | Price et al. |
| 5,776,748 | A | | 7/1998 | Singhvi et al. |
| 5,790,710 | A | * | 8/1998 | Price et al. ............. 382/255 |
| 5,989,835 | A | | 11/1999 | Dunlay et al. |
| 6,103,479 | A | | 8/2000 | Taylor |

FOREIGN PATENT DOCUMENTS

| WO | WO 87/02802 | 5/1987 |
|---|---|---|
| WO | WO 94/11841 | 5/1994 |
| WO | WO 97/45730 | 12/1997 |
| WO | WO 98/28623 | 7/1998 |
| WO | WO 98/38490 | 9/1998 |
| WO | WO 98/45704 | 10/1998 |
| WO | WO 00/17624 | 3/2000 |
| WO | WO 00/50872 | 8/2000 |

OTHER PUBLICATIONS

Hendzel et al., Mitosis-specific phosphorylation of histone H3 intitates primarily within pericentromeric heterochromation durung G2 and spreads in a ordered fashion coincident with mitotic chromosome condensation. Chromosoma, 1997, 106:348-360.*
Taylor et al. The new vision of light microscopy. American Scientist, vol. 80, pp. 322-335.*
Taylor et al. Automated Interactive Microscopy: measuring and manipulating the chemical and molecular dynamics of cells and tissues. SPIE vol. 2678, pp. 15-27.*
Giuliano et al, (1998), *Trends in Biotech.*, 16:135-140.
Giuliano et al., (1987), *Anal. Biochem.*, 167:362-371.
Giuliano et al., (1990), *Optical Microscopy for Biology*, 543-557.
Giuliano et al., (1995), *Annu. Rev. of Biophysics and Biomolecular Structure*, 24:405-434.
Giuliano et al., (1995), *Curr. Op. Cell Biol.*, 7:4-12.
Giuliano et al., (1995), *Methods in Neuroscience*, 27:1-16.
Giuliano, (1996), *Cell Motil. Cytoskel.*, 35:237-253.
Takayama et al, (1999), *Proc. Natl. Acad. Sci.*. 96:5545-5548.
Taylor et al., (1992), *American Scientist*, 80:322-335.
Taylor et al., (1994), *Toxicologic Pathology*, 22:145-159.
Taylor et al., (1996), *Int. Soc. for Optical Engineering*, 2678: 15-27.
U.S. Appl. No. 60/018,696, filed May 30, 1996, D. Lansing Taylor.
Waggoner, et al., (1996) Human Pathology, vol.: 27(5), pp. 494-502.
Benveniste, et al., (1989), The Journal of Cell Biology, vol.: 109, pp. 2105-2115.
Carey, et al., (1996), The Journal of Cell Biology, vol.: 133(5), pp. 985-996.
Kolega, et al., (1993), Bioimaging, vol.: 1, pp. 136-150.
Farkas, et al., (1993), Annu. Rev. Physiol., vol.: 55, pp. 785-817.
Böcker, et al., (1996), Phys. Med. Biol., vol.: 41, pp. 523-537.
Pepperkok, et al., (1993), Experimental Cell Research, vol.: 204, pp. 278-285.
Article on Business Wire Website (May 28, 1996), ArrayScan System Introduces High Throughput Cell-Based Screening, Biological Detection, Inc., 1 page.
Article on Business Wire Website (Jun. 3, 1996), New Chain of Scientific Advisory Committee Brings Fluorescence Expertise, The Board of Directors of Biological Detection, Inc., 1 page.
Article on Business Wire Website (Sep. 25, 1996), Biological Detection, Inc. and Carl Zeiss Yena, GmbJ of Germany form worldwide strategic alliance in drug discovery, 1 page.
Article on BioCentury Archives, (Sep. 30, 1996), Biological Detection, Inc. and Carl Zeiss, Drug Discovery, 1 page.
Articles on Business Wire Website (Oct. 15, 1996), Biological Detection, Inc. Changes name to BioDx, Inc., 1 page.
Hanakam, et al., (1996), The EMBO Journal, vol.: 15(2), pp. 2935-2943.

(Continued)

*Primary Examiner*—Long V. Le
*Assistant Examiner*—Lisa V. Daniels-Cook
(74) *Attorney, Agent, or Firm*—McDonnell Boehnen Hulbert & Berghoff LLP

(57) ABSTRACT

The present invention describes methods and cassettes for cell-based toxin detection and organ localization. The cassettes includes an array containing cells and a matrix of openings or depressions, wherein each region of the substrate enclosed by the opening or depression in the matrix forms a domain individually addressable by microfluidic channels in the device.

7 Claims, 52 Drawing Sheets

OTHER PUBLICATIONS

Cole, et al., (1996), Molecular Biology of the Cell, vol.: 7, pp. 631-650.
Machiels, et al., (1996), European Journal of Cell Biology, vol.: 70, pp. 250-259.
Yasuhara, et al., (1997), Genes to Cells, vol.: 2, pp. 55-64.
Article on Business Wire Website, (Oct. 8, 1996), BDI appoints VP of Business Development form Beckman Instruments, Biological Detection, Inc., 1 page.
Mark V. Rogers, (1997), DDT, vol.: 2(4), pp. 156-160.
Giuliano, et al., (1997), Journal of Biomolecular Screening, vol.: 2(4), pp. 249-259.
Böcker, et al., (1995), Cytometry, vol.: 19, pp. 283-294.
Article on BioDx, Inc. Website, (1996), What's new at BioDx, 11 pages.
Article on Business Wire Website, (Jun. 3, 1996), New chair of Scientific Advisory Committee brings Fluorescence expertise, 1 page.
Article on Business Wire Website, (Sep. 25, 1996), Biological Detection, Inc. and Carl Zeiss Yena, GmbH of Germany form worldwide strategic alliance in drug discovery, 1 page.
Article on BioCentury Archives, (Sep. 30, 1996), 1 page.
Article on Business Wire Website, (Oct. 15, 1996), Biological Detection, Inc. changes Name to BioDx, Inc., 1 page.
Article on Business Wire Website, (Oct. 8, 1996), BDI appoints VP of Business Development from Beckman Instruments, 1 page.
Articles on BioDx Home Page, (1997), Solutions for Cell Screening, 25 pages.

* cited by examiner

Figure 3B

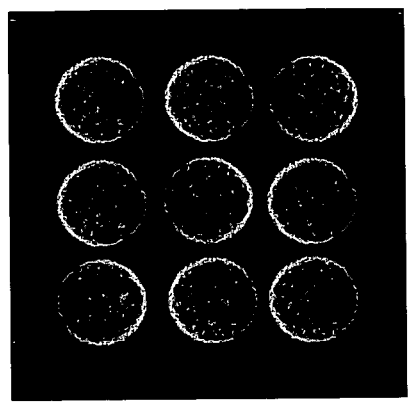

Sodium Fluorescein binding to Cell Chip to identify the location of 200 um spot patterns.

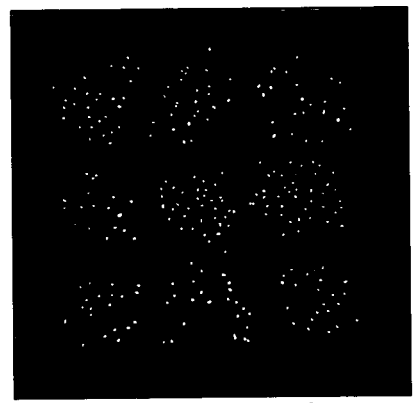

Fluorescent cell attachment of L929 cells to patterned spots (low magnification, 4x)

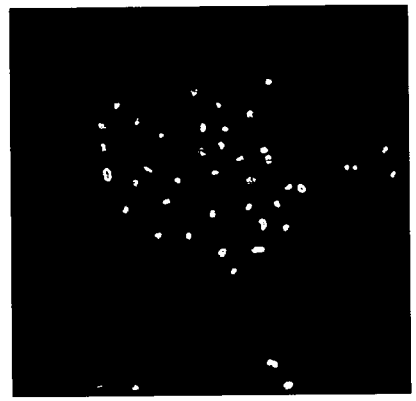

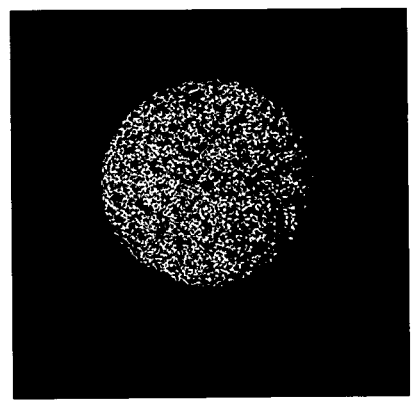

Sodium Fluorescein binding to Cell chip to identify the location of 400 um spots patterns.

Fluorescent cell attachment of 3T3 cells to patterned spots. Nuclei (above), Actin in same cells (below) (higher magnification, 20x)

A

B

A

B ized cell array methods and apparatus for cell-based screening

RELATED APPLICATIONS

This application claims priority to U.S. Provisional Patent Application Ser. Nos. 60/145,757 filed Jul. 27, 1999; is a continuation-in-part of U.S. patent application Ser. No. 09/540,862, filed Mar. 31, 2000, which is a continuation in part of U.S. patent application Ser. No. 09/401,212 filed Sep. 22, 1999; which is a continuation in part of 08/865,341 filed May 29, 1997, now U.S. Pat. No. 6,103,479; and is a continuation in part of U.S. patent application Ser. No. 09/513,783 filed Feb. 25, 2000, now U.S. Pat. No. 6,416,959.

U.S. GOVERNMENT RIGHTS

This invention was made in part with support from the U.S. Government under Contract No. N00014-98-C-0326, awarded by the U.S. Office of Naval Research, an organization of the U.S. Department of Defense. The U.S. Government may have certain nonexclusive rights in this invention.

FIELD OF THE INVENTION

The present invention relates to methods and devices for cell-based high throughput and high biological content screening.

BACKGROUND OF THE INVENTION

In the expanding arena of drug discovery and combinatorial chemistry to generate candidate compounds, it would be very useful to be able to rapidly screen a large number of substances, via a high throughput screen, for their physiological impact on animals and humans. Before testing the efficacy of a "partially qualified" drug candidate on animals, the drug could first be screened for its biological activity and potential toxicity with living cells. The physiological response to the drug candidate could then be anticipated from the results of these cell screens.

Traditionally, "lead compounds" have moved quickly to extensive animal studies that are both time-consuming and costly. Furthermore, extensive drug testing in animals is becoming less culturally acceptable. Screening drug candidates according to their interaction with living cells, prior to animal studies, can reduce the number of animals required in subsequent drug screening processes by eliminating some drug candidates before going to animal trials. However, manipulation and analysis of drug-cell interactions using current methods does not allow for both high throughput and high biological content screening, due to the small number of cells and compounds that can be analyzed in a given period of time, the cumbersome methods required for compound delivery, and the large volumes of compounds required for testing.

High throughput screening of nucleic acids and polypeptides has been achieved using DNA chip technologies. In typical DNA analysis methods, DNA sequences of 10 to 14 nucleotides are attached in defined locations (or spots), up to tens of thousands in number, on a small glass plate. (U.S. Pat. No. 5,556,752, hereby incorporated by reference). This creates an array of spots of DNA on a given glass plate. The location of a spot in the array provides an address for later reference to each spot of DNA. The DNA sequences are then hybridized with complementary DNA sequences labeled with fluorescent molecules. Signals from each address on the array are detected when the fluorescent molecules attached to the hybridizing nucleic acid sequences fluoresce in the presence of light. These devices have been used to provide high throughput screening of DNA sequences in drug discovery efforts and in the human genome sequencing project. Similarly, protein sequences of varying amino acid lengths have been attached in discrete spots as an array on a glass plate. (U.S. Pat. No. 5,143,854, incorporated by reference herein).

The information provided by an array of either nucleic acids or amino acids bound to glass plates is limited according to their underlying "languages". For example, DNA sequences have a language of only four nucleic acids and proteins have a language of about 20 amino acids. In contrast, a living cell, which comprises a complex organization of biological components, has a vast "language" with a concomitant multitude of potential interactions with a variety of substances, such as DNA, RNA, cell surface proteins, intracellular proteins and the like. Because a typical target for drug action is with and within the cells of the body, cells themselves provide an extremely useful screening tool in drug discovery when combined with sensitive detection reagents. It thus would be most useful to have high throughput, high content screening devices to provide high content spatial information at the cellular and subcellular level as well as temporal information about changes in physiological, biochemical and molecular activities.

Microarrays of Cells

Methods have been described for making micro-arrays of a single cell type on a common substrate for other applications. One example of such methods is photochemical resist-photolithograpy (Mrksich and Whitesides, Ann. Rev. Biophys. Biomol. Struct. 25:55–78, 1996), in which a glass plate is uniformly coated with a photoresist and a photo mask is placed over the photoresist coating to define the "array" or pattern desired. Upon exposure to light, the photoresist in the unmasked areas is removed. The entire photolithographically defined surface is uniformly coated with a hydrophobic substance, such as an organosilane, that binds both to the areas of exposed glass and the areas covered with the photoresist. The photoresist is then stripped from the glass surface, exposing an array of spots of exposed glass. The glass plate then is washed with an organosilane having terminal hydrophilic groups or chemically reactable groups such as amino groups. The hydrophilic organosilane binds to the spots of exposed glass with the resulting glass plate having an array of hydrophilic or reactable spots (located in the areas of the original photoresist) across a hydrophobic surface. The array of spots of hydrophilic groups provides a substrate for non-specific and non-covalent binding of certain cells, including those of neuronal origin (Kleinfeld et al., J. Neurosci. 8:4098–4120, 1988).

In another method based on specific yet non-covalent interactions, stamping is used to produce a gold surface coated with protein adsorptive alkanethiol. (U.S. Pat. No. 5,776,748; Singhvi et al., Science 264:696–698, 1994). The bare gold surface is then coated with polyethylene-glycol-terminated alkanethiols that resist protein adsorption. After exposure of the entire surface to laminin, a cell-binding protein found in the extracellular matrix, living hepatocytes attach uniformly to, and grow upon, the laminin coated islands (Singhvi et al. 1994). An elaboration involving strong, but non-covalent, metal chelation has been used to coat gold surfaces with patterns of specific proteins (Sigal et al., Anal. Chem. 68:490–497, 1996). In this case, the gold surface is patterned with alkanethiols terminated with nitriloacetic acid. Bare regions of gold are coated with tri(ethyleneglycol) to reduce protein adsorption. After adding $Ni^{2+}$, the specific adsorption of five histidine-tagged proteins is found to be kinetically stable.

More specific single cell-type binding can be achieved by chemically crosslinking specific molecules, such as proteins, to reactable sites on the patterned substrate. (Aplin and Hughes, Analyt. Biochem. 113:144–148, 1981). Another elaboration of substrate patterning optically creates an array of reactable spots. A glass plate is washed with an organosilane that chemisorbs to the glass to coat the glass. The organosilane coating is irradiated by deep UV light through an optical mask that defines a pattern of an array. The irradiation cleaves the Si—C bond to form a reactive Si radical. Reaction with water causes the Si radicals to form polar silanol groups. The polar silanol groups constitute spots on the array and are further modified to couple other reactable molecules to the spots, as disclosed in U.S. Pat. No. 5,324,591, incorporated by reference herein. For example, a silane containing a biologically functional group such as a free amino moiety can be reacted with the silanol groups. The free amino groups can then be used as sites of covalent attachment for biomolecules such as proteins, nucleic acids, carbohydrates, and lipids. The non-patterned covalent attachment of a lectin, known to interact with the surface of cells, to a glass substrate through reactive amino groups has been demonstrated (Aplin & Hughes, 1981). The optical method of forming a micro-array of a single cell type on a support requires fewer steps and is faster than the photoresist method, (i.e., only two steps), but it requires the use of high intensity ultraviolet light from an expensive light source.

In all of these methods, the result is a micro-array of a single cell type, since the biochemically specific molecules are bound to the micro-patterned chemical array uniformly. In the photoresist method, cells bind to the array of hydrophilic spots and/or specific molecules attached to the spots which, in turn, bind cells. Thus cells bind to all spots in the array in the same manner. In the optical method, cells bind to the array of spots of free amino groups by adhesion. There is little or no differentiation between the spots of free amino groups. Again, cells adhere to all spots in the same manner, and thus only a single type of cell interaction can be studied with these cell arrays because each spot on the array is essentially the same as another. Such cell arrays are inflexible in their utility as tools for studying a specific variety of cells in a single sample or a specific variety of cell interactions. Thus, there exists a need for arrays of multiple cell types on a common substrate, in order to increase the number of cell types and specific cell interactions that can be analyzed simultaneously, as well as methods of producing these micro-arrays of multiple cell types on a common substrate, in order to provide for high throughput and high biological content screening of cells.

Optical Reading of Cell Physiology

Performing a high throughput screen on many thousands of compounds requires parallel handling and processing of many compounds and assay component reagents. Standard high throughput screens use homogeneous mixtures of compounds and biological reagents along with some indicator compound, loaded into arrays of wells in standard microplates with 96 or 384 wells. (Kahl et al., J. Biomol. Scr. 2:33–40, 1997). The signal measured from each well, either fluorescence emission, optical density, or radioactivity, integrates the signal from all the material in the well giving an overall population average of all the molecules in the well. This type of assay is commonly referred to as a homogeneous assay.

U.S. Pat. No. 5,581,487 describes an imaging plate reader that uses a CCD detector (charge-coupled optical detector) to image the whole area of a 96 well plate. The image is analyzed to calculate the total fluorescence per well for homogeneous assays.

Schroeder and Neagle describe a system that uses low angle laser scanning illumination and a mask to selectively excite fluorescence within approximately 200 microns of the bottoms of the wells in standard 96 well plates in order to reduce background when imaging cell monolayers. (J. Biomol. Scr. 1:75–80, 1996). This system uses a CCD camera to image the whole area of the plate bottom. Although this system measures signals originating from a cell monolayer at the bottom of the well, the signal measured is averaged over the area of the well and is therefore still considered a homogeneous measurement, since it is an average response of a population of cells. The image is analyzed to calculate the total fluorescence per well for cell-based homogeneous assays.

Proffitt et. al. (Cytometry 24:204–213, 1996) describe a semi-automated fluorescence digital imaging system for quantifying relative cell numbers in situ, where the cells have been pretreated with fluorescein diacetate (FDA). The system utilizes a variety of tissue culture plate formats, particularly 96-well microplates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures for a variety of tissue culture plate formats. Thresholding of digital images and the use of reagents that fluoresce only when taken up by living cells are used to reduce background fluorescence without removing excess fluorescent reagent.

A variety of methods have been developed to image fluorescent cells with a microscope and extract information about the spatial distribution and temporal changes occurring in these cells. A recent article describes many of these methods and their applications (Taylor et al., Am. Scientist 80:322–335, 1992). These methods have been designed and optimized for the preparation of small numbers of specimens for high spatial and temporal resolution imaging measurements of distribution, amount and biochemical environment of the fluorescent reporter molecules in the cells.

Treating cells with dyes and fluorescent reagents, imaging the cells, and engineering the cells to produce a fluorescent reporter molecule, such as modified green fluorescent protein (GFP), are useful detection methods (Wang et al., In Methods in Cell Biology, New York, Alan R. Liss, 29:1–12, 1989). The green fluorescent protein (GFP) of the jellyfish *Aequorea victoria* has an excitation maximum at 395 nm, an emission maximum at 510 nm and does not require an exogenous factor. Uses of GFP for the study of gene expression and protein localization are discussed in Chalfie et al., Science 263:802–805, 1994. Some properties of wild-type GFP are disclosed by Morise et al. (Biochemistry 13:2656–2662, 1974), and Ward et al. (Photochem. Photobiol. 31:611–615, 1980). An article by Rizzuto et al. (Nature 358:325–327, 1992) discusses the use of wild-type GFP as a tool for visualizing subcellular organelles in cells. Kaether and Gerdes (FEBS Letters 369:267–271, 1995) report the visualization of protein transport along the secretory pathway using wild-type GFP. The expression of GFP in plant cells is discussed by Hu and Cheng (FEBS Letters 369: 331–334, 1995), while GFP expression in *Drosophila* embryos is described by Davis et al. (Dev. Biology 170: 726–729, 1995). U.S. Pat. No. 5,491,084, incorporated by reference herein, discloses expression of GFP from *Aequorea victoria* in cells as a reporter molecule fused to another protein of interest. Mutants of GFP have been prepared and used in several biological systems. (Hasselhoff et al., Proc. Natl. Acad. Sci. 94:2122–2127, 1997; Brejc et al., Proc. Natl. Acad. Sci. 94:2306–2311, 1997; Cheng et al., Nature Biotech. 14:606–609, 1996; Heim and Tsien, Curr. Biol. 6:178–192, 1996; Ehrig et al., FEBS Letters 367:163–166, 1995).

The ARRAYSCAN™ System, as developed by Cellomics, Inc. (U.S. Pat. No. 5,989,835) and U.S. application Ser. No. 09/031,271 filed Feb. 27, 1998; both incorporated by reference herein in their entirety) is an optical system for determining the distribution, environment, or activity of luminescently labeled reporter molecules on or in cells for the purpose of screening large numbers of compounds for specific biological activity. The ARRAYSCAN™ System involves providing cells containing luminescent reporter molecules in an array of locations and scanning numerous cells in each location, converting the optical information into digital data, and utilizing the digital data to determine the distribution, environment or activity of the luminescently labeled reporter molecules in the cells. The ARRAYSCAN™ System includes apparatus and computerized method for processing, displaying and storing the data, thus augmenting drug discovery by providing high content cell-based screening, as well as combined high throughput and high content cell-based screening, in a large microplate format.

Microfluidics

Efficient delivery of solutions to an array of cells attached to a solid substrate is facilitated by a microfluidic system. Methods and apparatus have been described for the precise handling of small liquid samples for ink delivery (U.S. Pat. No. 5,233,369; U.S. Pat. No. 5,486,855; U.S. Pat. No. 5,502,467), biosample aspiration (U.S. Pat. No. 4,982,739), reagent storage and delivery (U.S. Pat. No. 5,031,797), and partitioned microelectronic and fluidic device array for clinical diagnostics and chemical synthesis (U.S. Pat. No. 5,585,069). In addition, methods and apparatus have been described for the formation of microchannels in solid substrates that can be used to direct small liquid samples along the surface (U.S. Pat. No. 5,571,410; U.S. Pat. No. 5,500,071; U.S. Pat. No. 4,344,816).

For purposes of integrated high throughput and high content cell based screening, particularly for live-cell imaging, an optimal microfluidic device would comprise a fluidic architecture that permits the closest possible well spacing (i.e.: highest possible well density), wherein the fluidic architecture is integrated with the cell array substrate to permit efficient fluid delivery to the cells, and eliminating the need for pipetting fluids in and out of wells. Such optimal microfluidic devices would be advantageous for cell arrays with sub-millimeter inter-well distances because it is unwieldy, if not impossible, to pipette fluids with such a high degree of spatial resolution and accuracy. Furthermore, such integrated devices could be directly used for cell based screening, without the need to remove the cell substrate from the fluidic architecture for imaging the cells.

An optimal microfluidic device for cell based screening might further comprise a closed chamber to permit environmental control of the cells, and preferably would not directly expose the cells to electro-kinetic forces, which may affect the physiology of the cells on the substrate. For example, electrohydrodynamic pumping is less effective with polar solvents (Marc Madou, Fundamentals of Microfabrication, CRC Press, Boca Raton, 1997, p. 433). Electro-osmosis is typically accompanied by some degree of electrophoretic separation of charged medium components, such as proteins.

U.S. Pat. No. 5,603,351 ('the 351 patent') describes a microfluidic device that uses a multilevel design consisting of two upper levels with channels and a bottom level with reaction wells. However, this device is not designed for use in cell based screening. The '351 patent does not disclose a substrate containing cells or cell binding sites. The disclosed microfluidic network is designed to allow two or more reagents to be combined in a reaction well, as opposed to an optimal cell screening microfluidic system that allows living cells cultured on the well bottoms to be exposed in serial fashion to two or more different fluids. The '351 patent discloses a device with the wells etched into the substrate at a maximal well density of 50 wells/inch$^2$. Furthermore, the substrate must be detached from the fluidic array for incubation and/or analysis. Finally, the '351 patent discloses a system of electrically-controlled electrohydrodynamic valves within the matrix of the wells that are less effective with aqueous media used in cell culture, and also may limit the degree of close-spacing between wells in the array of wells.

U.S. Pat. No. 5,655,560 discloses a clog-free valving system, comprising a fluid distribution system with multiple inputs and multiple outputs incorporating a crossed array of microchannels connected vertically at crossing points by teflon valves. However, this patent does not disclose a substrate containing a cell array, nor an integrated fluidic device in combination with the substrate, nor a well density that is optimal for cell-based screening.

U.S. Pat. No. 5,900,130 (the '130' patent) describes the active, electronic control of fluid movement in an interconnected capillary structure. This patent does not teach a fluidic architecture that maximizes the area of the cell substrate that can be occupied by cell binding sites. Nor does this patent disclose a substrate containing a cell array, nor an integrated fluidic device in combination with the substrate. Furthermore, the patent only teaches the control of fluid flow by application of an electric field to the device.

U.S. Pat. No. 5,910,287 describes multi-well plastic plates for fluorescence measurements of biological and biochemical samples, including cells, limited to plates with greater than 864 wells. This patent does not describe a microfluidic device with a fluidic architecture integrated with the cell array substrate. Nor does the patent disclose a closed chamber to permit environmental control of the cells on the substrate.

Thus, none of these prior microfluidic devices provide a fluidic architecture that permits the closest possible well spacing (i.e.: highest possible well density), wherein the fluidic architecture is integrated with the cell array substrate to permit efficient fluid delivery to the cells, and thus eliminating the need for pipetting fluids in and out of wells. Furthermore, prior microfluidic devices that comprise an array of wells use electrically-controlled electrohydrodynamic valves within the matrix of the wells that would be less effective if used with aqueous media for cell culture, and which limit the well density.

While the above advances in cell array, optical cell physiology reading, and microfluidic technologies provide supporting technologies that can be applied to improved high throughput and high content cell-based screening, there remains a need in the art for integrated devices and methods that further decrease the amount of time necessary for such screening, as well as for devices and methods that further improve the ability to conduct high throughput and high content cell-based screening and the ability to flexibly and rapidly switch from one to the other. In particular, devices and methods that maximize the well density, thereby increasing the number of wells that can be imaged in at one time, and thus greatly increasing the throughput of a screen while maintaining adequate resolution of the image, would be very advantageous.

The drug discovery industry already uses 96- and 384-well microplates and is in transition towards the use of 1536-well plates. However, further increases in well density using prior technology are unlikely because of the great difficulty of pipetting liquids in and out of very small diameter wells.

SUMMARY OF THE INVENTION

The present invention fulfills the need in the art for devices and methods that decrease the amount of time necessary to conduct cell-based screening, and specifically combines the ability to conduct high throughput and high content cell-based screening and to flexibly and rapidly switch from one to the other. The invention provides devices and methods for maximizing the number of wells that can be imaged at one time while still obtaining adequate pixel resolution in the image. This result has been achieved through the use of fluidic architectures that maximizes well density. The present invention thus provides a miniaturized microplate system with closed fluidic volumes that are internally supplied with fluid exchange, and with wells that are closely spaced to more rapidly detect spatially-resolved features of individual cells.

In one aspect, the present invention provides a cassette for cell screening, comprising a substrate having a surface containing a plurality of cell binding locations; a fluid delivery system for delivering reagents to the plurality of cell binding locations, wherein the fluid delivery system comprises a multi-level chamber that mates with the substrate, wherein the multi-level chamber comprises a crossed array of microfluidic input channels and output channels and a plurality of fluidic locations in fluid connection with the microfluidic input channels and output channels; and a plurality of wells, wherein an individual well comprises the space defined by the mating of one cell binding location and one fluidic location, and wherein the wells are present at a density of at least about 20 wells per square centimeter.

In another aspect, the present invention provides a cassette for cell screening comprising
 a. a substrate having a surface, wherein the surface contains a plurality of cell binding locations;
 b. a fluid delivery system for delivering reagents to the plurality of cell binding locations, wherein the fluid delivery system comprises a multi-level chamber that mates with the substrate, wherein the multi-level chamber comprises
  i. a crossed array of microfluidic input channels and output channels, wherein each well is in fluid connection with one or more input channels and one or more output channels;
  ii. a plurality of fluidic locations in fluid connection with the microfluidic input channels and output channels;
  iii. one or more input manifolds in fluid connection with the microfluidic input channels;
  iv. one or more output manifolds in fluid connection with the microfluidic output channels;
  v. at least one source receptacle in fluid connection with the one or more input manifolds; and
  vi. at least one waste receptacle in fluid connection with one or more output manifolds; and
 c. a plurality of wells, wherein an individual well comprises the space defined by the mating of one cell binding location and one fluidic location.

In preferred embodiments, both of the above cassettes further comprise a pump to control fluid flow within the microfluidic device; a temperature controller of the substrate and/or a controller to regulate oxygen and carbon dioxide partial pressures.

In another aspect, the present invention provides an improved method for diffusion control in a cassette, wherein the improvement comprises constantly applying a passive restoring force to valves located within microfluidic channels of the cassette.

In a still further aspect, the present invention provides a method for cell screening, comprising
 a) providing an array of locations which contain multiple cells;
 b) providing an optical system to obtain images of the array of locations;
 c) serially imaging sub-arrays of the array of locations; and
 d) acquiring data from each of the sub-arrays in parallel.

In a preferred embodiment, the array of locations is provided as a cassette, such as those disclosed above.

In a further aspect, the present invention provides novel methods for making a substrate for selective cell patterning, and the substrates themselves, wherein the method comprises contacting reactive hydroxyl groups on the surface of a substrate with a hydroxyl-reactive bifunctional molecule to form a monolayer, and using stencils to deposit cell repulsive or cell adhesive moieties to the substrate. In preferred embodiments the hydroxyl-reactive bifunctional molecule is an aminosilane and the cell repulsive moiety comprises tresyl-activated polyethylene glycol.

Among other uses, the devices and methods of the present invention are ideal for high content and/or high throughput cell-based screening. The device of the invention is also ideally suited as a cell support system for a hand-held diagnostic device (i.e.: a miniaturized imaging cell-based assay system). The smaller format and sealed containment of the present device enables its use in a rugged, portable system. There is a great economic advantage from the use of higher density plates. There is a further economic advantage in faster imaging of sub-arrays when using a high density plate; this advantage is not fully realized if the distances between adjacent wells are not minimized. The present invention provides both of these advantages.

The present invention further provides cassettes for cell screening, comprising a substrate having a surface; a fluid delivery system mated with the substrate, wherein the fluid delivery system comprises:
 1) a matrix of openings or depressions, wherein each region of the substrate enclosed by the opening or depression in the matrix comprises an individually addressable domain; and
 2) microfluidic channels that supply fluid to the domains.

In preferred embodiments, each domain comprises cell binding sites separated by cell repulsive regions and each domain comprises a single cell type expressing one or more biosensors, arrayed on the cell binding sites. In a more preferred embodiment, at least three different cell types are arrayed on the surface, and each of the three different cell types are specific for different tissue types.

The present invention further provides automated methods for cell based toxin detection and organ localization comprising providing an array of locations containing multiple cell types derived from different organ types and each of the cell types comprising at least one luminescent reporter molecule; wherein the localization, distribution, structure, or activity of the at least one luminescent reporter molecule is altered by a toxin to be detected; contacting the cells with a test substance and utilizing digital data derived from the reporter molecules to detect the presence of a toxin in the compound, and to characterize its biodistribution.

BRIEF DESCRIPTION OF THE FIGURES

FIG. 3B is a photograph showing fibroblastic cell growth in spotted patterns, attached to a micro-patterned chemical array and labeled with two fluorescent probes.

TABLE 1

Figure 1:
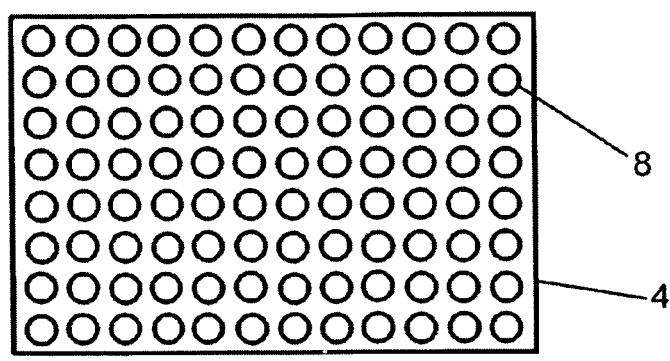
FIG. 1A is a top view of a small substrate micro-patterned chemical array.
FIG. 1B is a top view of a large substrate micro-patterned chemical array.
Figure 1:
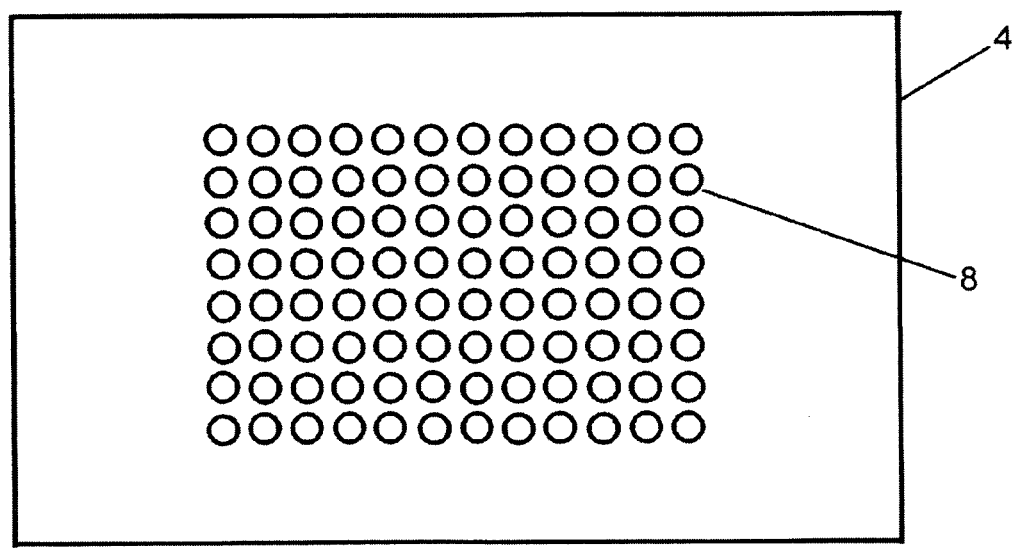

| | GUIDE TO THE FIGS. |
|---|---|
| 001 | fluidic location |
| 002 | array of fluidic locations, optionally with depressions |
| 003 | sub-array |
| 004 | substrate |
| 008 | cell binding location |
| 009 | chemical modification of the cell binding locations |
| 010 | cells arrayed on the cell binding locations |
| 012 | chamber |
| 013 | depression formed at fluidic location |
| 014 | input channel |
| 016 | output channel |
| 018 | cassette |
| 020 | spacer supports |
| 024 | micro-capillary tubes |
| 028 | raised reservoir |
| 030 | first channel |
| 032 | second channel |
| 036 | plug |
| 040 | array of fluidic locations |
| 044 | luminescence reader instrument |
| 048 | first storage compartment |
| 050 | first robotic arm |
| 052 | second robotic arm |
| 054 | second storage compartment |
| 056 | computer |
| 060 | Optics |
| 064 | computer controlled x-y-z stage |
| 068 | computer-controlled rotating nosepiece |
| 070 | low-magnification objective |
| 072 | high-magnification objective |
| 074 | while-light source lamp |
| 076 | excitation filter wheel |
| 078 | dichroic filter system |
| 080 | emission filters |
| 082 | detector (e.g., cooled CCD) |

TABLE 1-continued

GUIDE TO THE FIGS.

| | |
|---|---|
| 086 | computer screen |
| 090 | database |
| 140 | lateral space between wells |
| 160 | horizontal connecting channels |
| 180 | vertical connecting channels |
| 200 | switchable positive pressure source reservoirs or pumps |
| 220 | source reservoirs at atmospheric pressure |
| 240 | m × 1 valve-less manifold |
| 300 | waste reservoirs |
| 320 | switchable negative pressure waste reservoirs or pumps |
| 340 | thermodynamically-pumped waste reservoir |
| 400 | 1 × n valve manifold |
| 410 | n × 1 valve manifold |
| 420 | 2n × 1 valve manifold |
| 500 | Check Valve |
| 520 | Valve Element |
| 540 | Valve Seat |
| 560 | magnetic (B) field gradient |
| 580 | restoring force on magnetic ball check valve |
| 600 | Bead |
| 620 | Magnetic Field |
| 700 | Fill ports |
| 710 | Channels |
| 720 | Valves |
| 730 | Reservoirs |
| 740 | Electrokinetic pump |
| 760 | Electrode 1 |
| 780 | Electrode 2 |

DETAILED DESCRIPTION OF THE PREFERRED EMBODIMENTS

All patents, patent applications, and references cited herein are incorporated by reference in their entirety.

As used herein the term "well" is defined as the volume space created by the mating of one fluidic location of the chamber with one cell binding location on the substrate. The volume space may be created by a depression on the chamber corresponding to the fluidic location, by a depression on the substrate corresponding to the cell binding location, by a spacer support that separates the chamber and the substrate (wherein there is no requirement for a depression in the substrate of the chamber), a combination of any of these, or any other suitable method for creating a volume space between the fluidic location and the cell binding location.

As used herein, the term "cell binding location" refers to a discrete location on the substrate that comprises a plurality of cell binding sites capable of binding cells. The substrate may be derivatized to create cell binding sites, or the cell binding sites may naturally be present on the substrate. The plurality of cell binding sites within an individual cell binding location may be capable of binding only a single cell type, or may be capable of binding more than one cell type. Different cell binding locations on the same substrate may be identical or different in the type of cells that they are capable of binding.

The term "fluidic location" as used herein refers to a discrete location on the chamber that is the site of fluid delivery to and/or removal from the cell binding location. The fluidic location may comprise a depression, such as an etched domain, a raised reservoir, or any other type of depression. Alternatively, the fluidic location may be flat, such as the terminus of an input and/or output channel, or the terminus of a via that is in fluid connection with an input and/or output channel.

As used herein, the term "cassette" means the combination of the substrate and the chamber. The combination can be either modular (more than one piece), providing a reusable chamber and a disposable substrate, or non-modular (single piece), to limit any potential interwell leaking.

As used herein, the term "on-board" means integral with the cassette.

As used herein, the term "integrated fluidics" means that a microfluidic device comprises both a substrate surface for cell binding and a chamber.

As used herein, the term "chamber" means a fluid delivery system comprising microfluidic channels and fluidic locations, which serves as a specialized substrate cover.

As used herein, the term "switchable pump" refers to a pump, including but not limited to a syringe pump, a pressure-controlled vessel with a valve, or an electrokinetic pump that is employed externally (with the optional use of electrical shielding) with respect to the matrix of the array of wells, so that no harmful electric field effects are experienced by the cells.

As used herein, the term "sub-array" means any contiguous sub-section of wells in the entire array of wells, typically in a format corresponding to the shape of an imaging detector array, such as a CCD (charge coupled device detector).

As used herein the term "matrix of the cell array" means the space defined by the imaginary parallelpiped (i.e., typically a cubic or rectangular box) that would fit around the entire set of wells in the array of the cassette.

As used herein, the term "assay components" refers to any component that would be added to a cell screening assay, including but not limited to reagents, cells, test compounds, media, antibodies, luminescent and reporters.

As used herein, the term "luminescent" encompasses any type of light emission, including but not limited to luminescence, fluorescence, and chemiluminescence.

In one aspect, the present invention teaches a method of making a micro-array of multiple cell types on a common substrate. As defined herein, a micro-array of multiple cell types refers to an array of cells on a substrate that are not distributed in a single uniform coating on the support surface, but rather in a non-uniform fashion such that each "cell binding location" or groups of cell binding locations on the substrate may be unique in its cell binding selectivity.

The method of making a micro-array of multiple cell types comprises preparing a micro-patterned chemical array (also referred to herein as a chemically modified array of cell binding locations), chemically modifying the array non-uniformly, and binding cells to the non-uniform chemical array.

In a preferred embodiment, a micro-patterned chemical array comprises a substrate 4 which is treated to produce a hydrophobic surface across which are dispersed at regular intervals hydrophilic spots or "cell binding locations" 8. (FIGS. 1A–1B). The substrate can be a glass, plastic, or silicon wafer, such as a conventional light microscope coverslip, but can also be made of any other suitable material to provide a substrate. As describe previously, the term "cell binding locations" is used to describe a specific spot on the substrate, and does not require any particular depth. The surface of the substrate 4 is preferably about 2 cm by 3 cm, but can be larger or smaller. In a preferred embodiment, the cell binding locations 8 of the micro-patterned chemical array contain reactable functional groups such as, but not limited to, amino hydroxyl, sulfhydryl or carboxyl groups that can bind to cells non-specifically or be further chemically modified to bind molecules that bind cells specifically.

Chemically modified cell binding locations are produced by specific chemical modifications of the cell binding locations on the substrate. The cell binding locations may comprise a variety of different cell binding molecules that permit attachment and growth of different types of cells in the cell binding locations, or may permit attachment of only a single cell type. The hydrophobic domains surrounding the cell binding locations on the substrate do not support the attachment and growth of the cells.

In one embodiment, a micro-array of multiple cell types is made by coating a glass wafer via chemisorbance with a layer of a substance having reactable functional groups such as amino groups. In a preferred embodiment, an aminosilane such as 3-amino propyltrimethoxysilane (APTS) or N-(2-aminoethyl-3-aminopropyl)trimethoxysilane (EDA) is used, but other reactable substances may be used. Following this first step, due to the presence of the reactable functional groups, the entire surface of the coated glass wafer is hydrophilic.

Secondly, a micro-patterning reaction is carried out where drops containing a substance having photo-cleavable or chemically removable amino protecting groups are placed in a micro-pattern of discrete locations on the aminosilane coated glass wafer. In one embodiment the pattern comprises a rectangular or square array, but any suitable discrete pattern, may be used (such as, but not limited to, triangular or circular). In one embodiment, the drops range in volume from 1 nanoliter (nl) to 1000 nl. In a preferred embodiment the drops range from 250–500 nl in volume. Suitable photochemically removable amino protecting substances include, but are not limited to 4-bromomethyl-3-nitrobenzene, 1-(4,5-dimethoxy-2-nitrophenyl)-ethyl (DMNPE) and butyloxycarbonyl. In one embodiment, the patterning reaction is carried out for 1 to 100 minutes at temperatures ranging from ambient temperature to 37° C., using reagent concentrations of between 1 micromolar (uM) and 1000 uM. In a preferred embodiment, the reaction is carried out at 37° C. for 60 minutes using a reagent concentration of 500 uM.

Figure 2:
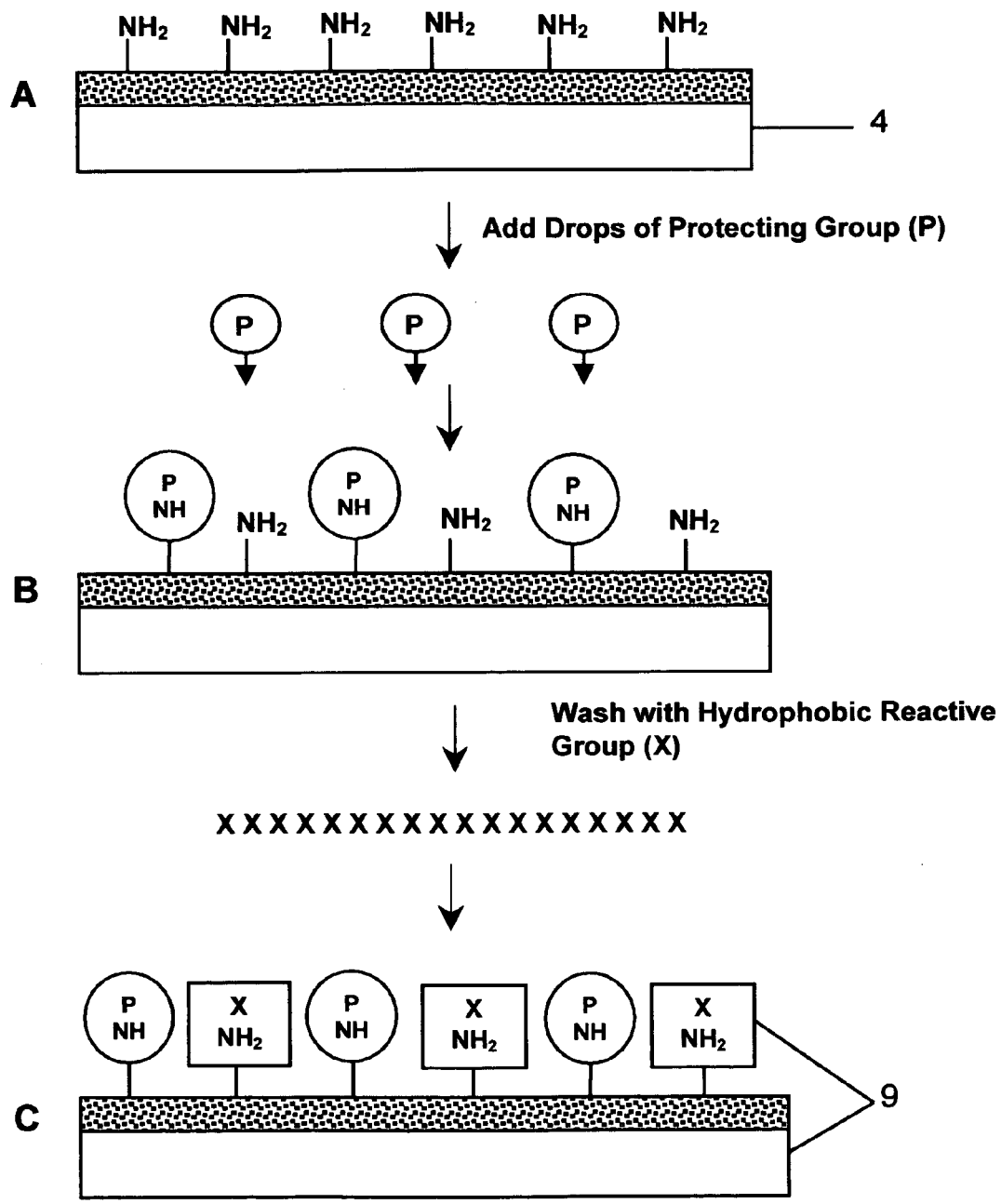
FIG. 2 diagrams a method of producing a micro-patterned chemical array on a substrate.

The drops may be placed onto the aminosilane coated glass wafer via conventional ink-jet technology. (U.S. Pat. No. 5,233,369; U.S. Pat. No. 5,486,855). Alternatively, an array of pins, defined herein as tapered rods that can transfer between 1 nl and 1000 nl of fluid, is dipped into a bath of the amino protecting substance to produce drops of the protecting substance on their ends. The pins are then contacted with the glass wafer to transfer the drops thereto. In another embodiment, an array of capillary tubes made of glass or plastic, as described in U.S. Pat. Nos. 5,567,294 and 5,527,673, (both herein incorporated by reference), containing the amino protecting substance is contacted with the glass wafer to transfer the droplets to the surface. Thus, the glass wafer is micro-patterned with an array of spots or cell binding locations that contain protected amino groups on a hydrophobic surface (FIGS. 2A–B).

Third, a hydrophobic substance reactive with unprotected amino groups is washed over the glass wafer. The hydrophobic substance can be a fatty acid or an alkyl iodide, or any other suitable structure. Certain conditions for such a derivatization of glass can be found in Prime and Whitesides, Science 252:1164–1167, 1991, Lopez et al., J. Am. Chem. Soc. 115:5877–5878, 1993, and Mrksich and Whitesides, Ann. Rev. Biophys. Biomol. Struct. 25:55–78, 1996. The fatty acid or alkyl iodide reacts with the unprotected amino groups and covalently attaches thereto, and the amino groups are now hydrophobic due to the fatty acid or alkyl iodide group. The resulting modified array of cell binding locations 9 comprises a glass wafer 4 with an array of cell binding locations 8 containing protected amino groups on a hydrophobic background. (FIG. 2C).

Fourth, the non-uniform array of cell binding locations is produced by uniformly de-protecting the amino groups in a micro-patterned chemical array produced according to the above-described methods. In one embodiment, chemical specificity can be added by chemically crosslinking specific molecules to the cell binding locations. There are a number of well known homo- or hetero-bi-functional crosslinking reagents such as ethylene glycol bis(succinimidylsuccinate) that will react with the free amino groups in the cell binding locations and crosslink to a specific molecule. Reagents and conditions for crosslinking free amino groups with other biomolecules are well known in the art, as exemplified by the following references: Grabarek and Gergely, Analyt. Biochem 185:131–135, 1990; McKenzie et al., J. Prot. Chem. 7:581–592, 1988; Brinkley, Bioconjugate Chem. 3:12–13; 1992, Fritsch et al., Bioconjugate Chem. 7:180–186, 1996; and Aplin and Hughes, 1981.

In a preferred embodiment, a non-uniform array of cell binding locations is produced in combinatorial fashion. The resulting cell binding locations are non-uniform (i.e., each cell binding location or group of cell binding locations may be unique in its cell binding selectivity). By the term combinatorial, it is meant that the cell binding locations are variably treated.

In one embodiment, the protected amino groups of the modified array of cell binding locations of step 3 are de-protected and then specific molecules with chemical crosslinking reagents are deposited in a desired pattern. The specific crosslinking agents can bind to the amino groups and further possess a cell-binding group. In this step, the type of cell binding group can be varied from one cell binding location to another, or from one group of cell binding locations to another, to create a non-uniform design in the array.

In another embodiment, the amino groups of the chemically modified cell binding locations of step 3 are uniformly de-protected. A photo-activatable crosslinker is reacted with the de-protected amino groups. An optical mask of a desired pattern is placed over the surface of the cell binding locations and the exposed cell binding locations are illuminated with a light source. The position and number of cell binding locations that receive light is controlled by the micro-pattern of the optical mask. Suitable photo-activatable crosslinkers include aryl nitrenes, fluorinated aryl azides, benzophenones, and diazopyruvates. Reagents and conditions for optical masking and crosslinking are discussed in Prime and Whitesides, 1991; Sighvi et al., 1994, Sigal et al., 1996 and Mrksich and Whitesides, 1996. The photo-activatable crosslinker is bi-functional in that it chemically bonds to the amino group on the cell binding locations and, when exposed to light, covalently bonds to cell binding molecules, such as antibodies. Reagents and conditions for photoactivated crosslinking are discussed in Thevenin et al., Eur. J. Biochem. 206:471–477, 1992 and Goldmacher et al., Bioconjugate Chem. 3:104–107, 1992.

When a photo-activatable crosslinker is used, the glass plate is flooded with cell binding molecules to be bound to the cell binding locations. In one embodiment, cell binding molecules such as cell surface antigen-reactive antibodies, extracellular matrix proteins, (for example, fibronectin or collagen) or charged polymers (for example poly-L-lysine or poly-L-arginine) are used in concentrations ranging from about 0.1 to about 1 mM. While the cell binding molecules cover the cell binding locations, the glass plate is irradiated from the underside of the glass plate, at an angle below the critical angle of the material of the glass plate, resulting in total internal reflection of the light. (For discussion of total internal reflection fluorescence microscopy, see Thompson et al., 1993). In one embodiment, the irradiation is carried out at between ambient temperature and 37° C. for 0.1 to 10 seconds with light of wavelength between 300 nanometers (nm) to 1000 nm. In a preferred embodiment, the irradiation is conducted at ambient temperature for 1 second using light with a wavelength of between about 300 and 400 nm. Optical crosslinking limits the photo-activatable crosslinking to a short distance into the solution above the cell binding locations, and is described in Bailey et al., Nature 366:44–48, 1993; Farkas et al., Ann. Rev. Physiol. 55:785–817, 1993; Taylor et al., Soc. Opt. Instr. Eng. 2678:15–27, 1996; Thompson et al., in Mason, W. T. (ed.), "Fluorescent and Luminescent Probes for Biological Activity." San Diego: Academic Press pp. 405–419, 1993.

The photo-activatable crosslinker binds with the cell binding molecules such as antibodies and matrix proteins, only in the cell binding locations where the crosslinker was irradiated. For example, a single row of an array of cell binding locations can be irradiated to produce a single row of cell binding locations with cell binding molecules bound to the crosslinker. Following a washing of the array to eliminate any unbound cell binding molecule, a second row of cell binding locations can be bound to a second cell binding molecule by subsequent flooding of the glass wafer with the second cell binding molecule while irradiating the second row and optically masking the other rows. Unbound cell binding molecules are removed by washing the array with PBS, or any other suitable buffer. In this fashion, multiple rows of cell binding locations or groups of cell binding locations can be sequentially illuminated by sequential masking in the presence of a particular cell binding molecule. Alternatively, each cell binding location can be irradiated one by one using pinpoint exposure and optical masking. In this manner, different cell binding molecules are bound to rows of the array or to individual cell binding locations, creating a non-uniform array of cells bound to the cell binding locations of any desired pattern.

In a further embodiment for producing chemically modified arrays of cell binding locations, a chemically modified array is first produced, wherein the amino groups of the cell binding locations are uniformly protected with photo-cleavable protecting groups. Rows, columns, and/or individual cell binding locations are sequentially photo-deprotected to expose the free amino groups by using an optical mask of various patterns to cover all but the cell binding locations to be de-protected. The exposed cell binding locations (i.e., those not covered by the mask), are illuminated, resulting in removal of the protecting groups. The array is flooded with a bi-functional crosslinker which chemically bonds to the de-protected amino group and activates the cell binding locations. Conditions for the photode-protection of amino groups are discussed in Padwa, A. (ed.) "Organic Photochemistry.", New York 9:225–323, 1987, Ten et al., Makromol. Chem. 190:69–82, 1989, Pillai, Synthesis 1980:1–26, 1980, Self and Thompson, Nature Medicine 2:817–820, 1996 and Senter et al., Photochem. Photobiol. 42:231–237, 1985. Next, cell binding molecules are flooded onto the modified chemical array wherein they react with the other half of the crosslinker. The array is then washed to eliminate any unbound bi-functional crosslinker and cell binding molecules. Another cell binding location or set of cell binding locations may be de-protected using another optical mask, and the array may then be flooded with a second treatment of a bi-functional crosslinker followed by a distinct cell binding molecule which bonds to this second cell binding location or set of cell binding location of de-protected amino groups. The array is washed to eliminate the second treatment of a bi-functional crosslinker and cell binding molecules. A non-uniform array of cell binding molecules may thus be produced by a repeated sequence of photo-de-protection, chemical crosslinking of specific molecules and washing under a variety of masks. Alternatively, the crosslinking reagents can be delivered to the de-protected cell binding locations together with the cell binding molecules in one step. Concentration gradients of attached cell binding molecules can be created by controlling the number of de-protected amino groups exposed using an optical mask, or by controlling the dose of irradiation for the photo-activatable crosslinkers.

The chemically modified array of cell binding locations is then used to produce a non-uniform array of cells on the cell binding locations. In one embodiment, the modified chemical array is "seeded" with cells by introducing suspended cells onto the array, allowing binding of the cells to the cell binding locations and then rinsing the wafer to remove unbound and weakly bound cells. The cells are bound only in the cell binding locations, because the specific chemical environment in the cell binding locations, in conjunction with the hydrophobic environment surrounding each of the cell binding locations, permits the selective binding of cells to the cell binding locations only. Furthermore, the modification of cell binding locations with specific cell-binding molecules permits selective binding of cells to specific cell binding locations, producing a non-uniform array of cells on the cell binding locations. In addition, the cell surface molecules that specifically bind to the cell binding locations may be either naturally present or genetically engineered by expressing "cell binding location-specific" molecules that have been fused to cellular trans-membrane molecules such that cells interact with and bind specifically to modified cell binding locations. The creation of an array of cell binding locations with different cell recognition molecules allows one cell binding location, a group of cell binding locations, or the entire array to specifically "recognize", grow and screen cells from a mixed population of cells.

In one embodiment, cells suspended in culture medium at concentrations ranging from about $10^3$ to about $10^7$ cells per ml are incubated in contact with the cell binding locations for 1 to 120 minutes at temperatures ranging from ambient temperature to 37° C. Unbound cells are then rinsed off of the cell binding locations using culture medium or a high density solution to lift the unbound cells away from the bound cells. (Channavajjala, et al., J. Cell Sci. 110:249–256, 1997). In a preferred embodiment, cells suspended in culture medium at concentrations ranging from about $10^5$ to about $10^6$ cells per ml are incubated in contact with the cell binding locations at 37° C. for times ranging from about 10 minutes to about 2 hours.

The density of cells attached to the cell binding locations is controlled by the cell density in the cell suspension, the time permitted for cell attachment to the chemically modified cell binding locations and/or the density of cell binding molecules in the cell binding locations. In one embodiment of the cell attachment procedure, $10^3$– to $10^7$ cells per ml are incubated at between ambient temperature and 37° C. for between 1 minute and 120 minutes, with cell binding locations containing between 0.1 and 100 nmoles per $cm^2$ of cell binding molecules. In a preferred embodiment, $10^5$ and $10^6$ cells per ml are incubated for 10 minutes to 2 hours at about 37° C., with cell binding locations containing about 10 to 100 nmoles per $cm^2$ of cell binding molecules.

In one embodiment, the cells may be chemically fixed to the cell binding locations as described by Bell et al., J. Histochem. Cytochem 35:1375–1380, 1987; Poot et al., J. Histochem. Cytochem 44:1363–1372, 1996; Johnson, J. Elect. Micros. Tech. 2:129–138, 1985, and then used for screening at a later time with luminescently labeled molecules such as antibodies, nucleic acid hybridization probes or other ligands.

In another embodiment, the cells can be modified with luminescent indicators of cell chemical or molecular properties, seeded onto the non-uniform chemically modified array of cell binding locations and analyzed in the living state. Examples of such indicators are provided in Giuilano et al., Ann. Rev. Biophys. Biomol. Struct. 24:405–434, 1995; Harootunian et al., Mol. Biol. Cell 4:993–1002, 1993; Post et al., Mol. Biol. Cell 6:1755–1768, 1995; Gonzalez and Tsien, Biophys. J. 69:1272–1280, 1995; Swaminathan et al., Biophys. J. 72:1900–1907, 1997 and Chalfie et al., Science 263:802–805, 1994. The indicators can be introduced into the cells before or after they are seeded onto the array by any one or a combination of variety of physical methods, such as, but not limited to diffusion across the cell membrane (reviewed in Haugland, Handbook of fluorescent probes and research chemicals, $6^{th}$ ed. Molecular Probes, Inc., Eugene, 1996), mechanical perturbation of the cell membrane (McNeil et al., J. Cell Biology 98:1556–1564, 1984; Clarke and McNeil, J. Cell Science 102:533–541, 1992; Clarke et al., BioTechniques 17:1118–1125, 1994), or genetic engineering so that they are expressed in cells under prescribed conditions. (Chalfie et al., 1994). In a preferred embodiment, the cells contain luminescent reporter genes, although other types of reporter genes, including those encoding chemiluminescent proteins, are also suitable. Live cell studies permit analysis of the physiological state of the cell as reported by luminescence during its life cycle or when contacted with a drug or other reactive substance.

Figure 3A:
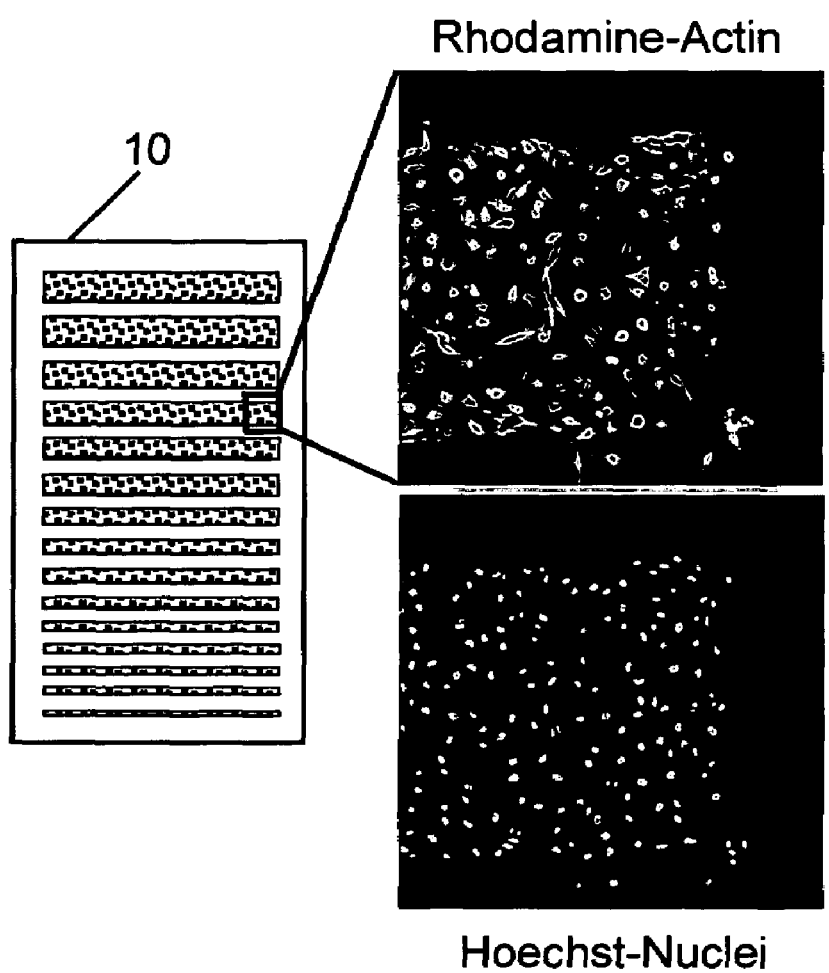
FIG. 3A is a photograph showing fibroblastic cell growth on a surface patterned chip, attached to a micro-patterned chemical array and labeled with two fluorescent probes.

In another aspect of the present invention, a non-uniform cell array on the cell binding locations is provided, wherein cells are non-uniformly bound to a chemically modified array of cell binding locations on a substrate. The cell array is non-uniform because the underlying non-uniform chemically modified array of cell binding locations provides a variety of cell binding sites of different specificity. Any cell type can be arrayed, providing that a molecule capable of specifically binding that cell type is present in the chemically modified array of cell binding locations. Preferred cell types for the non-uniform cell array on the cell binding locations include lymphocytes, cancer cells, neurons, fungi, bacteria and other prokaryotic and eukaryotic organisms. For example, FIG. 3A shows a non-uniform cell array on the cell binding locations containing fibroblastic cells grown on a surface patterned substrate and labeled with two fluorescent probes (rhodamine to stain actin and Hoechst to stain nuclei), while FIG. 3B shows a non-uniform cell array on the cell binding locations containing fibroblastic cell growth (L929 and 3T3 cells) in spotted patterns, labeled with two fluorescent probes and visualized at different magnifications.

Examples of cell-binding molecules that can be used in the non-uniform cell array on the cell binding locations include, but are not limited to antibodies, lectins and extracellular matrix proteins. Alternatively, genetically engineered cells that express specific cell surface markers can selectively bind directly to the modified cell binding locations. The non-uniform cell array on the cell binding locations may comprise either fixed or living cells. In a preferred embodiment, the non-uniform cell array on the cell binding locations comprises living cells such as, but not limited to, cells "labeled" with luminescent indicators of cell chemical or molecular properties.

In another aspect of the present invention, a method for analyzing cells is provided, comprising preparing a non-uniform cell array on the cell binding locations wherein the cells contain at least one luminescent reporter molecule, contacting the non-uniform cell array on the cell binding locations to a fluid delivery system to enable reagent delivery to the cells, conducting high-throughput screening by acquiring luminescence image of the entire non-uniform cell array at low magnification to detect luminescence signals from all cell binding locations at once to identify those that exhibit a response. This is followed by high-content detection within the responding cell binding locations using a set of luminescent reagents with different physiological and spectral properties, scanning the selected cell binding locations to obtain luminescence signals from the luminescent reporter molecules in the cells, converting the luminescence signals into digital data and utilizing the digital data to determine the distribution, environment or activity of the luminescent reporter molecules within the cells.

Figure 4:
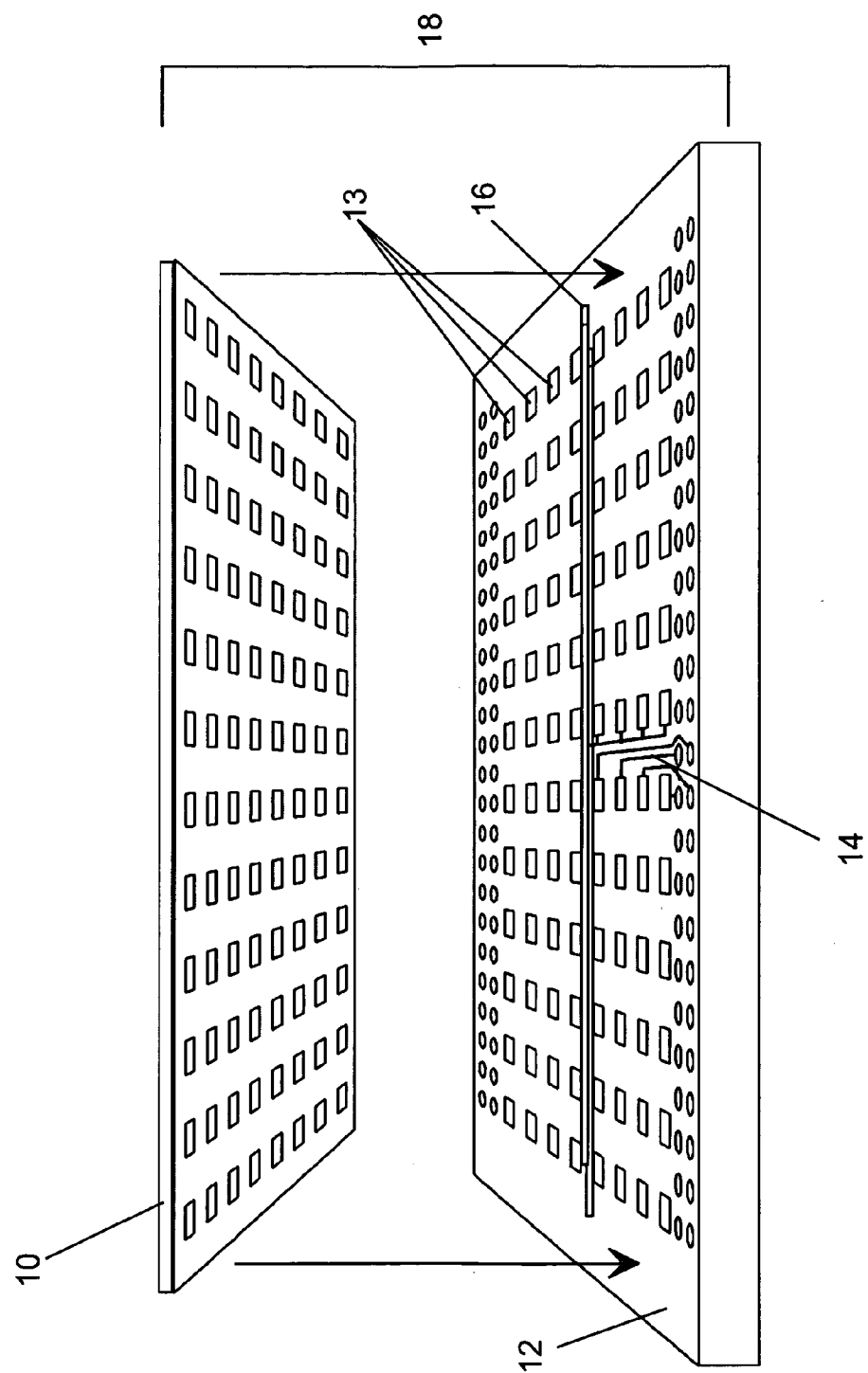
FIG. 4 is a diagram of the cassette which is the combination of the micro-array of multiple cell types top and chamber bottom.

Preferred embodiments of the non-uniform cell array on the cell binding locations are disclosed above. In a preferred embodiment of the fluid delivery system, a chamber, mates with the substrate containing the non-uniform cell array. The chamber is preferably made of glass, plastic or silicon, but any other material that can provide a chamber is suitable. One embodiment of the chamber 12 shown in FIG. 4 has an array of etched domains 13 matching the cell binding locations 8 on the substrate 4. In addition, input channels 14 are etched to supply fluid to the etched domains 13. A series of "output" channels 16, to remove excess fluid from the etched domains 13, can also be connected to the cell binding locations. The chamber 12 and substrate 10 together constitute a cassette 18. While this embodiment utilizes etched domains, any other type of depression 13 formed at the fluidic location 1 can also be utilized in this embodiment. Alternatively, the fluidic location may be flat and the cell binding locations 8 may comprise depressions that match the fluidic locations 1. In another alternative, both the cell binding site 8 and the fluidic location 1 are flat, and a volume space for the well is created by the use of a spacer support 20 between the substrate 4 and the chamber 12.

The chamber 12 is thus used for delivery of fluid to the cells arrayed on the cell binding locations 10. The fluid can include, but is not limited to a solution of a particular drug, protein, ligand, or other substance which binds with surface expressed moieties of cells or that are taken up by the cells. The fluid to interact with the cells arrayed on the cell binding locations 10 can also include liposomes encapsulating a drug. In one embodiment, such a liposome is formed from a photochromic material, which releases the drug upon exposure to light, such as photoresponsive synthetic polymers. (Reviewed in Willner and Rubin, Chem. Int. Ed. Engl. 35:367–385, 1996). The drug can be released from the liposomes in all channels 14 simultaneously, or individual channels or separate rows of channels may be illuminated to release the drug sequentially. Such controlled release of the drug may be used in kinetic studies and live cell studies. Control of fluid delivery can be accomplished by a combination of micro-valves and micro-pumps that are well known in the capillary action art. (U.S. Pat. No. 5,567,294; U.S. Pat. No. 5,527,673; U.S. Pat. No. 5,585,069, all herein incorporated by reference.)

Figure 5:
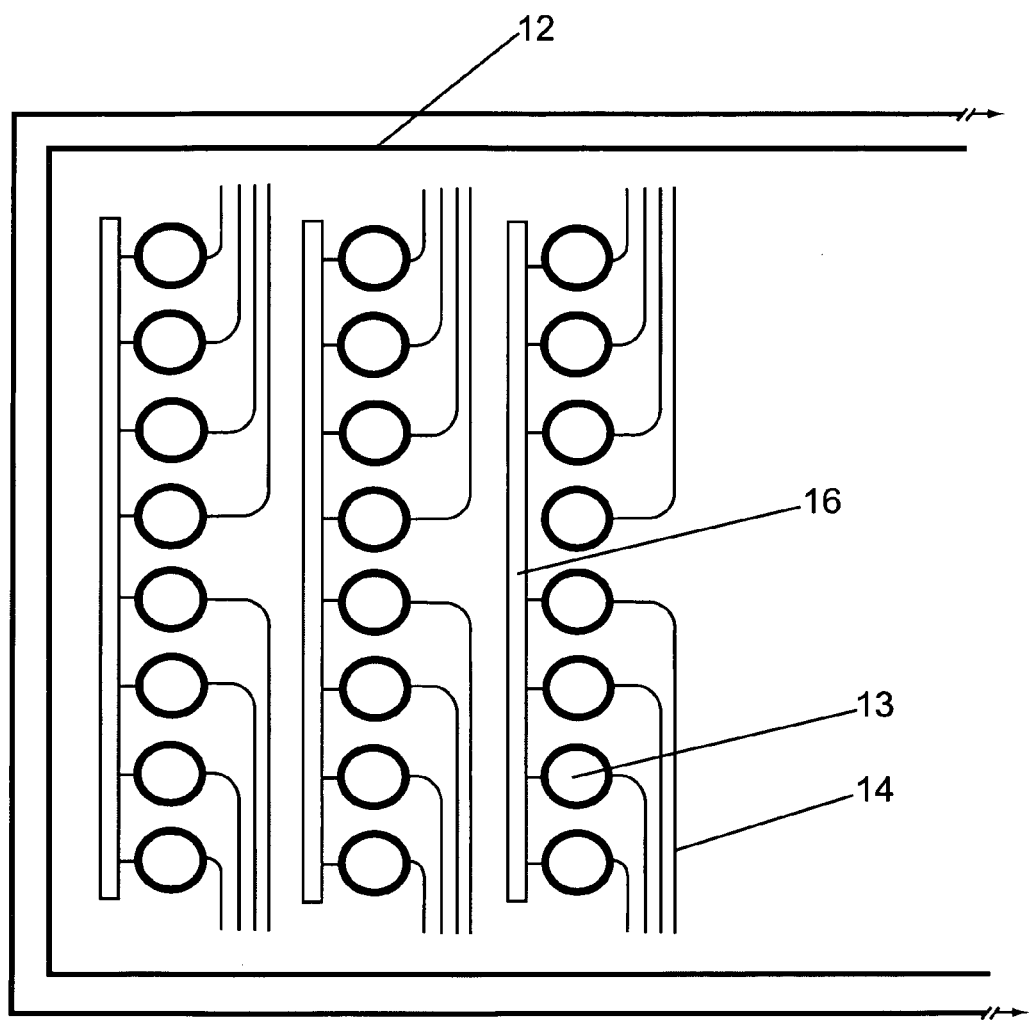
FIG. 5 is a diagram of a chamber that has nanofabricated input channels to address "wells" in the non-uniform micro-patterned array of cells.
Figure 6:
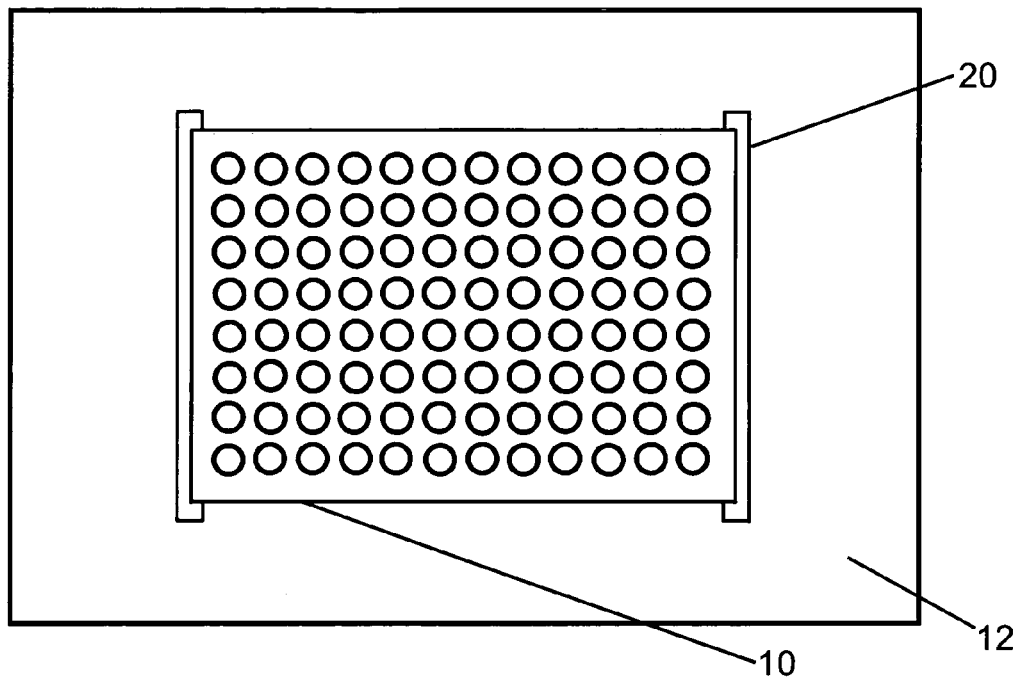
FIG. 6 is a diagram of a chamber with no channels.

Another embodiment of the chamber 12 shown in FIG. 5 has an array of input channels 14 matching the chamber's etched domains 13 which are slightly larger in diameter than the cell binding locations 8 on the substrate 4, so that the cell binding sites are immersed into the etched domains 13 of the chamber 12. Spacer supports 20 are placed between the chamber 12 and the cells arrayed on the cell binding locations 10 along the sides of contact. The substrate 4 and the chamber 12 can be sealed together using an elastomer or other sticky coating on the raised region of the chamber. Each etched domain 13 of the chamber 12 can be individually or uniformly filled with a medium that supports the growth and/or health of the cells arrayed on the cell binding locations 10. In a further embodiment (FIG. 6), the chamber contains no input channels, for treating all the cells arrayed on the cell binding locations 10 with the same solution.

Figure 7:
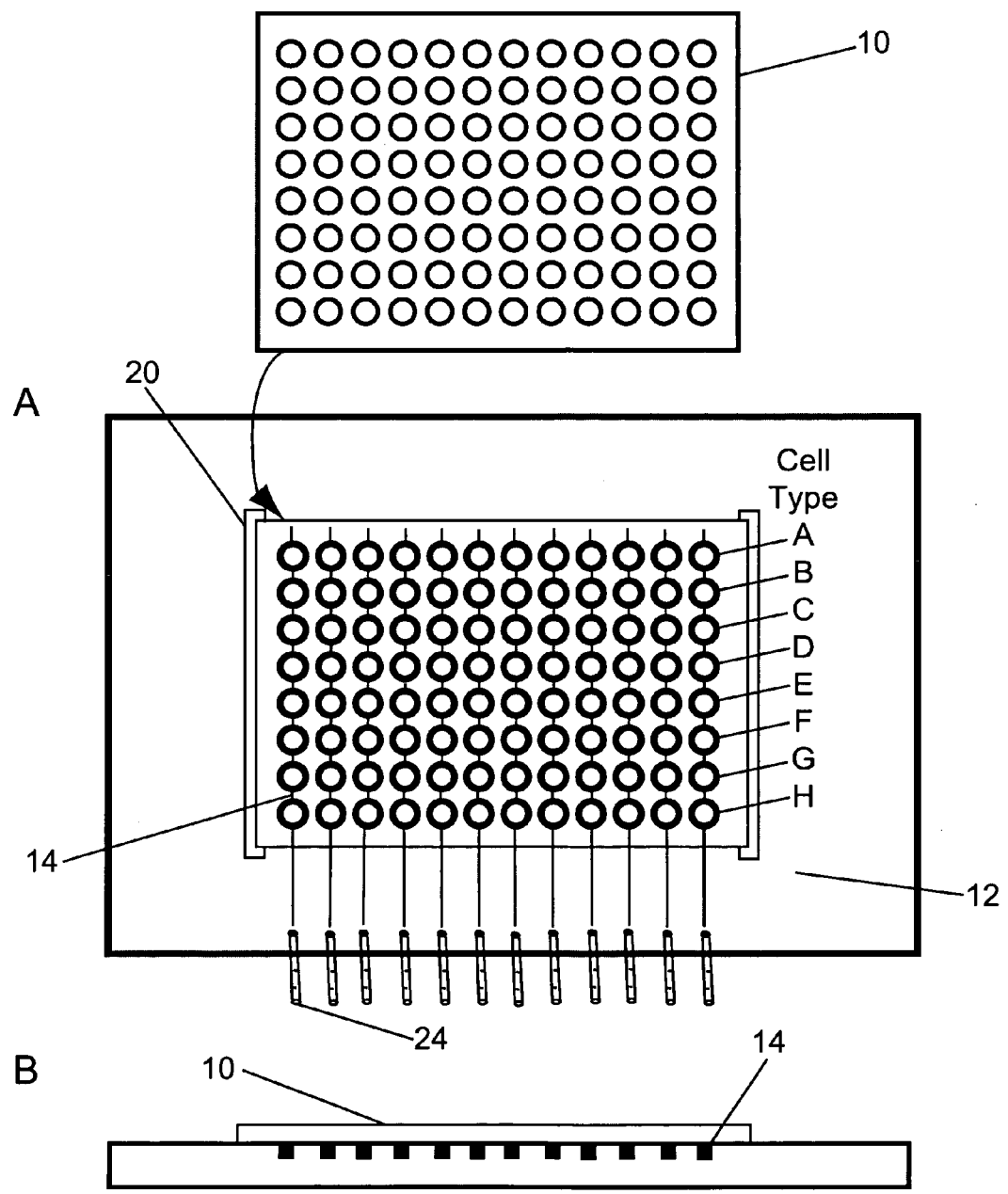
FIG. 7A is an overhead diagram of a chamber with microfluidic channels etched onto the substrate.
FIG. 7B is a side view diagram of a chamber with microfluidic channels etched onto the substrate.

Delivery of drugs or other substances is accomplished by use of various modifications of the chamber as follows. A solution of the drug to be tested for interaction with cells of the array can be loaded from a 96 well microtiter plate into an array of micro-capillary tubes 24. (FIG. 7). The array of micro-capillary tubes 24 corresponds one-to-one with the input channels 14 of the chamber 12, allowing solution to flow or be pumped out of the micro-capillary tubes 24 into the channels 14. The cassette 18 is inverted so that the cell binding locations 8 become submerged in the etched domain 13 filled with the fluid (FIG. 7B). Once the interaction between the fluid and cells occurs, luminescence signals emanating from the cells arrayed on the cell binding locations 10 can be measured directly or, alternatively, the substrate 4 can be lifted off the chamber for post processing, fixation, and labeling. The placement and removal of the array of cells may be accomplished via robotics and/or hydraulic mechanisms. (Schroeder and Neagle, 1996).

In one embodiment of the chamber 12 shown in FIG. 7, the channels and matching etched domains 13 are etched into the chamber chemically (Prime and Whitesides, 1991; Lopez et al., 1993; Mrksich and Whitesides, 1996). The etched domains 13 are larger in diameter than the cell binding locations 8. This permits the chamber 12 to be contact sealed to the substrate 4, leaving space for the cells and a small volume of fluid. Input channels 14 are etched into each row of etched domains 13 of the chamber 12. Each input channel 14 extends from two opposing edges of the chamber 12 and is open at each edge. The etched domains 13 of a single row are in fluid communication with the input channels 14 by placing a micro-capillary tube 24 containing a solution into contact with the edge of the chamber 12. Each row of connected input channels 14 can be filled simultaneously or sequentially. During filling of the input channels 14 by valves and pumps or capillary action, each of the channels of the chamber 12 fills and the drug passes to fill each etched domain 13 in the row of etched domains 13 connected by the input channel 14.

Figure 8:
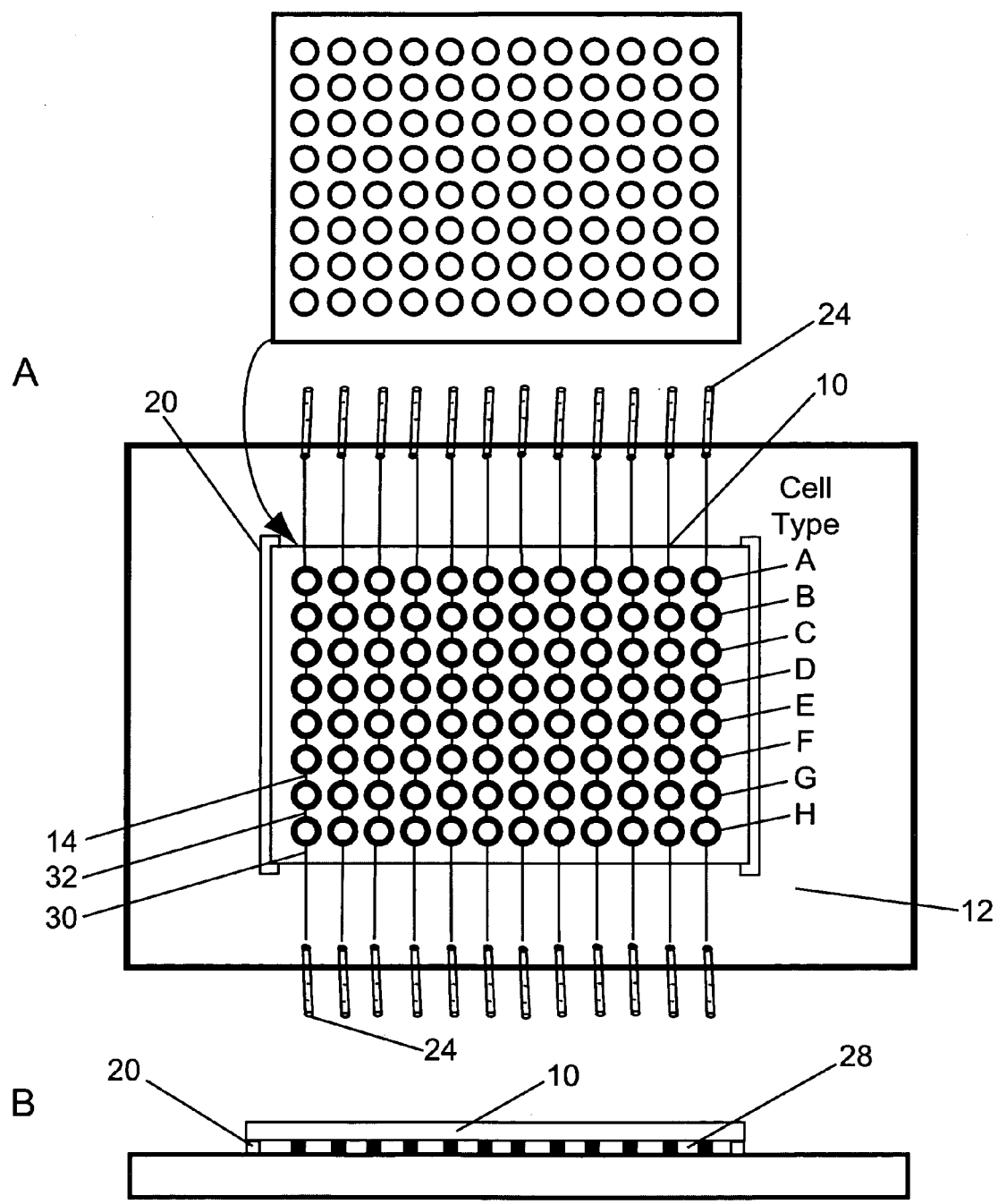
FIG. 8A is an overhead diagram of a chamber where the microfluidic channels and wells are formed from a raised matrix of a material stamped onto the fluid delivery chamber.
FIG. 8B is a side view diagram of a chamber where the microfluidic channels and wells are formed from a raised matrix of a material stamped onto the fluid delivery chamber.

In a further embodiment of the chamber 12, raised reservoirs 28 and input channels 14 can be placed onto the surface of the chamber 12 as shown in FIG. 8b. In a preferred embodiment, the raised reservoirs 28 and input channels 14 can be made from polytetrafluoroethylene or elastomeric material, but they can be made from any other sticky material that permits attachment to the substrate 4, such as poly(dimethylsiloxane), manufacture by Dow Corning under the trade name SYLGARD 184™. The effect is the same as with a chamber having etched channels and channels and its uses are similar.

In another embodiment of the chamber shown in FIG. 8A, a first channel 30 extends from one edge of the chamber 12 to a first etched domain 13 or raised reservoirs 28 and channels. A second channel 32 extends from the opposing edge to a second etched domain adjacent the first etched domain. The first 30 and second 32 channels are not in fluid communication with each other yet are in the same row of input channels 14 or raised reservoirs 28.

Figure 9:
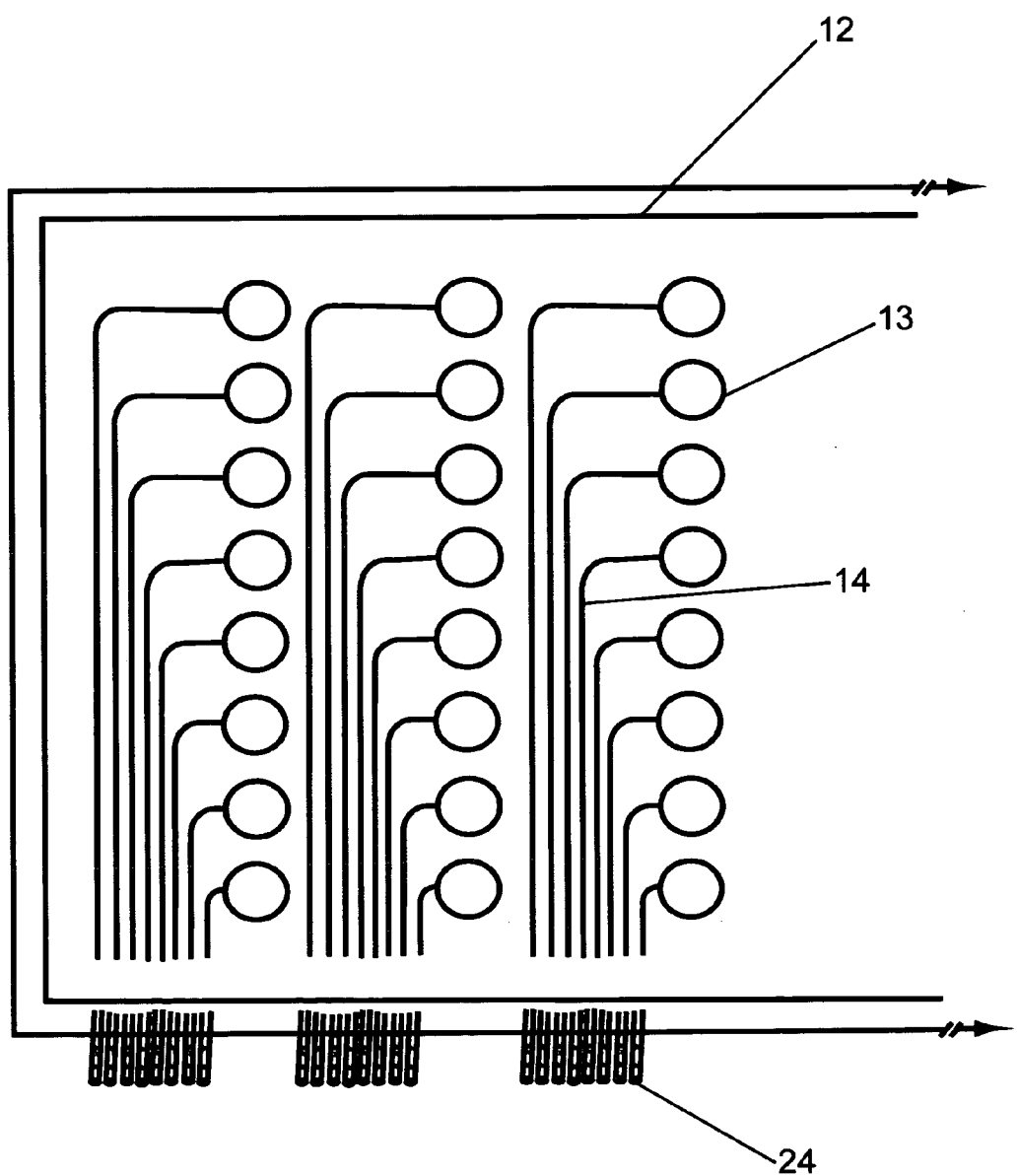
FIG. 9 is a diagram of a chamber where each well is addressed by a channel originating from one side of the chamber.
Figure 10:
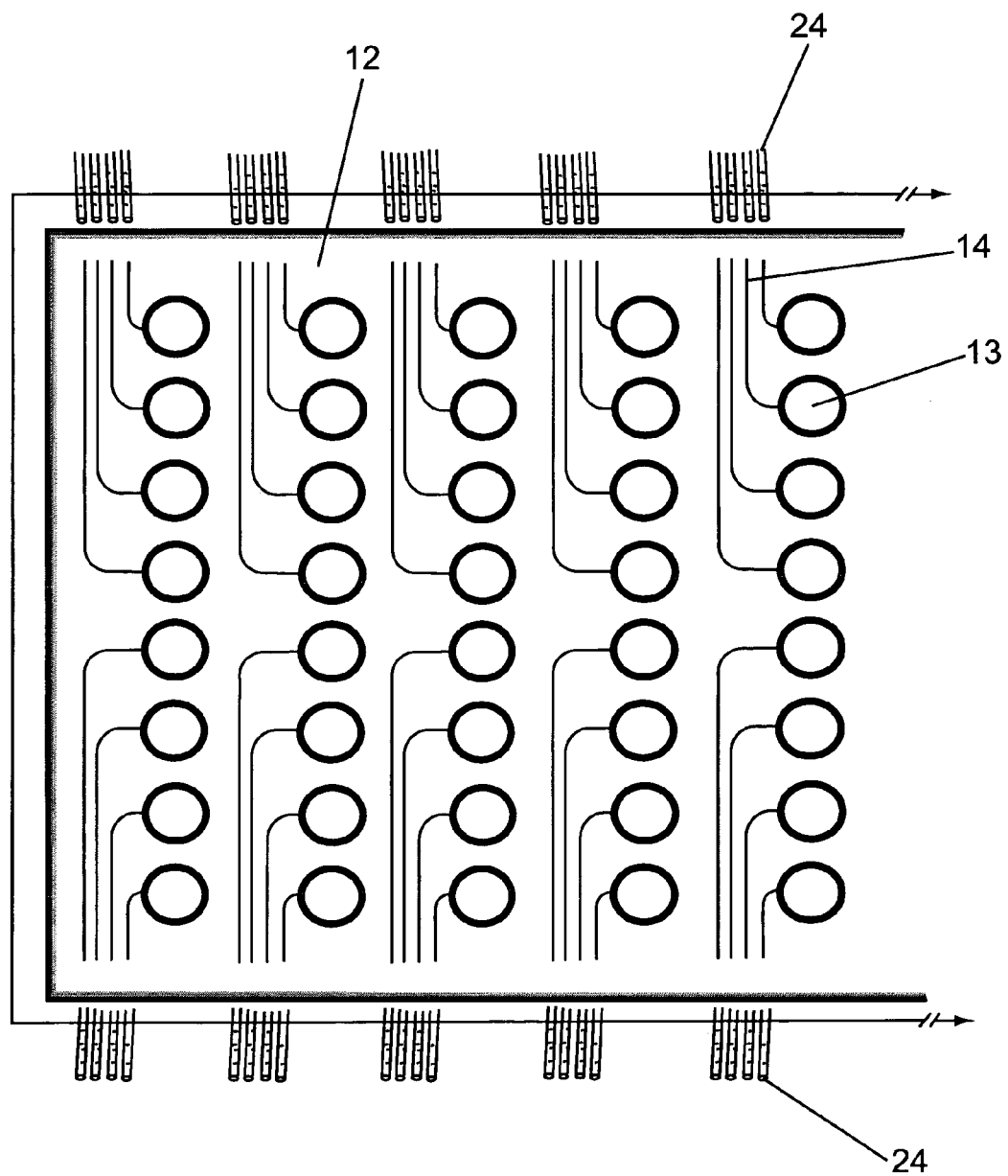
FIG. 10 is a diagram of a chamber where the wells are addressed by channels originating from two sides of the chamber.

In another embodiment, as shown in FIGS. 9 and 10, the chamber 12 may have an input channel 14 extending from each etched domain 13 or raised reservoir 28 to the edge of the chamber. The channels 14 can all originate from one edge of the chamber 12 (FIG. 9), or from both edges (FIG. 10). The input channels 14 can also be split to both sides of the etched domains 13 to minimize the space occupied by the input channels 14. Separate fluidic channels allow for performance of kinetic studies where one row at a time or one depression at a time is charged with the drug.

Figure 11:
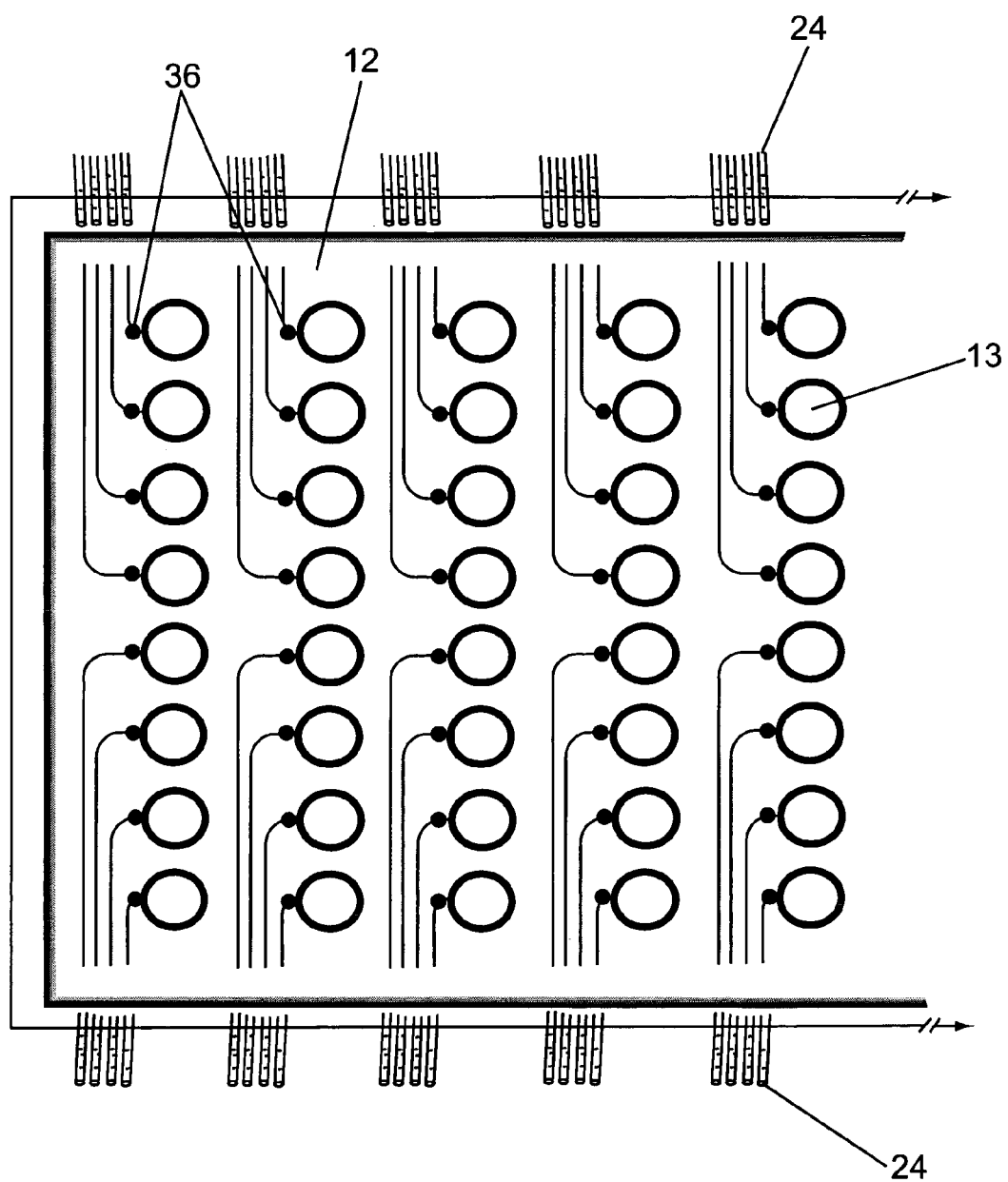
FIG. 11 is a diagram of a chamber where the microfluidic switches are controlled by light, heat or other mechanical means.

In a further embodiment depicted in FIG. 11, each etched domain 13 is in fluid communication with a corresponding input channel 14 having a plug 36 between the end of the channel 14 and the etched domain 13, which prevents the injected solution from flowing into the etched domain 13 until the desired time. Solutions may be preloaded into the input channels 14 for use at a later time. A plug 36 likewise can be disposed between a terminal etched domain 13 in a set of connected etched domains 13 in fluid communication with an input channel 14. Upon release of the plug 36, the substance flows through and fills all the etched domains 13 which are in fluid communication with the input channel 14.

In one embodiment, the plugs 36 are formed of a hydrophobic polymer, such as, but not limited to proteins, carbohydrates or lipids that have been crosslinked with photo-cleavable crosslinkers that, upon irradiation, becomes hydrophilic and passes along with the drug into the depression. Alternatively, the plug 36 may be formed of a crosslinked polymer, such as proteins, carbohydrates or lipids that have been crosslinked with photo-cleavable crosslinkers that, when irradiated, decomposes and passes into the etched domain 13 along with the solution.

The cassette 18, which comprises the substrate 4 and the chamber 12, is inserted into a luminescence reader instrument. The luminescence reader instrument is an optical-mechanical device that handles the cassette, controls the environment, controls delivery of solutions to wells, and analyzes the luminescence emitted from the array of cells, either one well at a time or the whole array simultaneously. In a preferred embodiment (FIG. 12), the luminescence reader instrument 44 comprises an integrated circuit inspection station using a fluorescence microscope as the reader and microrobotics to manipulate the cassettes. The reader of the present invention can comprise any optical system designed to image a luminescent specimen onto a detector. A storage compartment 48 holds the cassettes 18, from where they are retrieved by a robotic arm 50 that is controlled by computer 56. The robotic arm 50 inserts the cassette 18 into the luminescence reader instrument 44. The cassette 18 is removed from the luminescence reader instrument 44 by another robotic arm 52, which places the cassette 18 into a second storage compartment 54.

The luminescence reader instrument 44 is an optical-mechanical device designed as a modification of light optical-based, integrated circuit inspection stations used to "screen" integrated circuit "chips" for defects. Systems integrating environmental control, micro-robotics and optical readers are produced by companies such as Carl Zeiss [Jena, GmbH]. In addition to facilitating robotic handling, fluid delivery, and fast and precise scanning, two reading modes, high content and high throughput are supported.

High-content readout is essentially the same as that performed by the ARRAYSCAN™ reader (U.S. Pat. No. 5,989,835). In the high content mode, each location on the micro-array of multiple cell types is imaged at magnifications of 5–40× or more, recording a sufficient number of fields to achieve the desired statistical resolution of the measurement(s).

In the high throughput mode, the luminescence reader instrument 44 images the micro-array of multiple cell types at a much lower magnification of 0.2× to 1.0× magnification, providing decreased resolution, but allowing all the cell binding locations on the substrate to be recorded with a single image. In one embodiment, a 20 mm×30 mm micro-array of multiple cell types imaged at 0.5× magnification would fill a 1000×1500 array of 10 um pixels, yielding 20 um/pixel resolution, insufficient to define intracellular luminescence distributions, but sufficient to record an average response in a single well, and to count the numbers of a particular cell subtype in a well. Since typical integration times are on the order of seconds, the high throughput mode of reading technology, coupled with automated loading and handling, allows for the screening hundreds of compounds a minute.

Figure 13:
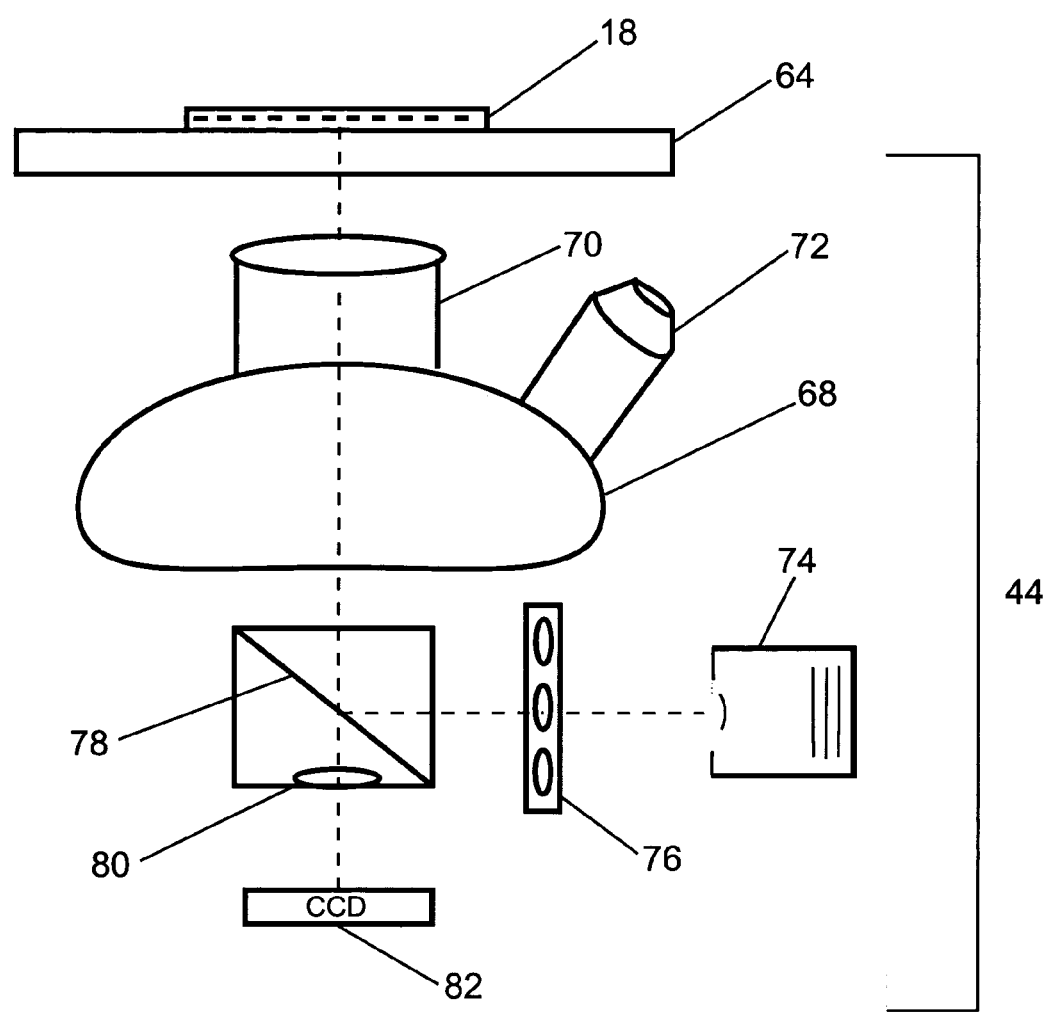
FIG. 13 is a diagram of one embodiment of the luminescence reader instrument optical system.

In one embodiment shown in FIG. 13, the luminescence reader instrument comprises an optical-mechanical design that is either an upright or inverted fluorescence microscope 44, which comprises a computer-controlled x,y,z-stage 64, a computer-controlled rotating nosepiece 68 holding a low magnification objective 70 (e.g., 0.5×) and one or more higher magnification objectives 72, a white light source lamp 74 with excitation filter wheel 76, a dichroic filter system 78 with emission filters 80, and a detector 82 (e.g., cooled charge-coupled device). For the high throughput mode, the low magnification objective 70 is moved into place and one or more luminescence images of the entire cell array is recorded. Wells that exhibit some selected luminescence response are identified and further analyzed via high content screening, wherein the nosepiece 68 is rotated to select a higher magnification objective 72 and the x,y,z-stage 64 is adjusted to center the "selected" well for both cellular and subcellular high content screening, as described in U.S. Pat. No. 5,989,835.

In an alternate embodiment, the luminescence reader instrument 44 can utilize a scanned laser beam in either confocal or standard illumination mode. Spectral selection is based on multiple laser lines or a group of separate laser diodes, as manufactured by Carl Zeiss (Jena, GmbH, Germany) or as discussed in Denk, et al. (Science 248:73, 1990).

Another embodiment of the high throughput screening mode involves the use of a low-resolution system consisting of an array (1×8, 1×12, etc.) of luminescence exciters and luminescence emission detectors that scans subsets of the wells on a non-uniform micro-patterned array of cells. In a preferred embodiment, this system consists of bundled optical fibers, but any system that directs luminescence excitation light and collects luminescence emission light from the same well will suffice. Scanning the entire micro-array of multiple cell types with this system yields the total luminescence from each well, both from cells and the solution they are bathed in. This embodiment allows for the collection of luminescence signals from cell-free systems, so-called "homogeneous" assays.

Figure 14A:
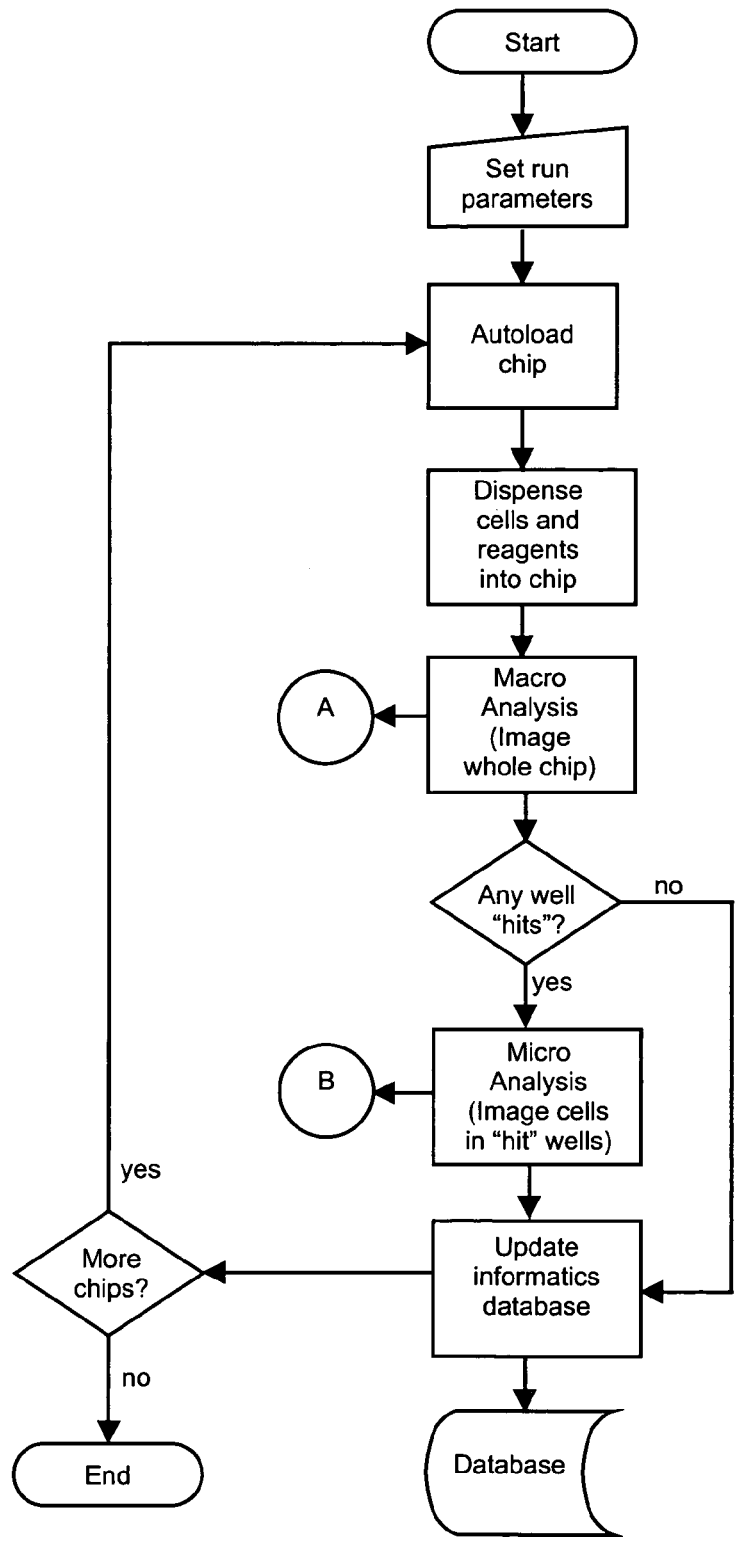
FIG. 14A is a flow chart providing an overview of the cell screening method.

FIG. 14A shows a method, in the form of a flow chart, for analyzing a micro-array of multiple cell types in both the high throughput and high content modes using the luminescence reader instrument, which first uses high throughput detection to measure a response from the entire array "A".

Figure 14B:
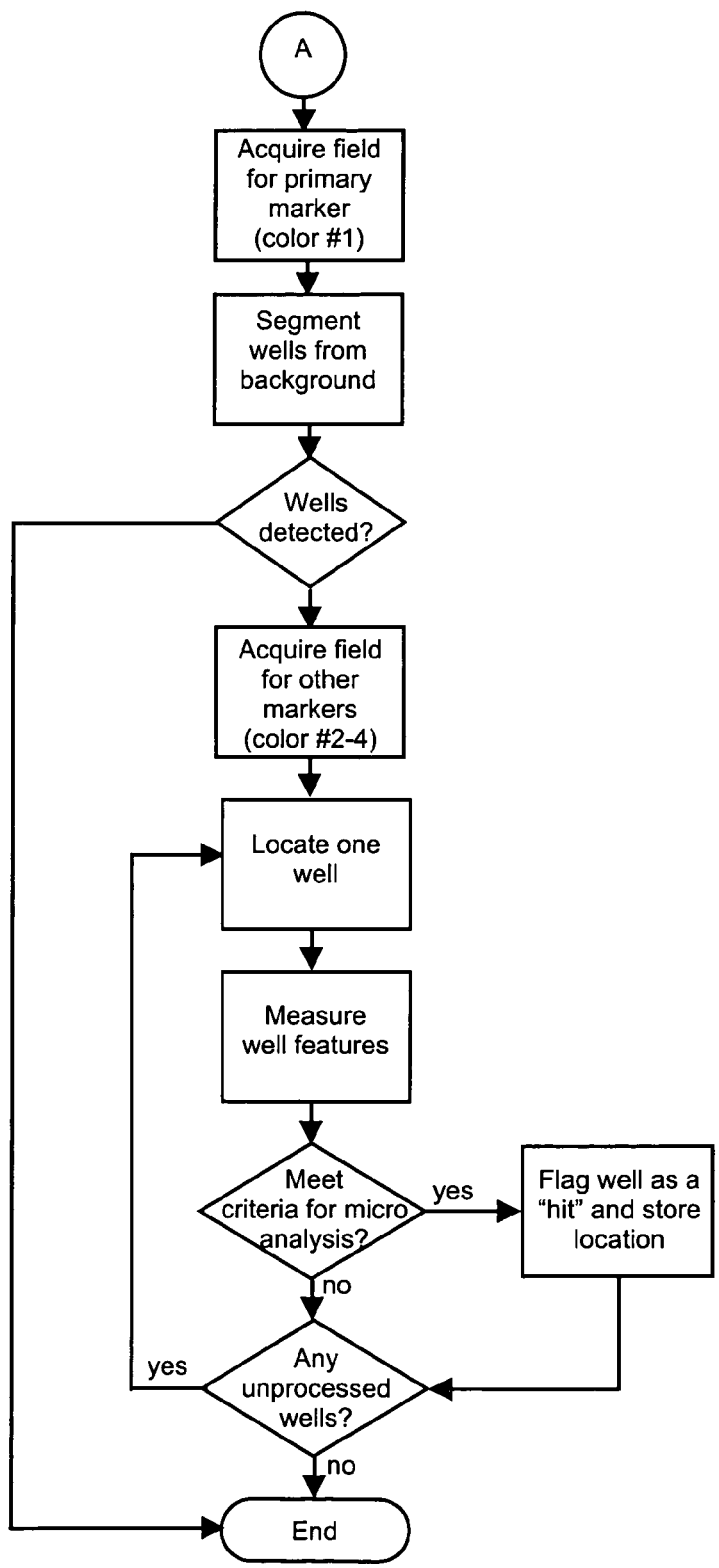
FIG. 14B is a Macro (High Throughput Mode) Processing flow chart.
Figure 14C:
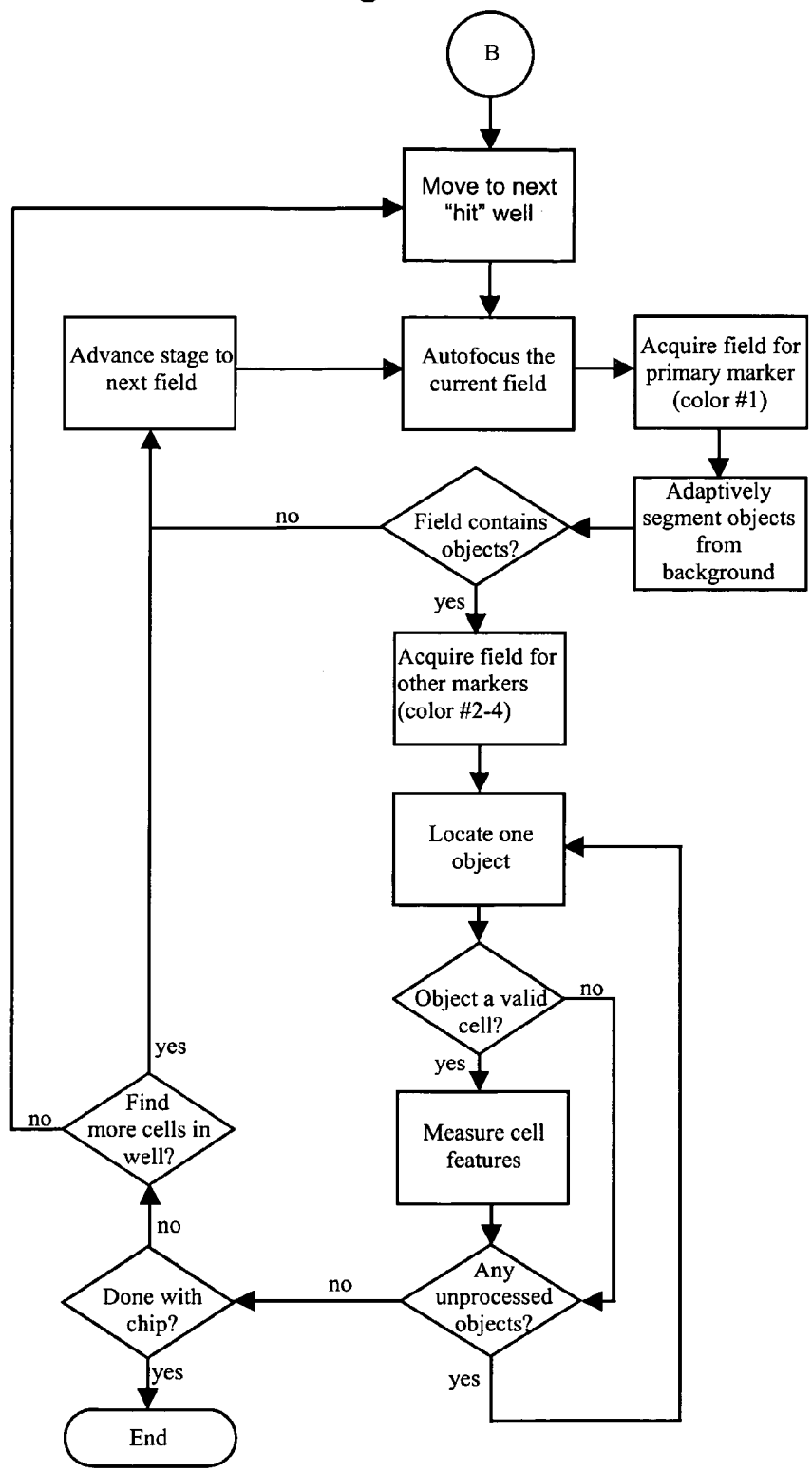
FIG. 14C is a Micro (High Content Mode) Processing flow chart.

(FIG. 14B). Any well that responds above a preset threshold is considered a hit and the cells in that well are measured via high content screening. (FIG. 14C). The high content mode ("B") may or may not measure the same cell parameter measured during the high throughput mode ("A").

In another aspect of the invention, a cell screening system is disclosed, wherein the term "screening system" comprises the integration of a luminescence reader instrument, a cassette that can be inserted into the luminescent reader instrument comprising a micro-array of multiple cell types wherein the cells contain at least one luminescent reporter molecule and a chamber associated with the non-uniform micro-patterned array of cells, a digital detector for receiving data from the luminescence reader instrument, and a computer means for receiving and processing digital data from the digital detector.

Preferred embodiments of the luminescence reader instrument, and the cassette comprising the micro-array of multiple cell types and the chamber are disclosed above. A preferred embodiment of the digital detector is disclosed in U.S. Pat. No. 5,989,835, and comprises a high resolution digital camera that acquires luminescence data from the luminescence reader instrument and converts it to digital data. In a preferred embodiment, the computer means comprises a digital cable that transports the digital signals from the digital detector to the computer, a display for user interaction and display of assay results, a means for processing assay results, and a digital storage media for data storage and archiving, as described in U.S. Pat. No. 5,989,835.

Figure 15:
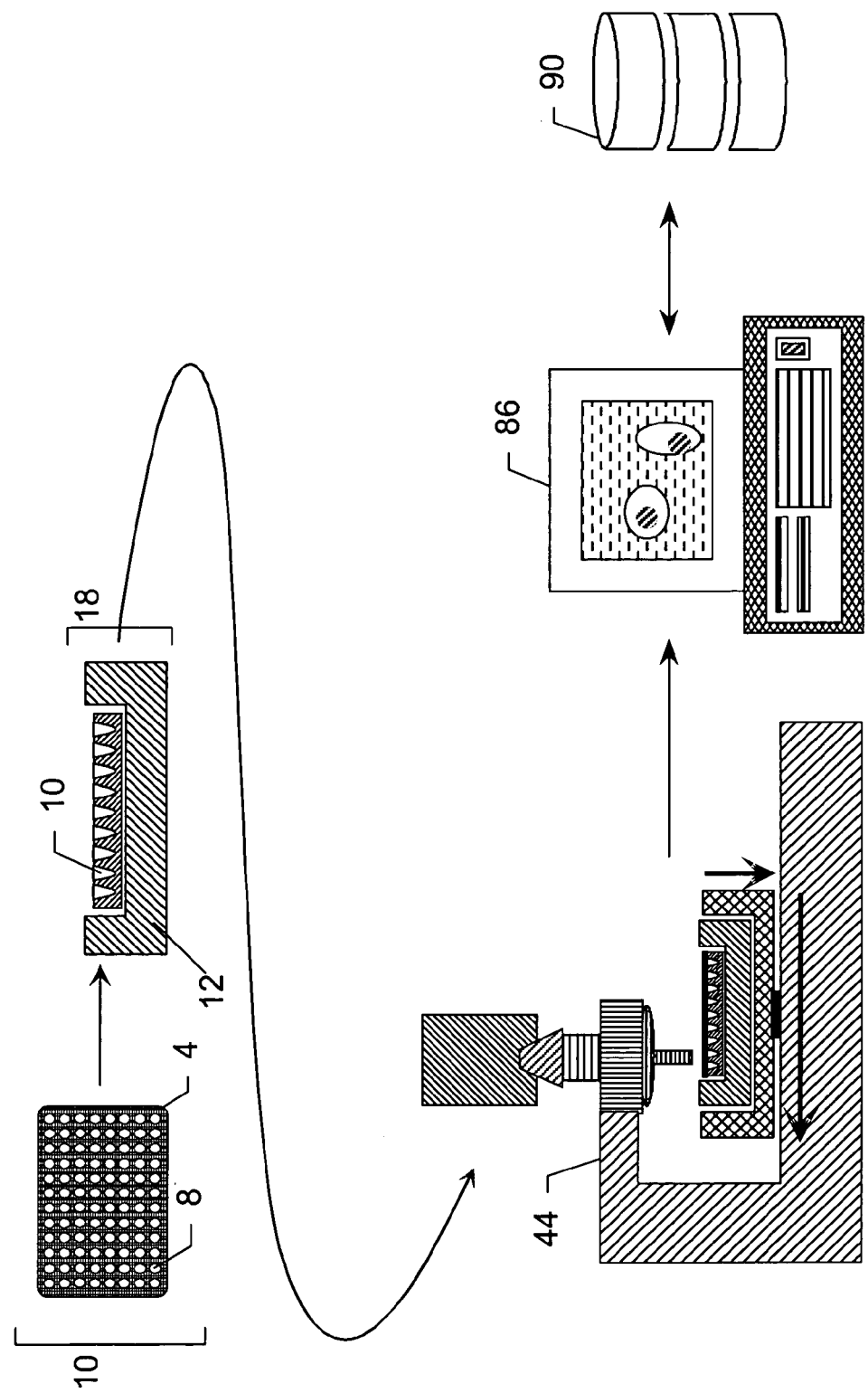
FIG. 15 is a diagram of the integrated cell screening system.
Figure 16:
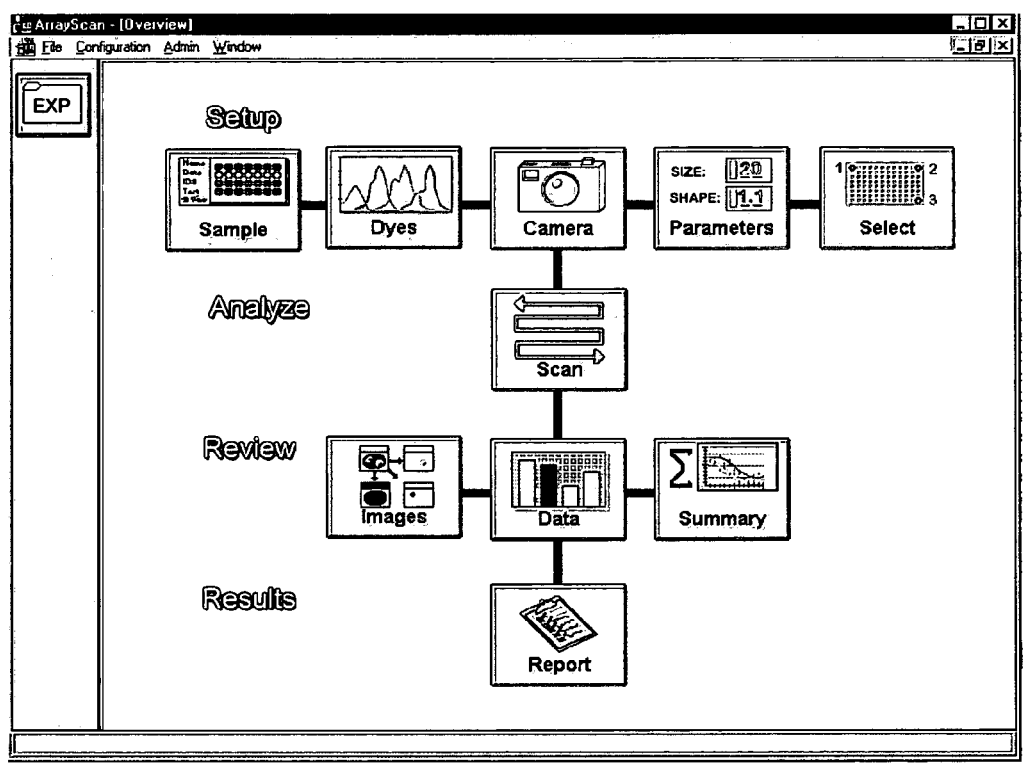
FIG. 16 is a photograph of the user interface of the luminescence reader instrument.

In a preferred embodiment, the cell screening system of the present invention comprises integration of the preferred embodiments of the elements disclosed above (FIG. 15). The array of multiple cell types 10 comprises cells bound to chemically modified cell binding locations 8 on a substrate 4. The chamber 12 serves as a microfluidic delivery system for the addition of compounds to the cells 10 on the substrate 4, and the combination of the two comprises the cassette 18. The cassette 18 is placed in a luminescence reader instrument 44. Digital data are processed as described above and in U.S. Pat. No. 5,989,835, hereby incorporated by reference in its entirety. The data can be displayed on a computer screen 86 and made part of a bioinformatics database 90, as described in U.S. Pat. No. 5,989,835. This database 90 permits storage and retrieval of data obtained through the methods of the invention, and also permits acquisition and storage of data relating to previous experiments with the cells. An example of the computer display screen is shown in FIG. 16.

EXAMPLE 1

Figure 17:
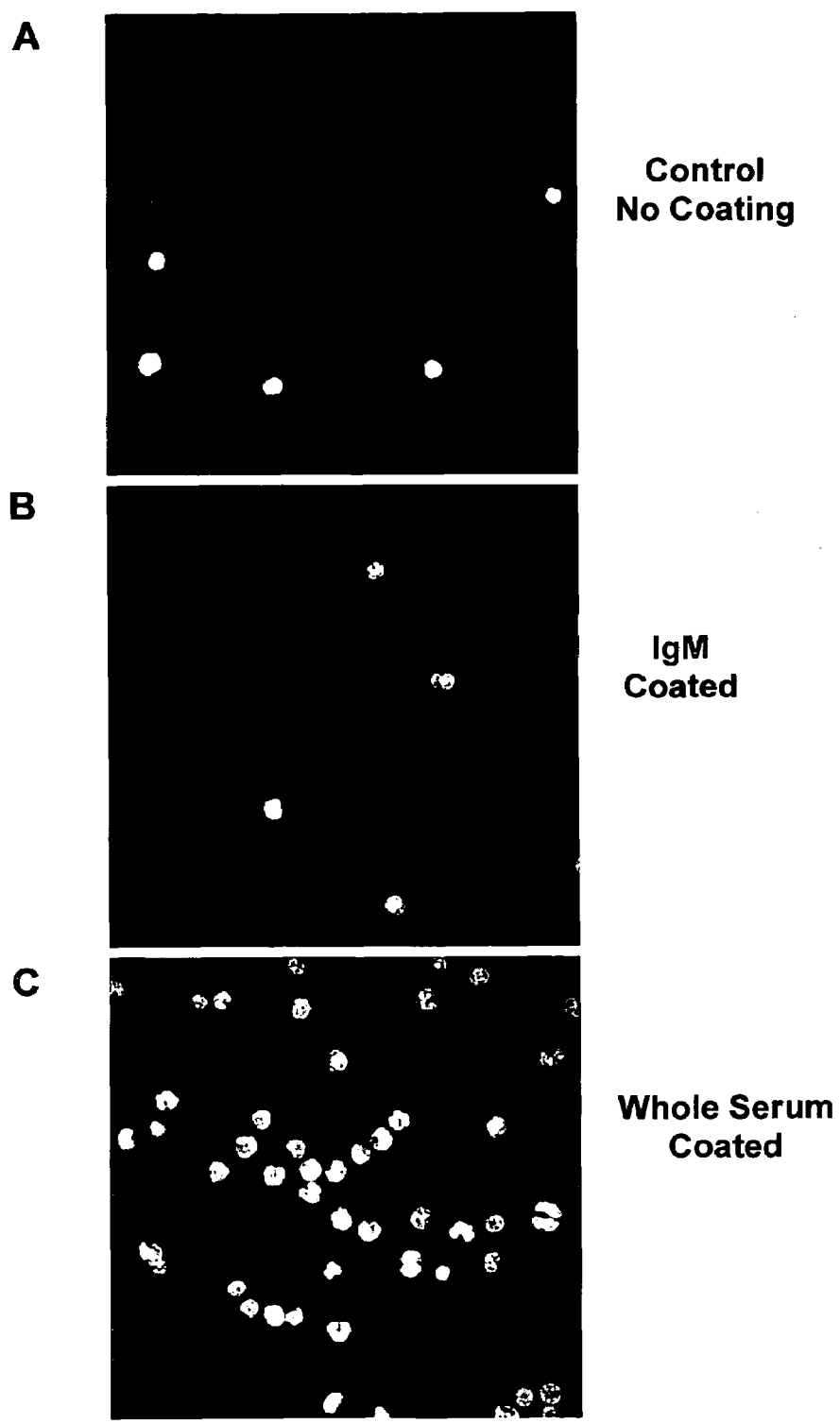
FIG. 17A is a photograph showing lymphoid cells non-specifically attached to an unmodified substrate.
FIG. 17B is a photograph showing lymphoid cells non-specifically attached to an IgM-coated substrate.
FIG. 17C is a photograph showing lymphoid cells specifically bound to a whole anti-serum-coated substrate.

Coupling of Antibodies to Micro-Array of Multiple Cell Types for the Attachment of Specific Lymphoid Cells 1. The cell line used was a mouse B cell lymphoma line (A20) that does not express IgM on its surface. A micro-array of multiple cell types was prepared for derivatization by being immersed overnight in 20% sulfuric acid, washed 2–3 times in excess distilled water, rinsed in 0.1M sodium hydroxide and blotted dry. The micro-array of multiple cell types was either used immediately or placed in a clean glass beaker and covered with parafilm for future use.
2. The micro-array of multiple cell types was placed in a 60 mm petri dish, and 3-Aminopropyltrimethoxysilane was layered onto the micro-array of multiple cell types ensuring complete coverage without running over the edges (approximately 0.2 ml for a 22×22 mm non-uniform micro-patterned array of cells, and approximately 0.5 ml for a 22×40 mm non-uniform micro-patterned array of cells). After 4 minutes at room temperature, the micro-array of multiple cell types was washed in deionized water and excess water was removed by blotting.
3. The micro-array of multiple cell types was placed in clean 60 mm petri dishes and incubated with glutaraldehyde (2.5% in PBS, approximately 2.5 ml) for 30 minutes at room temperature, followed by three PBS washes. Excess PBS was removed by blotting.
4. Cell nuclei in the micro-array of multiple cell types were labeled with a luminescent Hoechst dye during the blocking step. The appropriate number of lymphoid cells (see below) in C-DMEM were transferred to a 15 ml conical tube, and Hoechst dye was added to a final concentration of 10 µg/ml. Cells were incubated for 10–20 minutes at 37° C. in 5% $CO_2$, and then pelleted by centrifugation at 1000×g for 7 minutes at room temperature. The supernatant containing unbound Hoechst dye was removed and fresh media (C-DMEM) was added to resuspend the cells as follows: approximately $1.25–1.5\times10^5$ cells in 0.2 ml per 22×22 mm non-uniform micro-patterned array of cells, and approximately $2.5\times10^5$ cells in 0.75 ml for the 22×40 mm non-uniform micro-patterned array of cells.
5. The micro-array of multiple cell types was washed briefly in PBS and transferred to a clean, dry 60 mm petri dish, without touching the sides of the dish. Cells were carefully pipeted onto the top of the micro-array of multiple cell types at the density noted above. Dishes were incubated at 37° C. in 5% $CO_2$ for 1 hour. Unbound cells were then removed by repeated PBS washings.
6. Antibody solutions (Goat Anti-Mouse IgM or Goat Anti-Mouse Whole Serum) were spotted onto parafilm (50 µl for 22×22 mm non-uniform micro-patterned array of cells, 100 µl for a 22×40 mm non-uniform micro-patterned array of cells). The micro-array of multiple cell types was inverted onto the spots, so that the antiserum covered the entire surface of the treated micro-array of multiple cell types without trapping air bubbles. The micro-array of multiple cell types was incubated with the antibody solution for 1 hour at room temperature.
7. The micro-array of multiple cell types was carefully lifted from the parafilm, placed in a clean 60 mm petri dish, and washed three times with PBS. Unreacted sites are then blocked by the addition of 2.5 ml of 10% serum (calf or fetal calf serum in DMEM or Hank's Balanced Salt Solution) for 1 hour at room temperature.
8. Both cell lines should bind to the anti-mouse whole serum, but only the X16s should bind to the anti-mouse IgM. The binding of specific lymphoid cell strains to the chemically modified surface is shown in FIG. 17. The mouse lymphoid A20 cell line, lacking surface IgM molecules but displaying IgG molecules, bound much more strongly to the surface modified with whole goat anti-mouse serum (FIG. 17C) than to the surface modified with goat anti-mouse IgM (FIG. 17B) or an uncoated slide (FIG. 17A).

EXAMPLE 2

High-Content and High Throughput Screen

The insulin-dependent stimulation of glucose uptake into cells such as adipocytes and myocytes requires a complex orchestration of cytoplasmic processes that result in the translocation of GLUT4 glucose transporters from an intracellular compartment to the plasma membrane. A number of molecular events are triggered by insulin binding to its receptor, including direct signal transduction events and indirect processes such as the cytoskeletal reorganizations required for the translocation process. Because the actin-cytoskeleton plays an important role in cytoplasmic organization, intracellular signaling ions and molecules that regulate this living gel can also be considered as intermediates of GLUT4 translocation.

A two level screen for insulin mimetics is implemented as follows. Cells carrying a stable chimera of GLUT4 with a Blue Fluorescent Protein (BFP) are arranged on the micro-array of multiple cell types arrays, and then loaded with the acetoxymethylester form of Fluo-3, a calcium indicator (green fluorescence). The array of locations are then simultaneously treated with an array of compounds using the microfluidic delivery system, and a short sequence of Fluo-3 images of the whole micro-array of multiple cell types are analyzed for wells exhibiting a calcium response in the high throughput mode. The wells containing compounds that induced a response, are then analyzed on a cell by cell basis for evidence of GLUT4 translocation to the plasma membrane (i.e., the high-content mode) using blue fluorescence detected in time and space.

Figure 18:
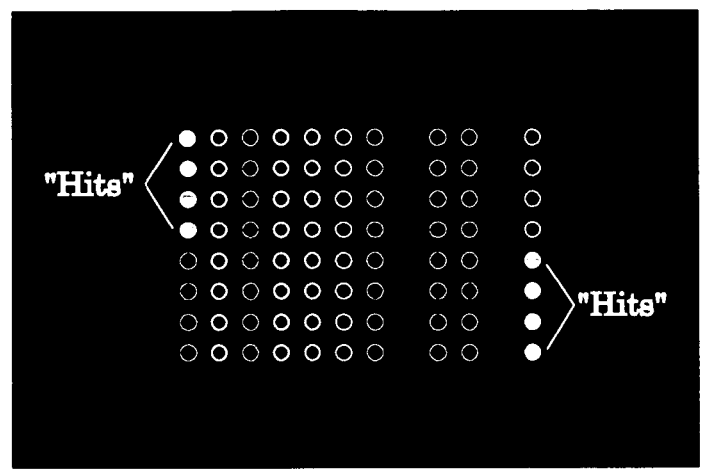
FIG. 18A is a photographic image from High Throughput Mode of luminescence reader instrument identifying "hits".
FIG. 18B is a series of photographic images showing the high content mode identifying high content biological information.
Figure 18:
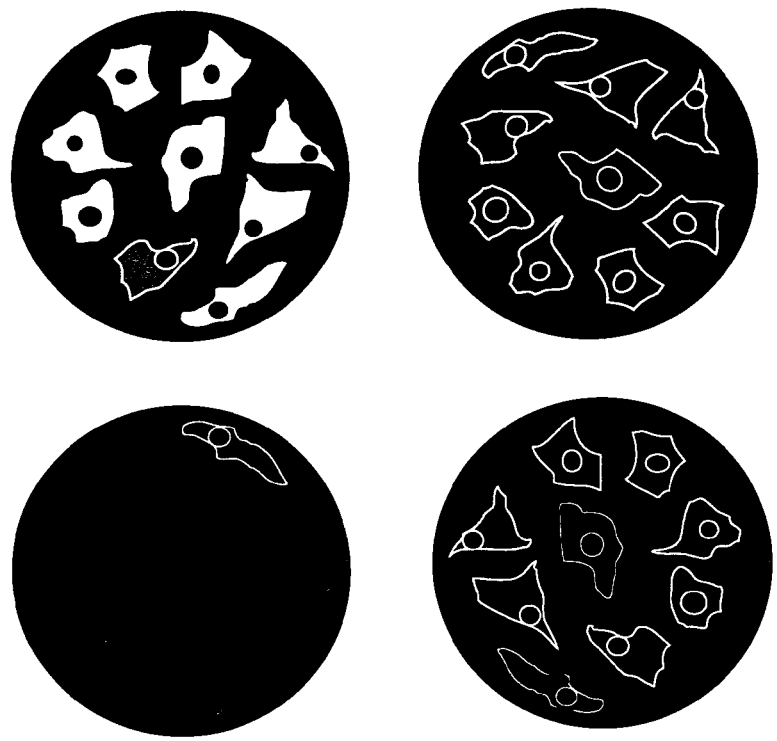
Figure 19:
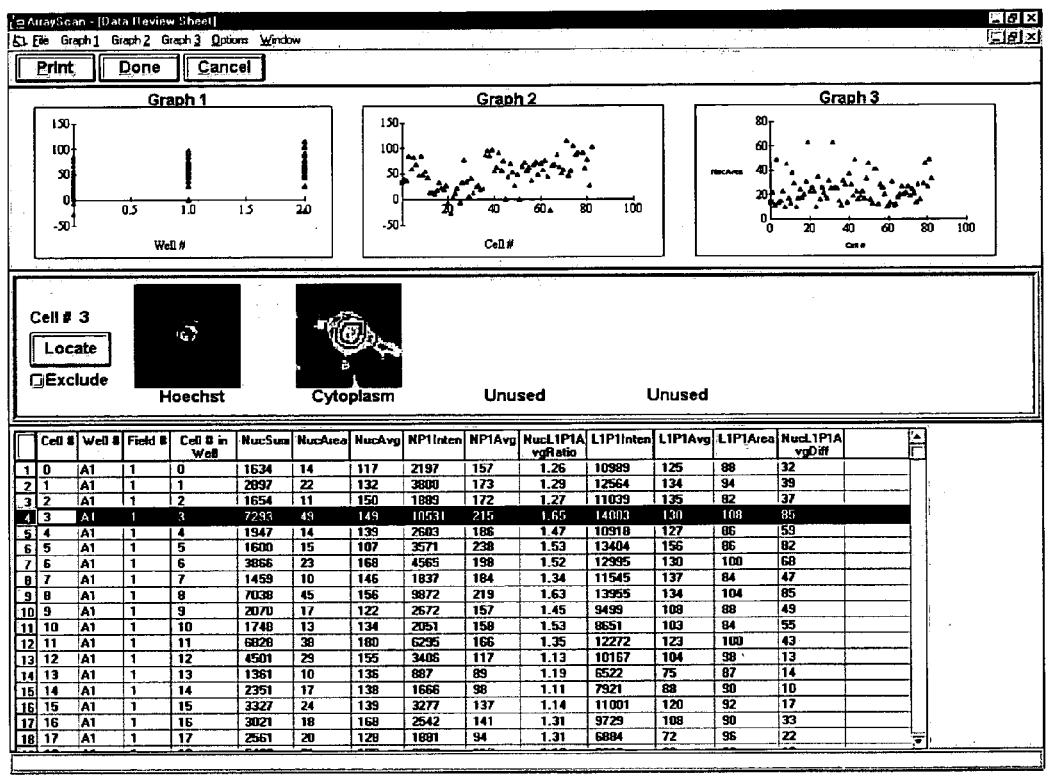
FIG. 19 is a photographic image showing the display of cell data gathered from the high content mode.

FIG. 18 depicts the sequential images of the whole micro-array of multiple cell types in the high throughput mode (FIG. 18A) and the high content mode (FIG. 18B). FIG. 19 shows the cell data from the high content mode.

EXAMPLE 3

Improved Cassettes and Enhanced Well Density

In another aspect, the present invention provides devices and methods for maximizing the cell-plated area and the number of wells that can be imaged in a sub-array, while still obtaining adequate pixel resolution in the image. This result has been achieved through the use of fluidic architectures that minimize the distance and area between wells, thus maximizing well density.

In one embodiment of this aspect is provided a cassette for cell screening comprising a substrate having a surface, wherein the surface contains a plurality of cell binding locations; a fluid delivery system for delivering reagents to the plurality of cell binding locations, wherein the fluid delivery system comprises a multi-level chamber that mates with the substrate, wherein the multi-level chamber comprises i. a crossed array of microfluidic input channels and output channels, wherein each well is in fluid connection with one or more input channels and one or more output channels;
ii. a plurality of fluidic locations in fluid connection with the microfluidic input channels and output channels;
iii. one or more input manifolds in fluid connection with the microfluidic input channels;
iv. one or more output manifolds in fluid connection with the microfluidic output channels;
v. at least one source receptacle in fluid connection with the one or more input manifolds; and
vi. at least one waste receptacle in fluid connection with one or more output manifolds; and
a plurality of wells, wherein an individual well comprises the space defined by the mating of one cell binding location and one fluidic location.

In preferred embodiments, the cassettes further comprise a pump to control fluid flow within the microfluidic device; a substrate temperature controller and/or a controller to regulate oxygen and carbon dioxide partial pressures within the device.

The substrate of the present invention is chemically modified so that cells selectively adhere to a cell growth substrate and are contained within small regions, referred to as "cell binding locations", which are sub-millimeter to a few millimeters in size. The combination of a cell binding location on the substrate and a fluidic location on the chamber defines a space referred to as a "well". The substrate may be predominantly flat and the cell binding locations may be matched with fluidic location depressions on a substrate cover, so that when the two parts are assembled there is some depth in the area of the wells so formed. Conversely, the substrate cover fluidic location may be flat and the substrate may contain depressions at the cell binding location, so that when the two parts are assembled there is some depth in the area of the wells so formed. Fluids and test compounds are supplied to the wells via a chamber, which combines with the substrate to form a cassette. In a preferred embodiment, the chamber acts as the substrate cover and contains fluidic locations in fluid connection with the microfluidic channels of the device, wherein the fluidic locations comprise depressions that match the cell binding locations on the substrate, such that the volume of each well is etched into the chamber.

On the surface of the substrate, there are sealing regions that lie between and around the cell binding locations, and there are corresponding sealing regions on the bottom face of the chamber that lie between and around the fluidic locations. When the substrate and the chamber are joined, the sealing regions of both components meet to form a seal that prevents the flow of fluid across the sealing regions between the wells thereby formed. These sealing regions of both components may be physically and/or chemically modified to enhance sealing. In a first example, a hydrophobic silane coating of octadecyltrichlorosilane is coated on the sealing regions. In a second example, light-curable adhesives and cyanoacrylates that are USP Class IV-compliant such as are available from Dymax Corporation are amenable to use with biomedical devices made from ceramic, glass, plastic, or metal. In a third example, a biocompatible tape material with precision cut-outs that match the wells of the array is available from Avery Dennison Specialty Tape Division. Similarly, biomedical acrylic adhesives can be transferred from tapes to surfaces, such as are available from Tyco Corporation, for applying an adhesive coating precisely to these sealing regions. In a fourth example, a light-curable silicone elastomer can be used for bonding and sealing between the sealing regions of the substrate and the chamber, such as are available from Master Bond, Inc.

Figure 20:
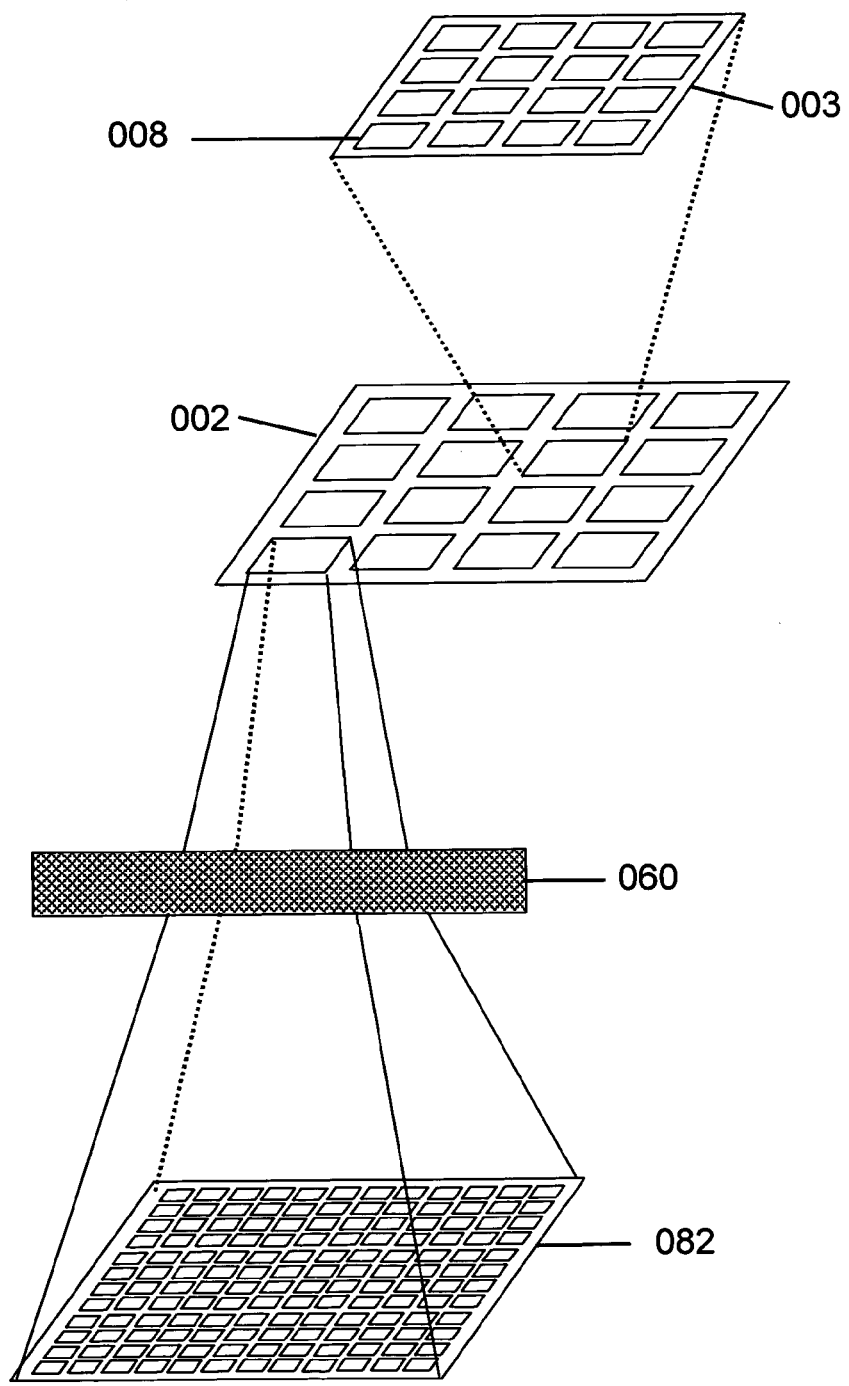
FIG. 20 depicts the optimization of cell imaging by simultaneous imaging of a sub-array of cell binding locations of the whole array. There is a one to one correspondence between the array of cell binding locations on the substrate, the array of fluidic locations on the chamber, and the array of wells formed by the joining of the two.

The microfluidic cassette of the present invention has advantages over prior art cell array microfluidic devices used in high content screening systems including, but not limited to:

1) faster imaging of a statistically-relevant set of cells (based on imaging a set of cell binding locations (i.e.: "sub-arrays") simultaneously; See FIG. 20)
2) more wells per plate and less physical space occupied per plate (i.e.: higher well density),
3) more efficient use of valuable test compounds, and
4) more efficient use of cells compared to microplates in which the entire well area is not imaged.

As discussed supra, prior microwell plate fluid exchange for each well can only be achieved by means of a pipette being inserted into the well and either ejecting or aspirating fluid to or from the well, respectively. Automated fluid handling in prior microwell plates is acheived by using robotic pipettors that insert a pipette into each well for each fluid transfer step in a procedure. This pipette is typically required also to move to or from another microplate well for the source or destination of the fluid that is exchanged with the microwell plate of interest.

Integrated fluidics is advantageous for arrays with sub-millimeter inter-well distances because it is unwieldy, if not impossible, to pipette fluids with an acceptable degree of spatial resolution and accuracy. An acceptable level of accuracy requires that the measurement error should not exceed 2%. Thus, for a 100 microliter ($\mu$l) volume in the well of a 96 well plate, a measurement error of 2 $\mu$l is acceptable. For a 100 nano-liter (nl) volume, a 2 nl measurement error would be required. This level of accuracy is not reliably available with prior automatic pipettors across a spectrum of compositions and viscosities.

The minimization of the inter-well distances enables the fast parallel reading of sub-arrays of wells. If the integrated fluidics is too bulky (i.e.: does not allow close-spacing of wells), then such fast parallel reading capability is lost. In a preferred embodiment of the present invention, a crossed channel architecture is utilized, allowing for fewer channels, valves, and pumps, and thereby further reducing the space taken by channels on the cassette of the invention. In a most preferred embodiment, the channels are placed in levels above that of the wells, permitting the closest possible inter-well spacing. In a further preferred embodiment, the use of porous medium as a drain 'pump' allows for simpler design and fabrication of the system. According to the invention, the channels may be of any size that permits the fluidic architecture herein defined. In a preferred embodiment, they range in size from between about 0.025 mm to about 0.5 mm in width for square cross-section channels, or in diameter for circular cross-section channels.

Figure 40:
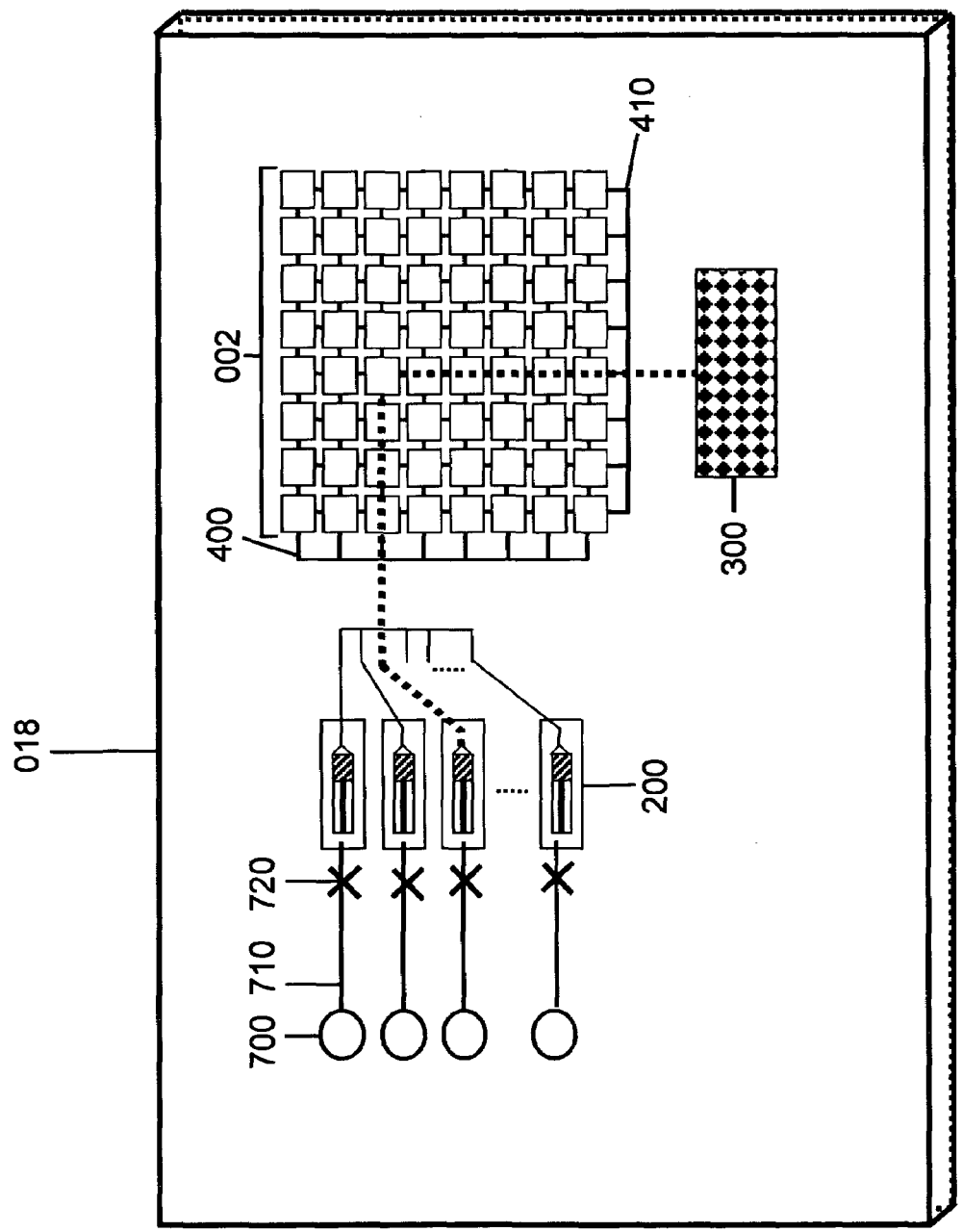
FIG. 40 shows one embodiment of the pumping and valving schemes of this invention as it would appear with all the pumps and valves on-board the cassette.

The fluidic architecture of the instant microfluidic cassette enables the controlling elements (including, but not limited to pumps, manifolds, controlled-pressure vessels, and/or valves) to be located outside the matrix of the cell array. FIG. 40 shows one embodiment of the pumping and valving schemes of this invention as it would appear with all the pumps and valves on-board the cassette. All variations of the pumping and valving schemes shown in various Figures (and others that would be apparent to those skilled in the art) may be implemented in this way, either with on-board active devices outside the matrix of the wells, with off-board active devices, or with some devices on-board and some devices off-board. As a result, the controlling elements can be either within the cassette (on-board) or external to the cassette (off-board). In either case, there are no active components within the matrix of the array of wells that might limit the close-spacing of channels and wells. Because this cassette is particularly designed for the culture and analysis of living cells, the fluidic architecture and all of its sub-components and functional parts are compatible with, support, and enable the culture of living cells. The particular aspects of these sub-components and functional parts that are designed for live cell culture are identified below.

In a preferred embodiment, the cassette of the present invention comprises an off-board pump to provide pressure-driven flow that also controls which wells are addressed by the flow. This design feature ensures that the pumping method, unlike many prior art methods, is not ineffective or harmful when used with cell culture medium that is aqueous, polar and contains proteins and salts. For example, electrohydrodynamic pumping is ineffective with polar solvents (Marc Madou, Fundamentals of Microfabrication, CRC Press, Boca Raton, 1997, p. 433). Electro-osmosis is typically accompanied by some degree of electrophoretic separation of charged medium components, such as proteins. Also, electro-osmosis typically requires the use of electric field strengths within the range of 100 V/cm to 1000 V/cm, which may affect the physiology of the living cells in the device. The fluid control system of the present device does not suffer from the disadvantages of electrically-induced methods when using biological fluids.

Figure 41:
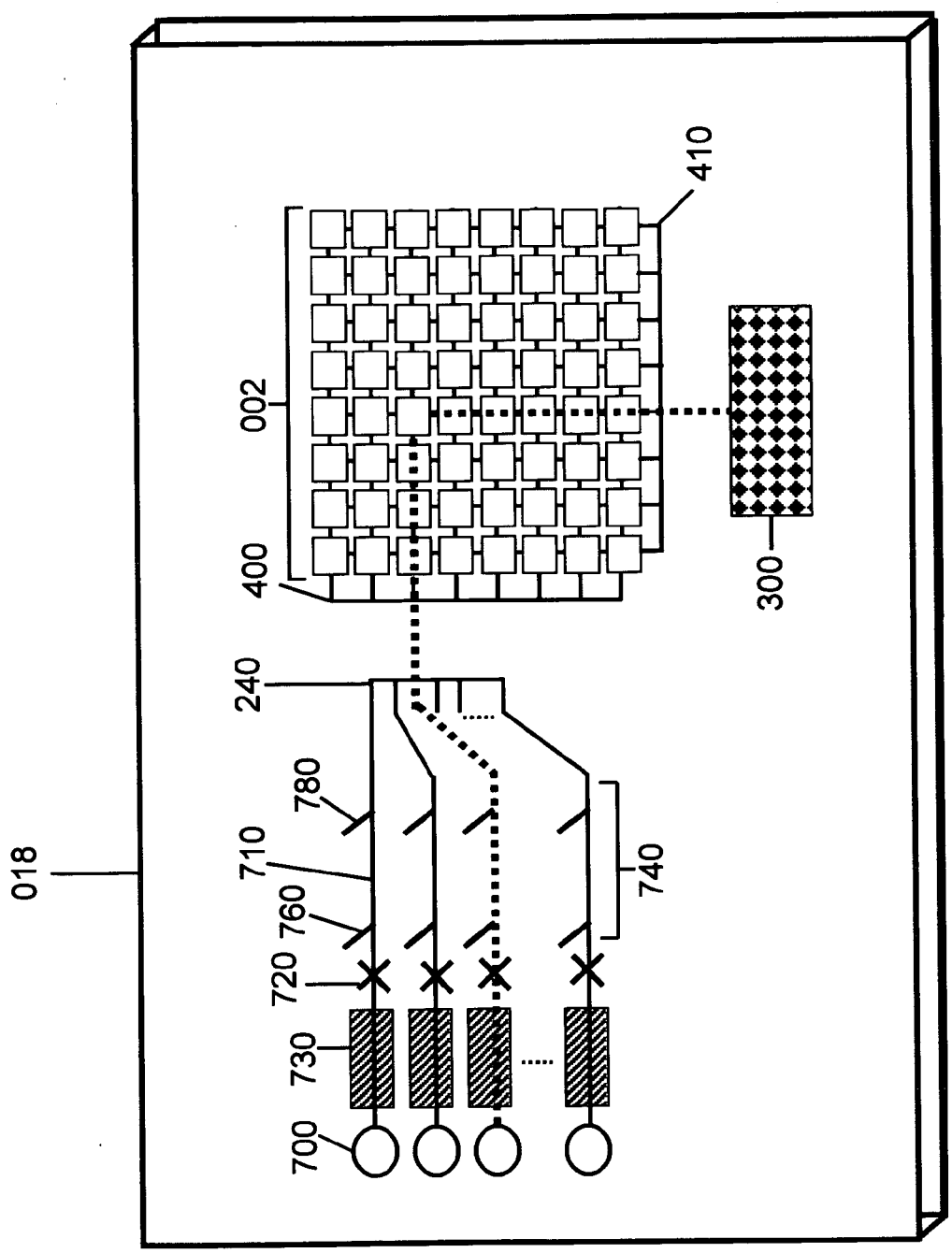
FIG. 41 shows an embodiment, wherein the pumps are on-board and utilize electrically-driven flow, where the electric fields are limited to regions external to the matrix of the array of wells, and minimal or no electric field gradients are applied across any of the wells in which live cells are present.
Figure 42:
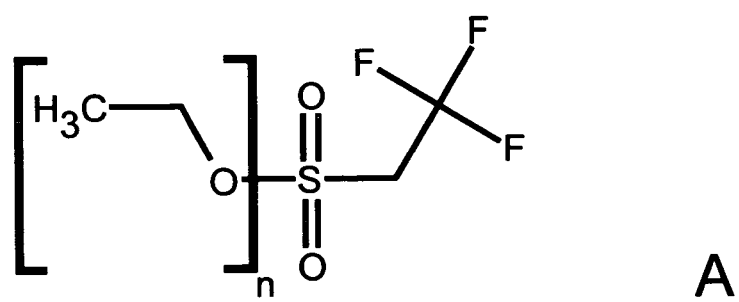
FIG. 42(a) The standard structure of tresyl-PEG, wherein "n" can equal any number. (b) The structure of trimethoxysilylpropyldiethylenetriamine.
Figure 42:
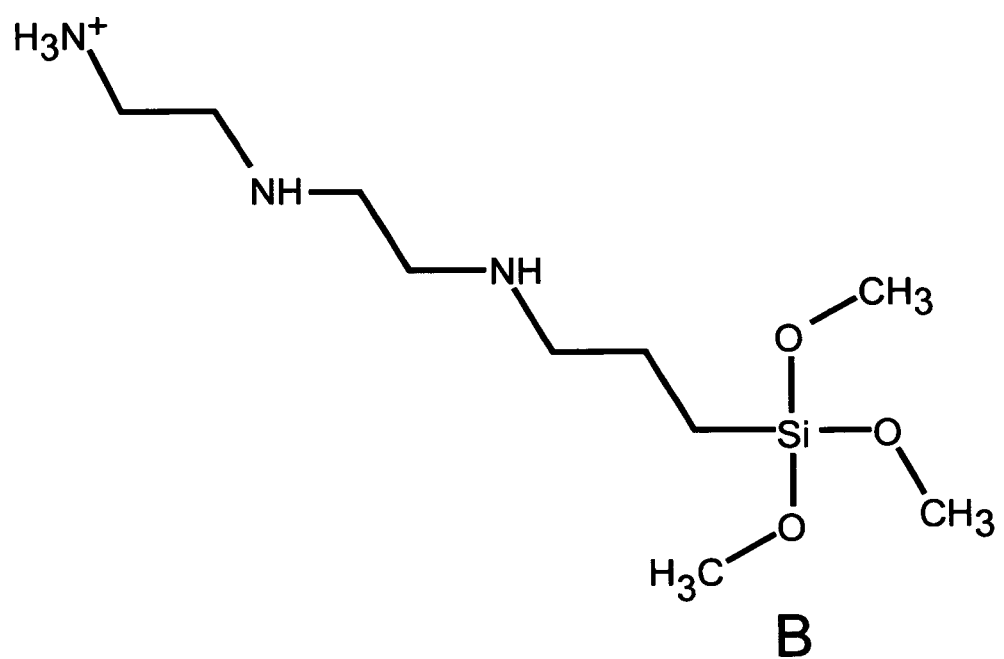
Figure 43:
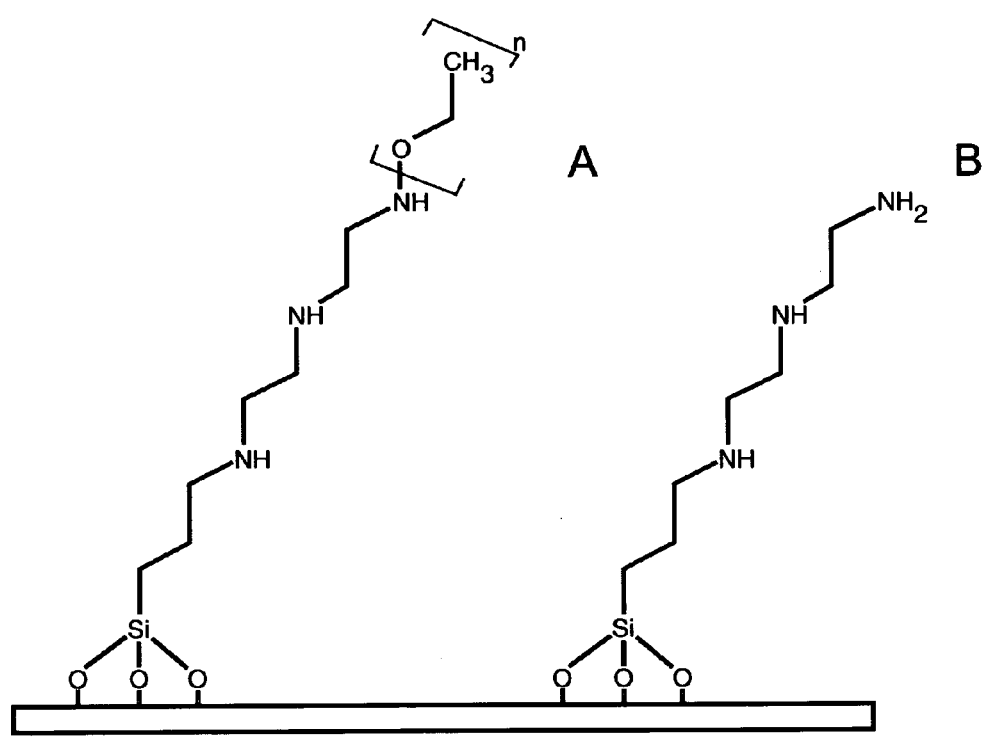
FIG. 43(a) An example of an amine-PEG surface product. (b) An example of a surface amine.
Figure 44:
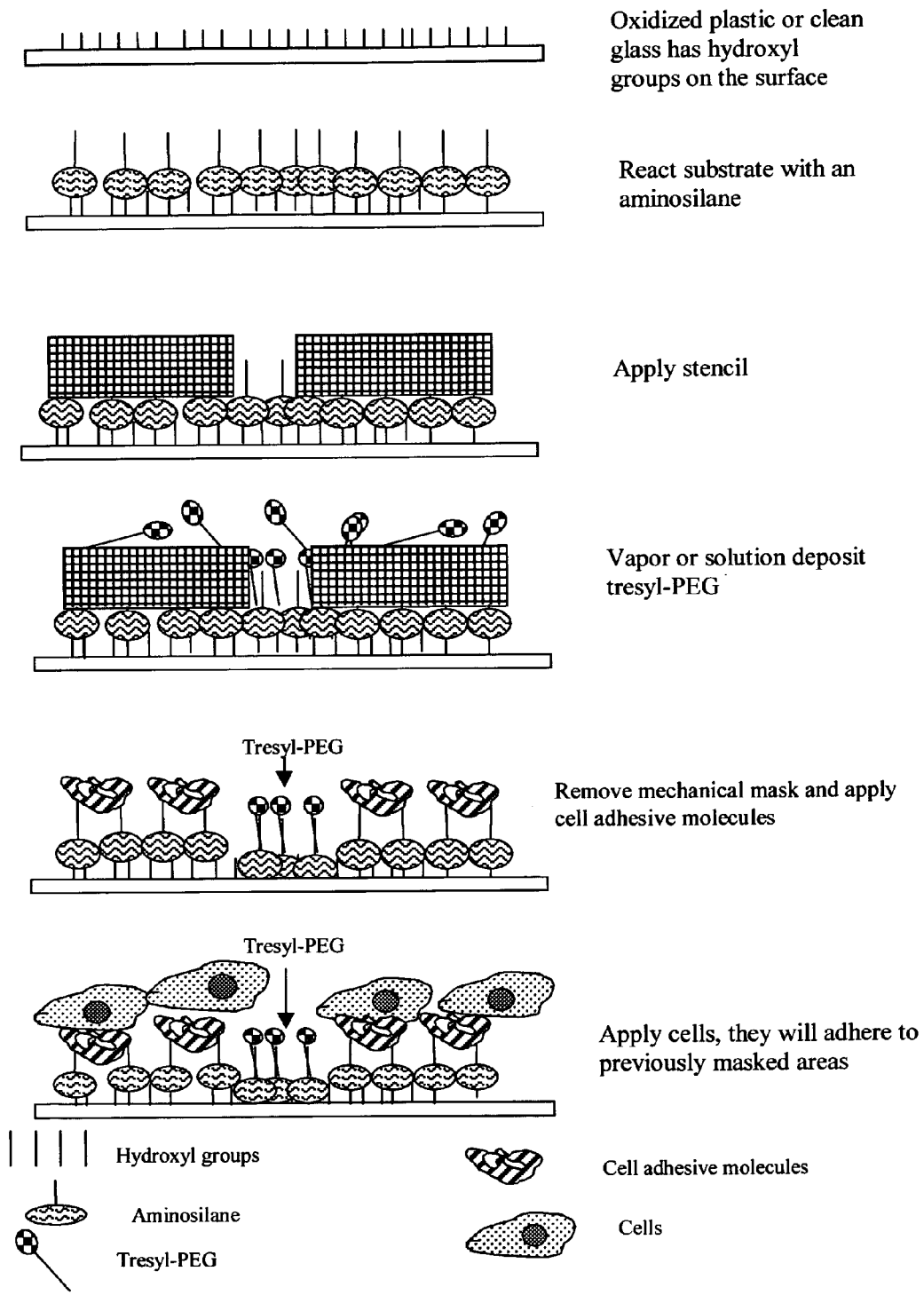
FIG. 44 is a most preferred embodiment for achieving selective positioning of cell adhesive molecules and cell repulsive moieties.
Figure 45:
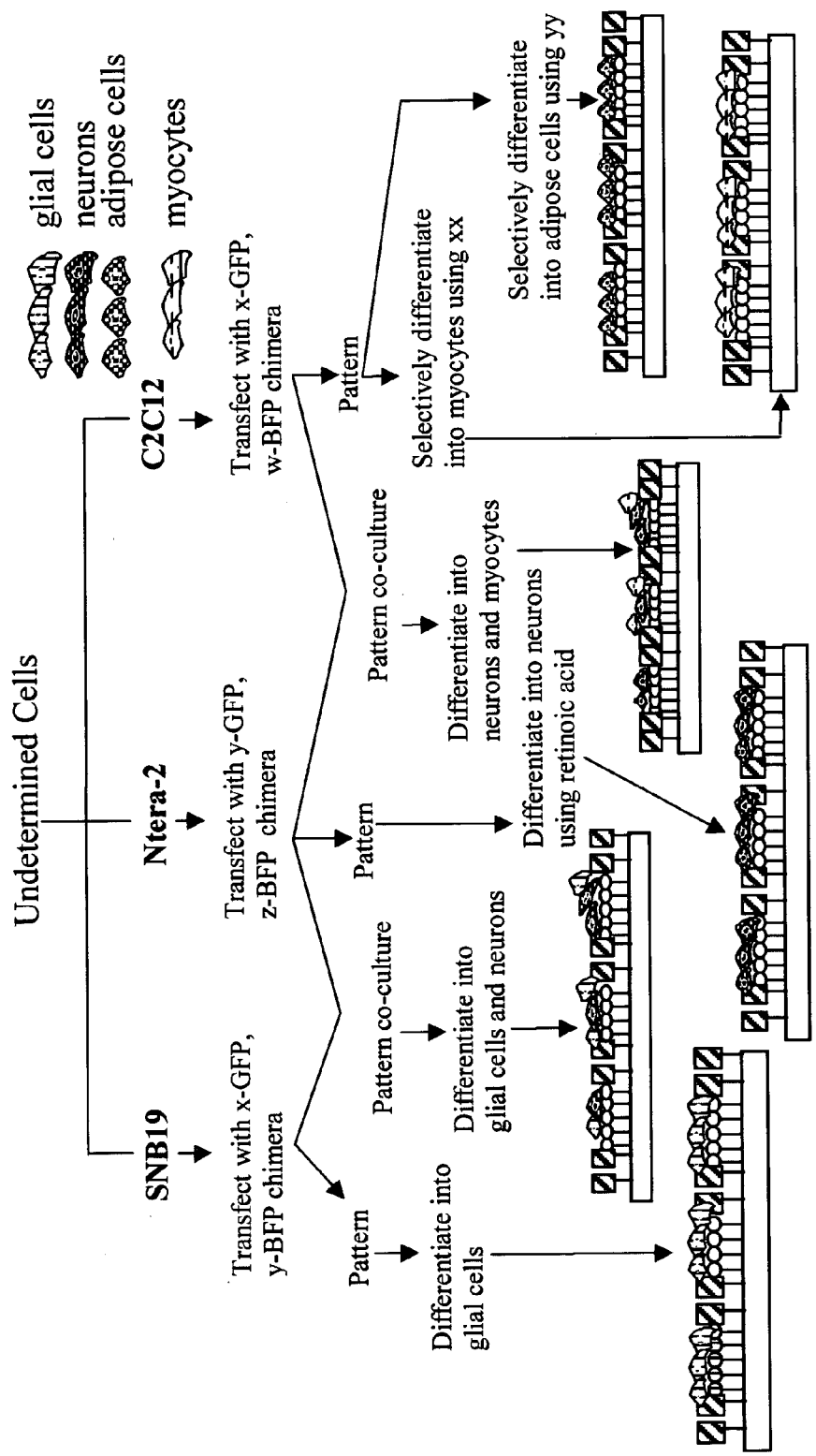
FIG. 45 is an experimental flowchart for selective differentiation of stem cells on a substrate to produce both tissue-specific and organ-specific cell substrates.

In another embodiment, the pump is on-board and may utilize electrically-driven flow, but the electric fields are limited to regions external to the matrix of the array of wells, and no electric field gradients are applied across any of the wells in which live cells are present. This embodiment is shown in FIG. 41, where two electrodes are used to apply electric potential differences along segments of fluidic channels corresponding to different on-board source reservoirs (730). Each channel segment with its electrode pair form an electrokinetic pump (740). These source reservoirs (730) may be supplied with media and/or compounds via fill ports (700) in the cassette surface. Valves (720) between the reservoirs and the pumps are closed whenever the corresponding electrokinetic pump is off, and are open whenever the corresponding electrokinetic pump is on, to maintain back pressure and to allow intake of air or fluid, respectively. Control of the voltage applied to electrode 1 (760) is used to induce electrokinetic flow of the fluid in the corresponding channel segment. Electrode 2 (780) (nearest to the matrix of wells) is kept at ground potential, as is the matrix of the wells, to ensure that minimal or no potential difference and/or electric field is developed in the vicinity of the cells, because electric fields are known to affect cell physiology. Alternatively, the electrokinetic pump may be located downstream from the array to serve as a negative pressure pump. In this embodiment, electrophoresis of the media by the pumping action, if any, would only affect the media after it has been already used by the cells and is on its way to the waste reservoir.

In all embodiments, the use of on-board or off-board pumps that are external to the matrix of wells to control fluid flow eliminates the need for active valves within the matrix of wells, and thus eliminates the problem of allocating space within the matrix that might prevent the close spacing of the wells.

The control of the fluid pathway by means of pressure control also enables the optional use of various diffusion control means that are compatible and effective with cell culture medium that is aqueous, polar and contains proteins and salts. These means also require minimal space on the device, and thus do not prevent the close-spacing of wells.

U.S. Pat. No. 5,603,351 describes a microfluidic device that includes crossed channels, but the channel network is not defined to allow two or more reagents to be combined in a reaction well, but rather to allow reagents to be fed to a well in a serial fashion. The purpose of the present cassette is not to expose two or more different fluids to each other, but to expose the living cells cultured on the well bottoms in serial fashion to two or more different fluids.

Figure 21:
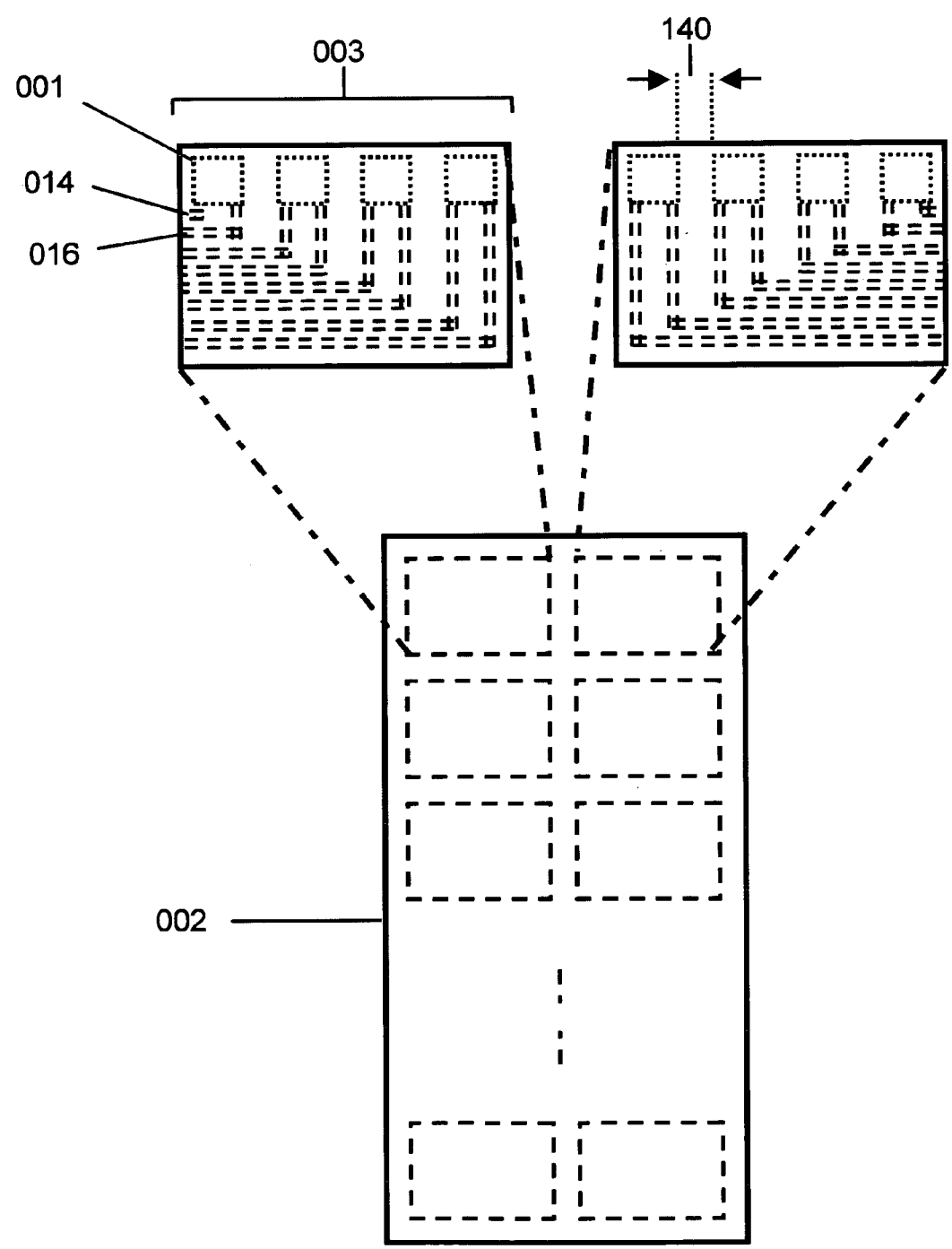
FIG. 21 exemplifies an 8×8 array (64 wells, 128 channels) of the microfluidic device wherein each fluidic location is provided with a separate input and output channel, yielding $2n^2$ channels for an n×n array.
Figure 22:
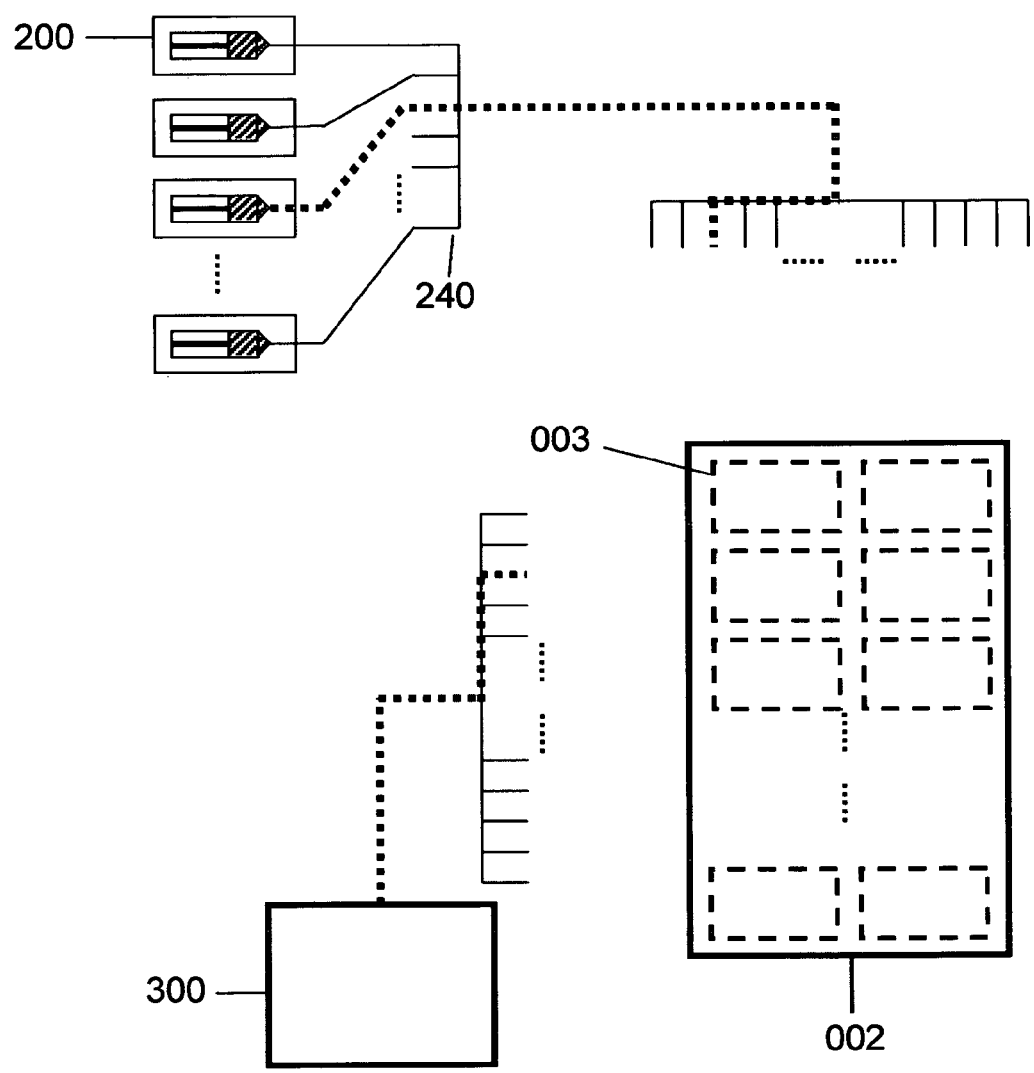
FIG. 22 depicts the microfluidic device of FIG. 21 wherein $m+n^2$ valves or pumps are utilized to control the flow of m liquid or vapor mixtures to an 8×8 array.
Figure 23:
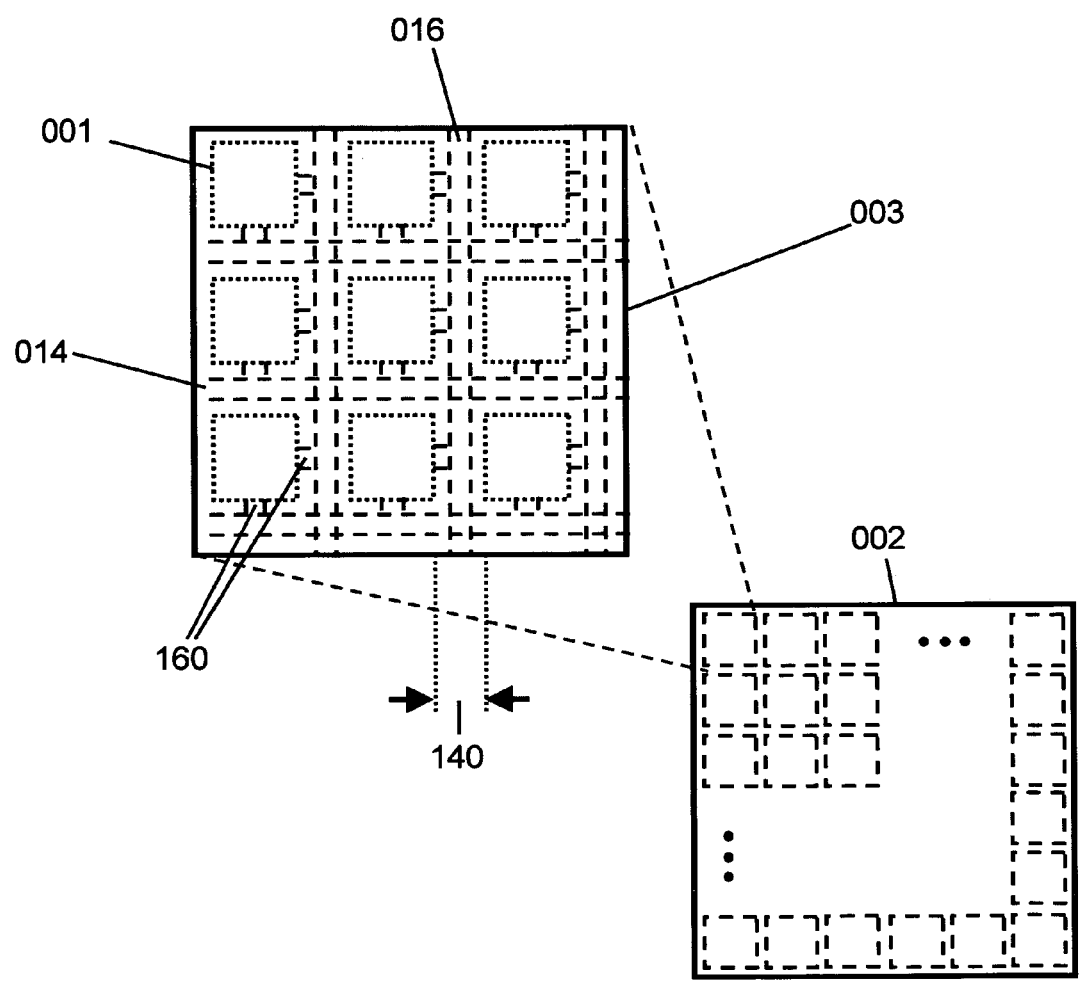
FIG. 23 depicts an embodiment of the microfluidic device wherein the fluid delivery system consists of a crossed, nonintersecting array of input and output channels, and horizontal connecting channels utilizing multiple levels, and wherein the two layers lie in the same plane of the well layer.
Figure 24:
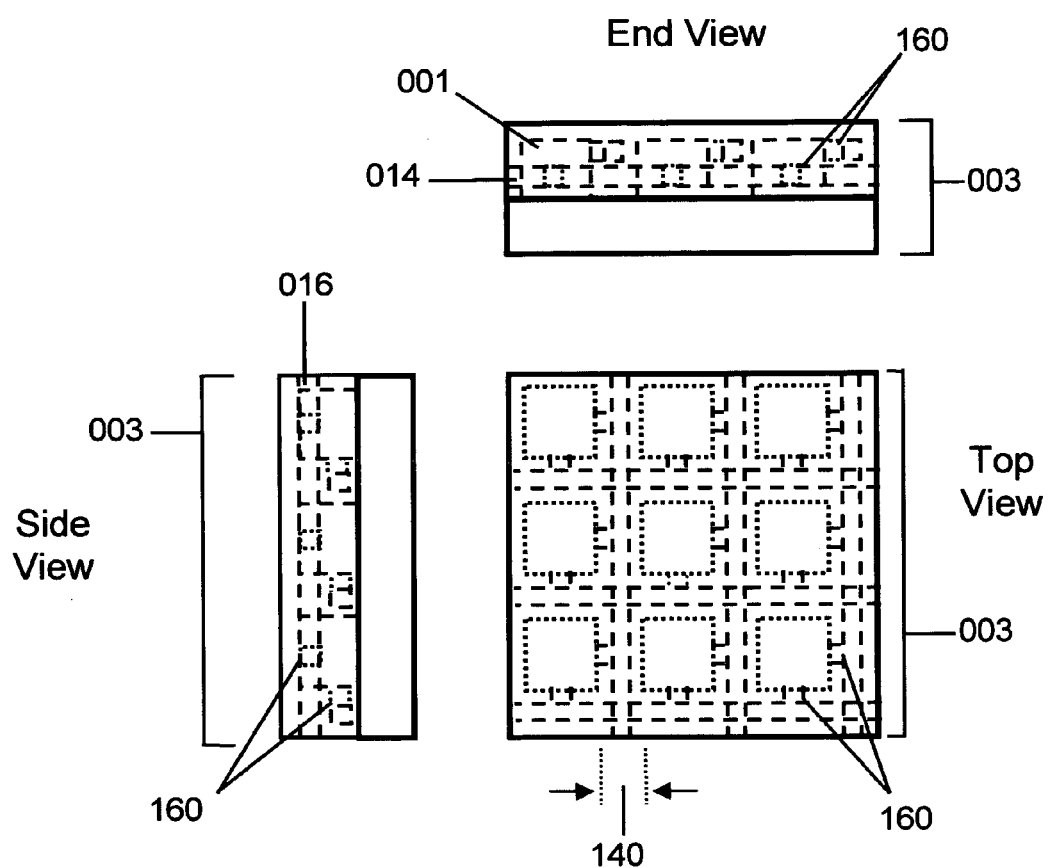
FIG. 24 depicts an end view and side view of the embodiment of FIG. 23.
Figure 25:
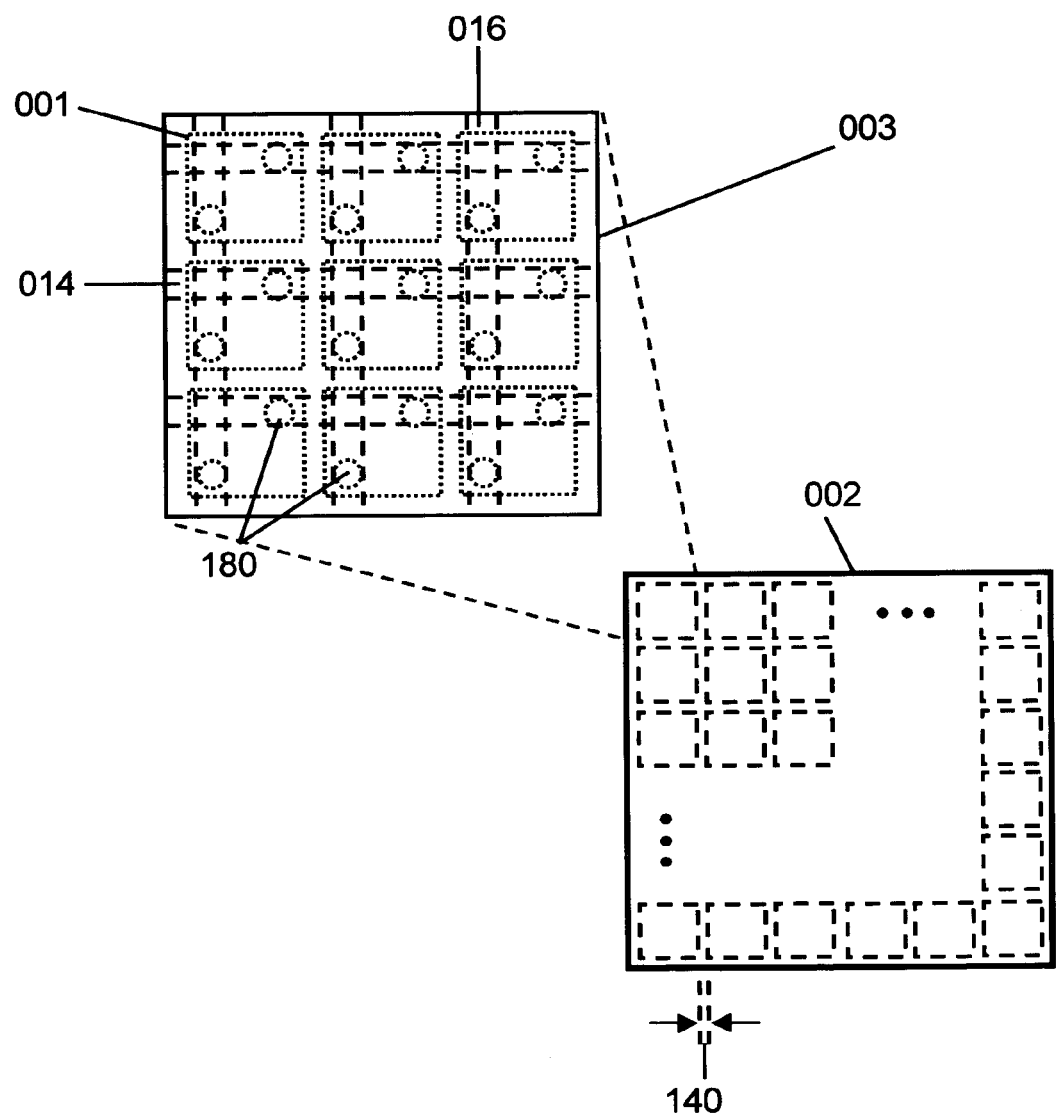
FIG. 25 depicts an embodiment of the microfluidic device wherein the fluid delivery system consists of a crossed, nonintersecting array of input and output channels, and vertical connecting channels utilizing multiple levels, and wherein the two layers lie in a plane above that of the well layer.
Figure 26:
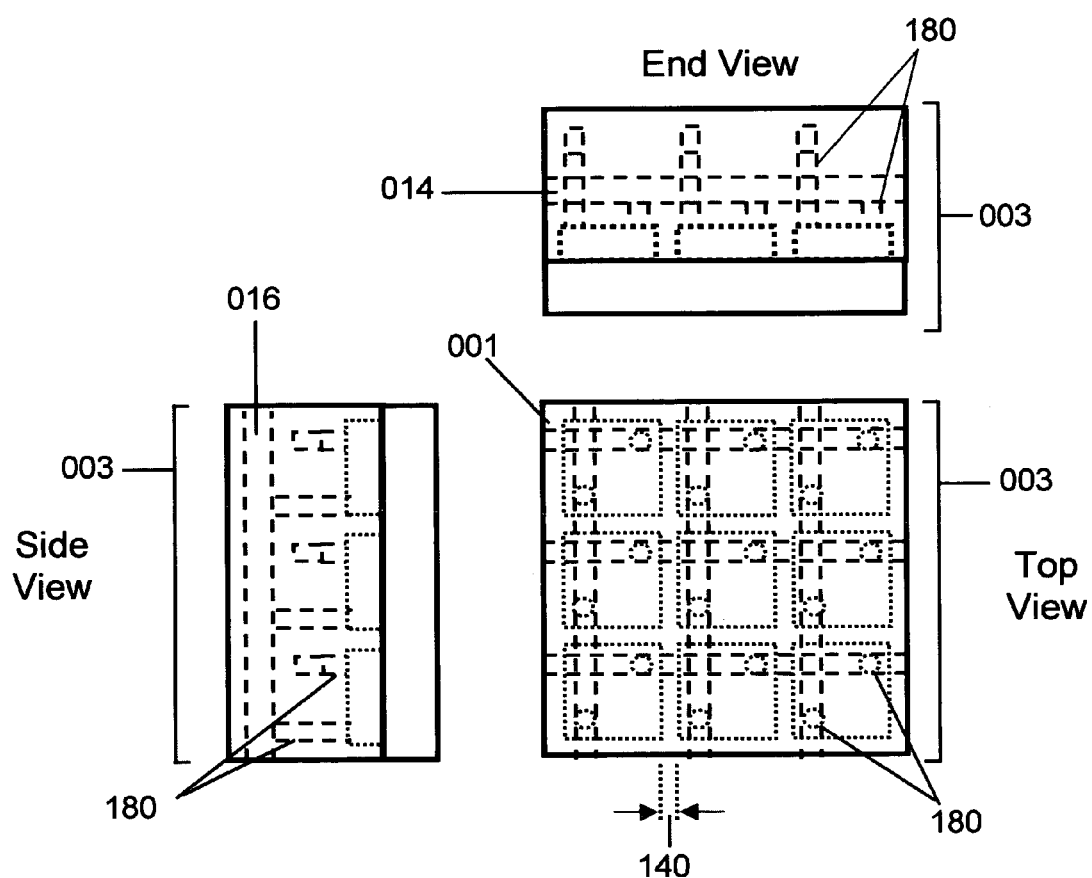
FIG. 26 depicts an end view and side view of the embodiment of FIG. 25.

The fluidic channels of the cassette of the present invention provide transport of fluid and compounds from source receptacles to each well and from each well to one or more waste receptacles. Each well could be provided with a separate input and output channel (FIG. 21), yielding $2n^2$ channels (100, 120) for an n×n array (040). To control the flow of m liquid or vapor mixtures to an n×n array, $m+n^2$ valves or pumps are required (FIG. 22). However, for a large array, the number of channels, pumps, and valves for this type of architecture becomes unwieldy. A pump that has variable or switchable pressure (e.g., a syringe pump) is functionally equivalent to a pressurized reservoir with a valve. Therefore, in the following discussions of pumps, reservoirs, and valves, it should be understood that these components may be substituted without altering the spirit of the invention.

Crossed-Channel Multilevel Architecture

A preferred embodiment of architectures of the cassette consisting of a crossed, nonintersecting array of input (100) and output (120) channels and utilizing multiple levels is disclosed. Specific embodiments within this class of architectures are given in FIGS. 23–26 and in FIGS. 33 and 34.

Because architectures in this class require fewer independent channels per well compared to the class of architectures with separate input and output channels for each well, these crossed-channel architectures also minimize the lateral space (140) that is required between wells to accommodate the pathways for the channels.

The crossed-channel, multilevel architectures require only 2n channels to address $n^2$ wells. In a preferred embodiment, the row and column channels themselves are formed in two distinct layers so that they do not intersect. The row channels lie above the column channels, or vice versa. These two layers lie either in the same plane of the well layer (FIGS. 23 and 24), or lie in a plane above the well layer (FIGS. 25–26 and 33–34). In other embodiments, structures with more than two planes are contemplated.

In a most preferred embodiment, the channels are placed above the plane of the wells, so that the minimum inter-well distance (140) is constrained only by the optical and physical requirements for a certain wall thickness separating each well. The advantage of placing the channels in levels above the wells is shown by the following examples. Wells that are 0.4 mm×0.4 mm can be placed on a 0.5 mm pitch grid with allowance for a 0.1 mm wall between wells, yielding a 5 mm×5 mm area for a 10×10 well array. Row and column channels of 0.2 mm width can easily be formed in upper levels of the device with ample distance between the channels. By contrast, if 0.2 mm channels with 0.1 mm walls are required within the plane of the wells (and row and column channel layers are formed in two separate planes within the plane of the wells), the well pitch increases to 0.8 mm. This yields an 8 mm×8 mm area for a 10×10 well array. In this example, the placement of the channels between the wells increases the area required for the array by a factor of 2.6. For different channel architectures with separate input and output channels for each well, the additional space required between wells is much greater.

Either for channels above or within the level of the wells, horizontal (160) or vertical (180) connecting channels or vias are formed from each well (j,k) to its corresponding row channel j and column channel k. Fabrication of such structures from glass, semiconductor, or plastic materials is well known in the art. In one such method, silicon dioxide ($SiO_2$) is lithographically formed within silicon nitride ($Si_3N_4$) layers using a multistep layer-by-layer process. (Turner and Craighead, Proc. SPIE 3528:114–117 (1998)) Exposure of the structure to a wet etchant removes the $SiO_2$ to create the channel network within the $Si_3N_4$, which is not etched.

Control of Flow in the Crossed-Channel Architecture

In a crossed array of rows (A, B, C, etc.) and columns (1, 2, 3, etc.) the flow of fluid to and from well (j,k) is produced when, for example, positive pressure is applied to row j and the valve of output channel k is opened, where j and k refer to, e.g., row D and column 7, respectively. Flow to all wells of an entire row j is produced when, for example, positive pressure is applied to row j and the valves of all output channels (1, 2, 3, etc.) are opened. A similar procedure would yield flow to all wells of a column.

The pressures that are discussed here are actually pressure differences relative to ambient atmospheric pressure, otherwise known as "gauge" pressure. Thus, the value of the positive pressure is the amount by which an applied pressure is greater than atmospheric pressure; the value of the negative pressure is the amount by which an applied pressure is less than atmospheric pressure. These pressures are referred to as positive and negative gauge pressure, respectively.

The term "fluid pathway" is used herein indicates the particular set of wells {(j,k), (j,n), (m,k), (m,n) . . . etc.} that is subjected to fluid flow by the enabling of the flow control devices of rows j and m, etc., and columns k and n, etc. Note that enabling the flow control devices of two rows and two columns yields a fluid pathway through four wells. This is defined herein as a single fluid pathway involving four wells, rather than four pathways involving single wells.

Reduction in the Number of Active Valves or Pumps

Figure 27:
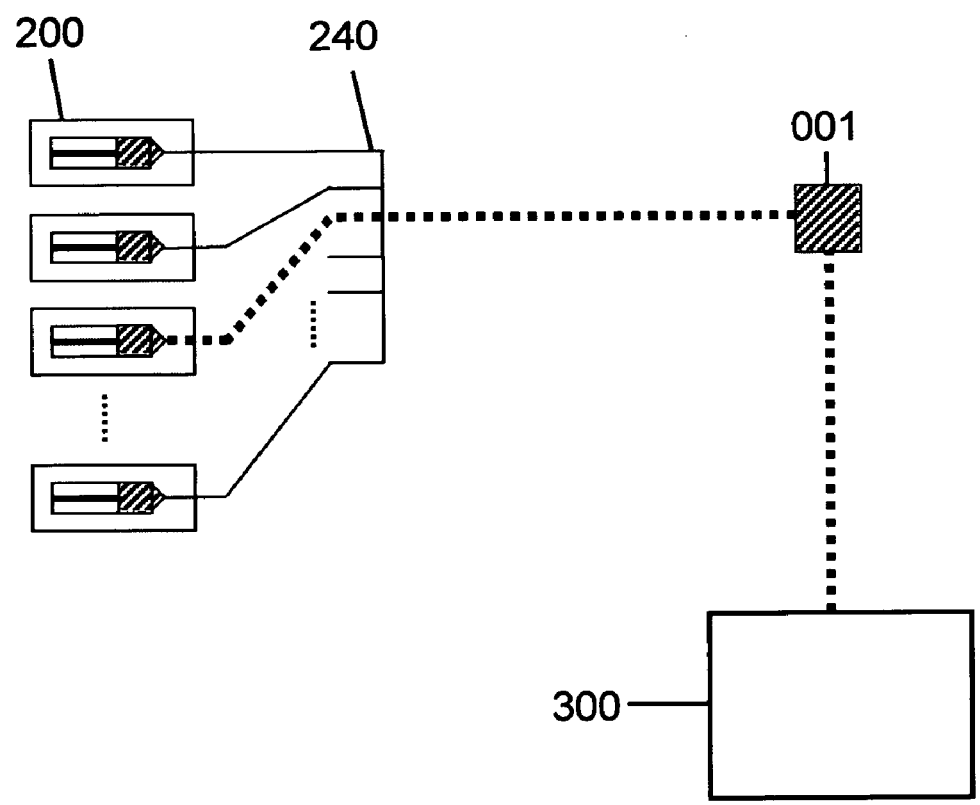
FIG. 27 shows an embodiment of the microfluidic device wherein compounds are multiplexed to a single fluidic location by using m positive pressure source reservoirs or pumps, a valve-less manifold, and valve-free waste reservoir at atmospheric pressure.
Figure 28:
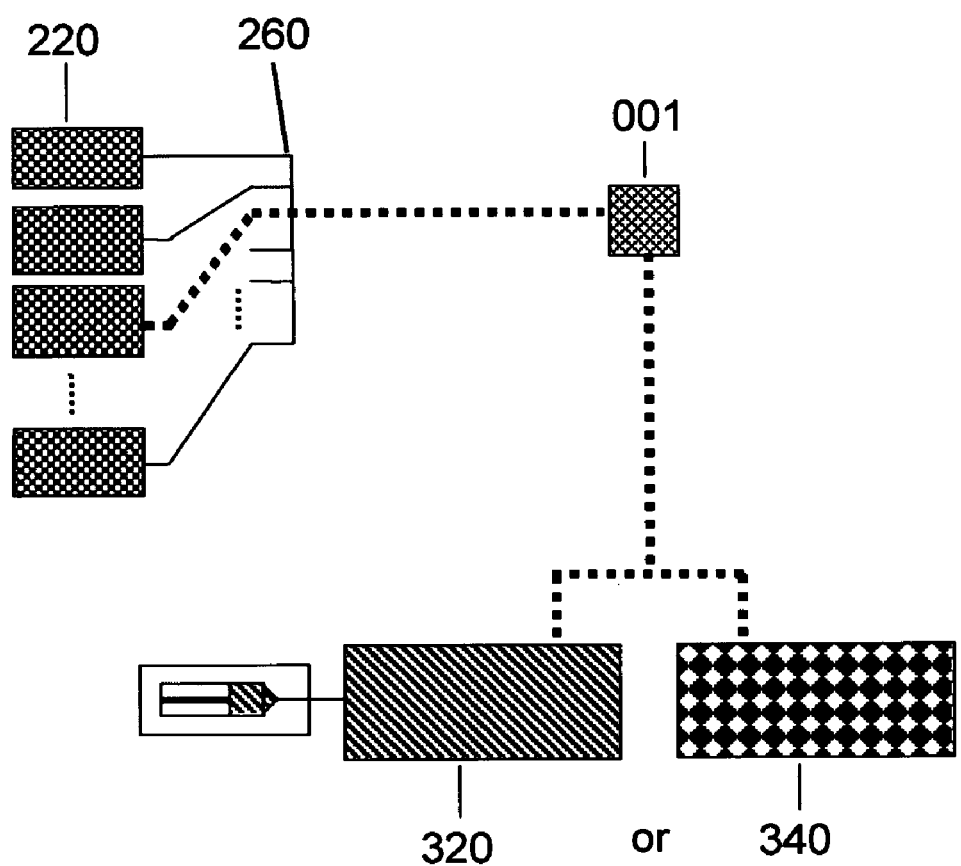
FIG. 28 shows an embodiment of the microfluidic device wherein compounds are multiplexed to a single fluidic location by using m positive pressure source reservoirs or pumps, a valved manifold, or a negative pressure waste reservoir or pump with m valves connected to m source reservoirs at atmospheric pressure and valve-free waste reservoir at atmospheric pressure.

Various combinations of actively-controlled flow control devices (pumps or pressurized reservoirs with valves) are used to produce flow through a desired well (010) or fluid pathway. For example, m compounds can be multiplexed to a single well by using m positive pressure source reservoirs or pumps (200), a valve-less manifold (240) and valve-free waste reservoir at atmospheric pressure (300)(FIG. 27). This valve-less manifold (240) can be replaced by a valved manifold [e.g., (260) of FIG. 28] to better control the diffusion of fluids between the m sources. Alternatively, the same functionality can be achieved by using a negative pressure waste reservoir or pump (320) with m valves (260) connected to m source reservoirs at atmospheric pressure (220)(FIG. 28). The use of source reservoirs at atmospheric pressure allows convenient bubbling of gases through the source reservoirs to establish and maintain desired levels of dissolved $CO_2$ and $O_2$ in the media.

In another embodiment, a waste reservoir filled with a porous medium serves as a capillary action pump (340) and provides negative pressure (FIG. 28). The thermodynamics of wetting creates a pressure across a liquid-vapor interface bounded by a solid-liquid-vapor contact line. This pressure of capillary action can be used to draw a column of liquid from any microchannel pathway into the high surface area porous medium. A series of such negative pressure reservoirs can be linked to the array via a multiplexing valved manifold for control of flow, or one single reservoir can be closely coupled to the output channels of all wells simultaneously. A number of porous media are known in the art, including, but not limited to silica gel technology, porous ceramic materials such as zeolite, a pad of hydrophilic (synthetic or natural) fibers, and partially hydrated or lyophilized hydrogels such as alginates, poly(vinyl) alcohol gels, agarose, sugar polyacrylate gels, and polyacrylamide gels. In a preferred embodiment, the porous medium is based on silica gel technology. A thin membrane or filtering sheet may be used to partition the porous media from the microchannel array. This method can provide pressure for pumping until the internal surface area of the porous medium is largely wetted by the liquid. By suitable choice of porous medium and design of this method, adequately large amounts of liquid can be pumped to conduct a chosen measurement with the array system of the present invention.

Figure 29:
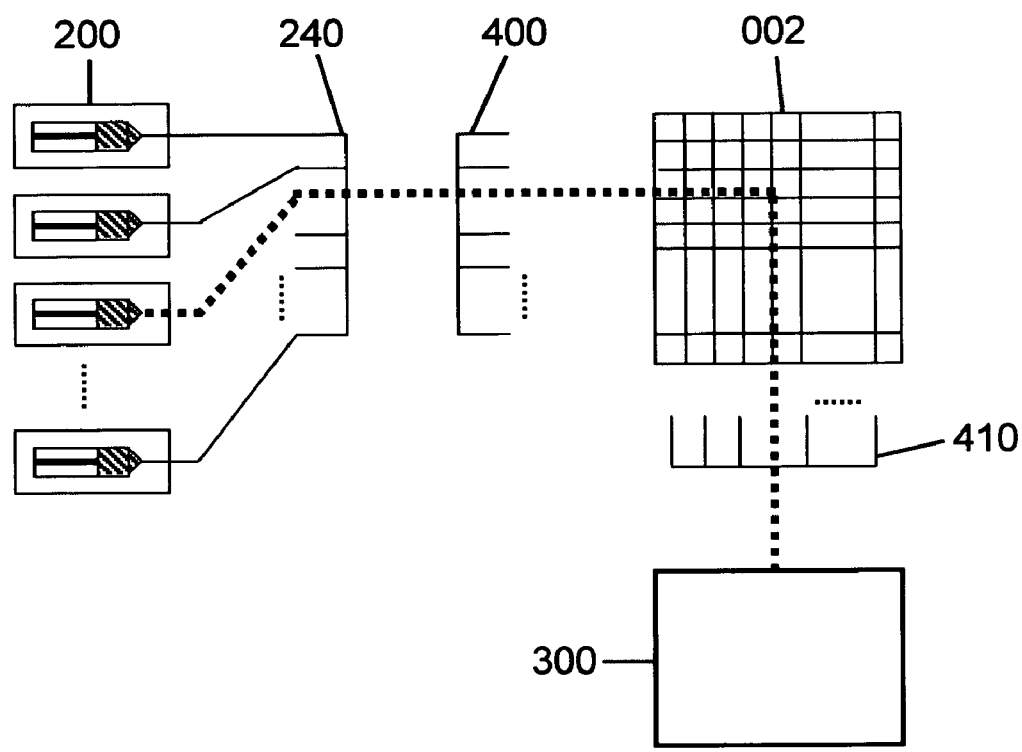
FIG. 29 shows an embodiment of the microfluidic device wherein the array of m positive pressure source reservoirs or pumps is multiplexed to an n×n crossed channel array of fluidic locations by means of 1×n input and n×1 output valve manifolds.
Figure 30:
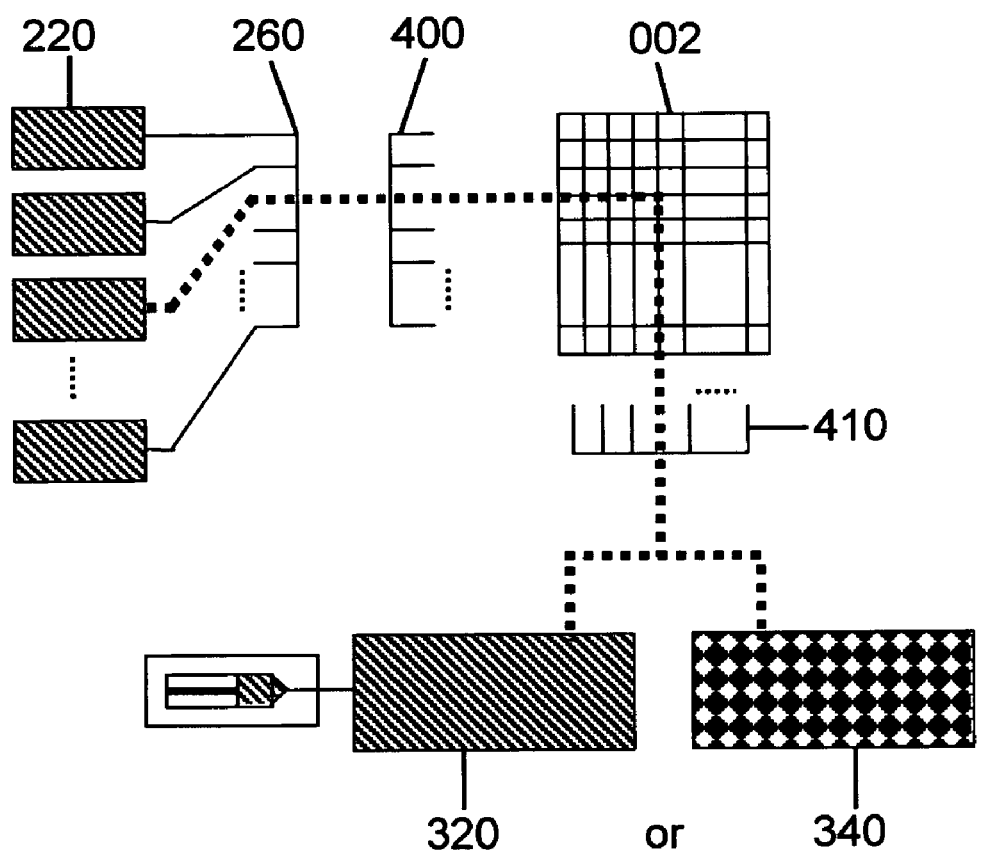
FIG. 30 shows an embodiment of the microfluidic device with m reservoirs at atmospheric pressure and a negative pressure waste reservoir by means of 1×n input and n×1 output valve manifolds, where the negative pressure reservoir may be either mechanically or thermodynamically pumped.

In another embodiment, the array of m positive pressure source reservoirs or pumps (200) shown in FIG. 27 is multiplexed to an n×n crossed channel array of wells (040) by means of 1×n input (400) and n×1 output (410) valve manifolds (FIG. 29). Recall that for architectures with separate input and output channels for each well (FIG. 22), m+n valves or pumps are required in this situation. Again, the valve-less manifold (240) can be replaced by a valved manifold [e.g., (260) of FIG. 28] to better control the diffusion of fluids between the m sources. Flow through well (j,k) is effected when input valve j and output valve k are opened. Alternatively, the same functionality can be achieved with m reservoirs at atmospheric pressure (220) and a negative pressure waste reservoir (either 320 or 340) as in FIG. 28 by means of 1×n input (400) and n×1 output valve (410) manifolds (FIG. 30).

Rinse Channels

In a preferred embodiment, an n×n microwell array is augmented by an additional column channel k* or set of column channels(s) {k*} that allow passing of a segment of liquid or vapor from a given row j to a waste reservoir without going through the wells {(j,k)} or the column channels {k}. These additional column channels {k*} are referred to as rinse channels (130), because they enable the rinsing of the row channels without requiring flow through the wells.

Figure 33:
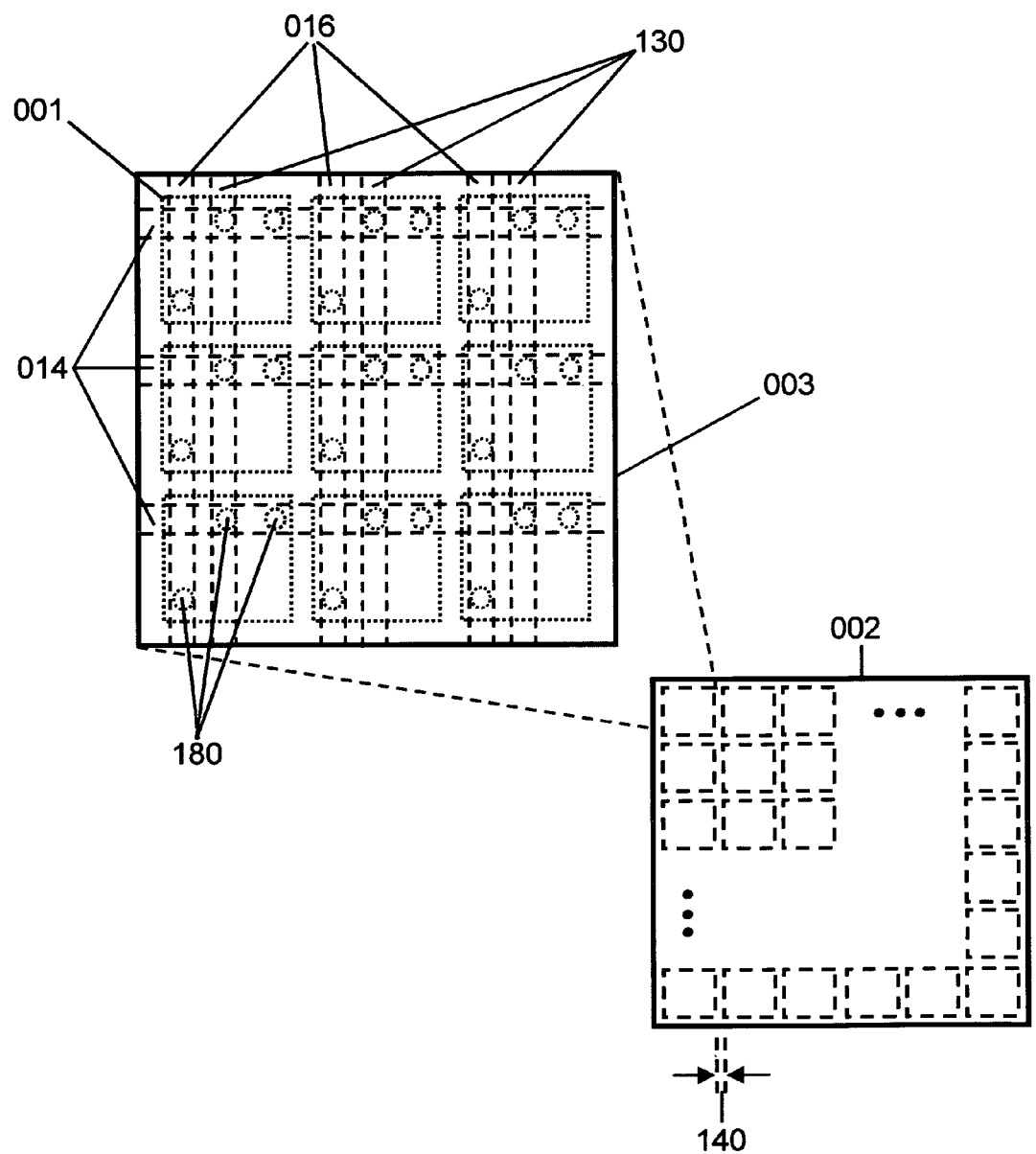
FIG. 33 depicts an embodiment of the microfluidic device wherein every column channel k has an associated parallel rinse channel k*.
Figure 34:
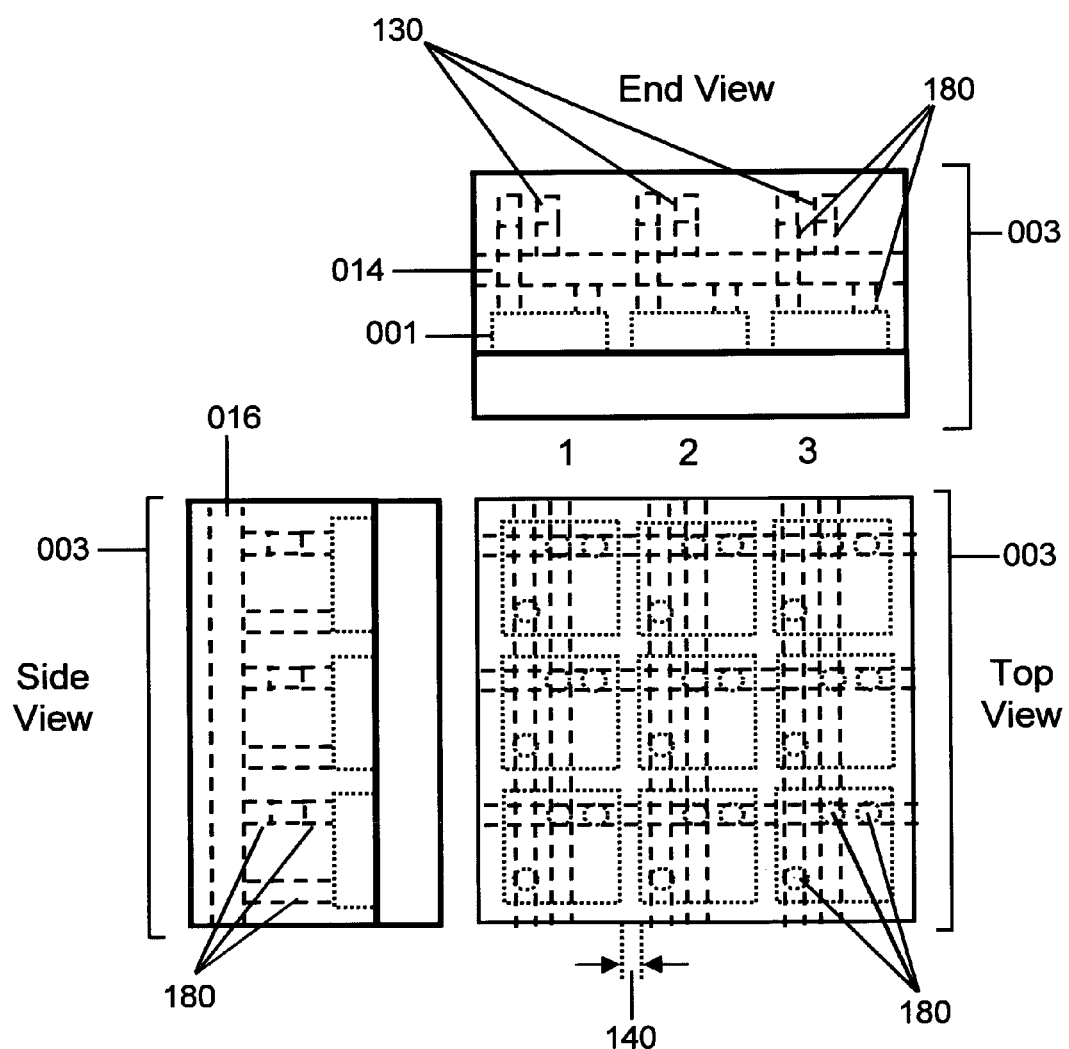
FIG. 34 depicts an embodiment of the microfluidic device wherein the fluid delivery system consists of a crossed, nonintersecting array of input and output channels with vertical connecting channels, utilizing multiple levels, wherein the two layers lie in a plane above that of the well layer and every column channel k has an associated parallel rinse channel k*.

In general, a rinse channel k* (130) can be located adjacent and parallel to column channel k (016) but be linked by a via to row channel j (014) at the point were they cross [and not be linked directly to the corresponding well (j,k)]. In one embodiment, every column channel k has an associated parallel rinse channel k* (FIGS. 33 and 34). In other embodiments, there is only one rinse channel to provide rinsing for the entire set of row channels {j}, or there is any combination of rinse channels {k*} interspersed within the array of column channels {k}. When there is only one rinse channel, it may be preferred to have it located adjacent to the last column channel of the array, where k=n.

Figure 35:
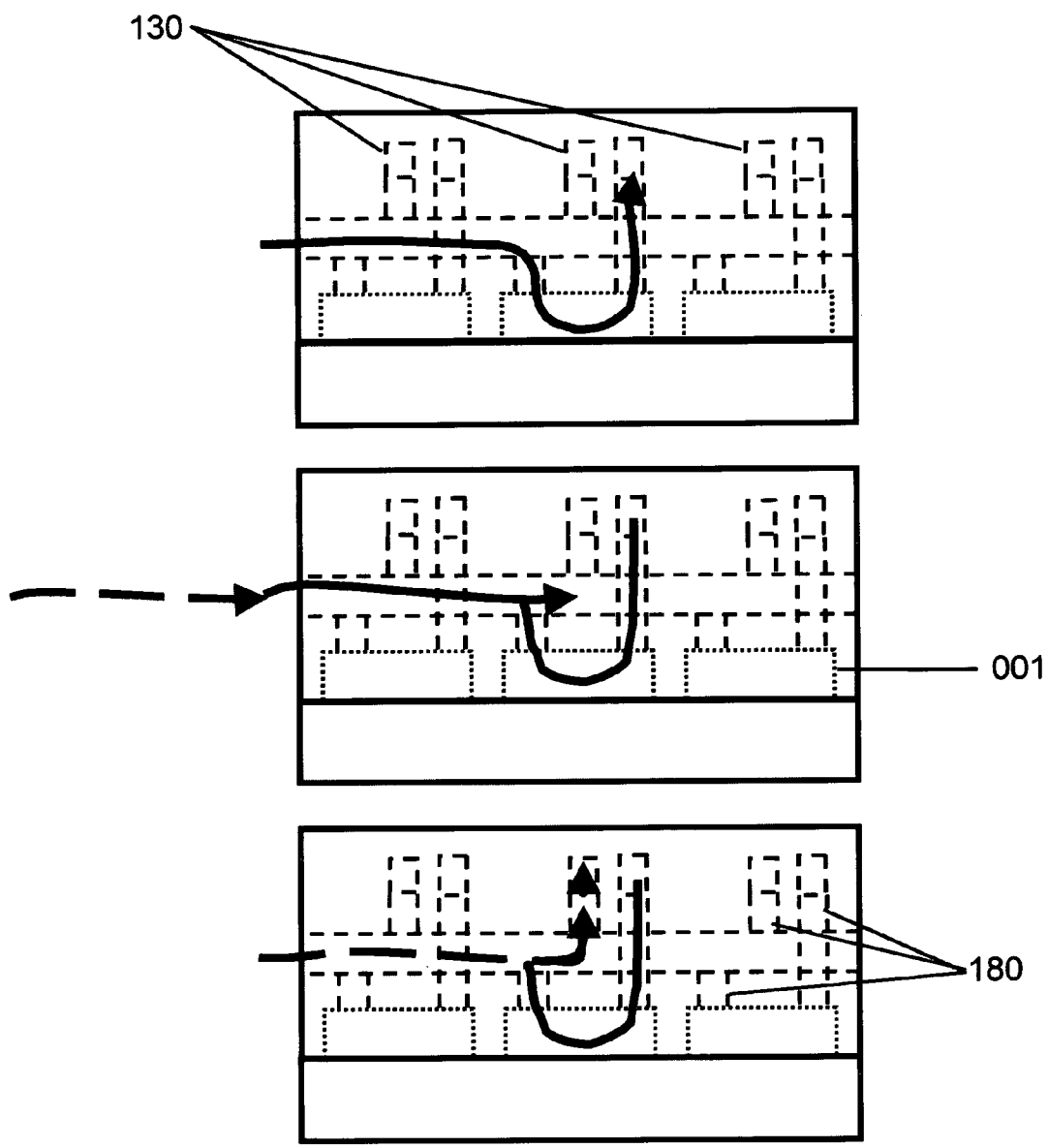
FIG. 35 shows, in a case of fluid flow through well (j,k), an example of a method to rinse a segment of liquid or vapor from row channel j and into rinse channel k*, where k* is immediately adjacent to column channel k.

FIG. 35 shows, in a case of fluid flow through well (j,k), an example of a method to rinse a segment of liquid or vapor from row channel j and into rinse channel k*, where k* is immediately adjacent to column channel k. This procedure and architecture allows this fluid segment to be directed to the waste reservoir without passing over wells {(j, k+1), (j, k+2), etc.} that are downstream along row channel j. This is desirable to limit the diffusion of a given compound from one well (j,k) to other wells downstream {(j, k+1), (j, k+2), etc.} where the compound may not be required. Additionally, as described below, diffusion may be controlled by introducing vapor segments into the microchannel microwell array.

Figure 32:
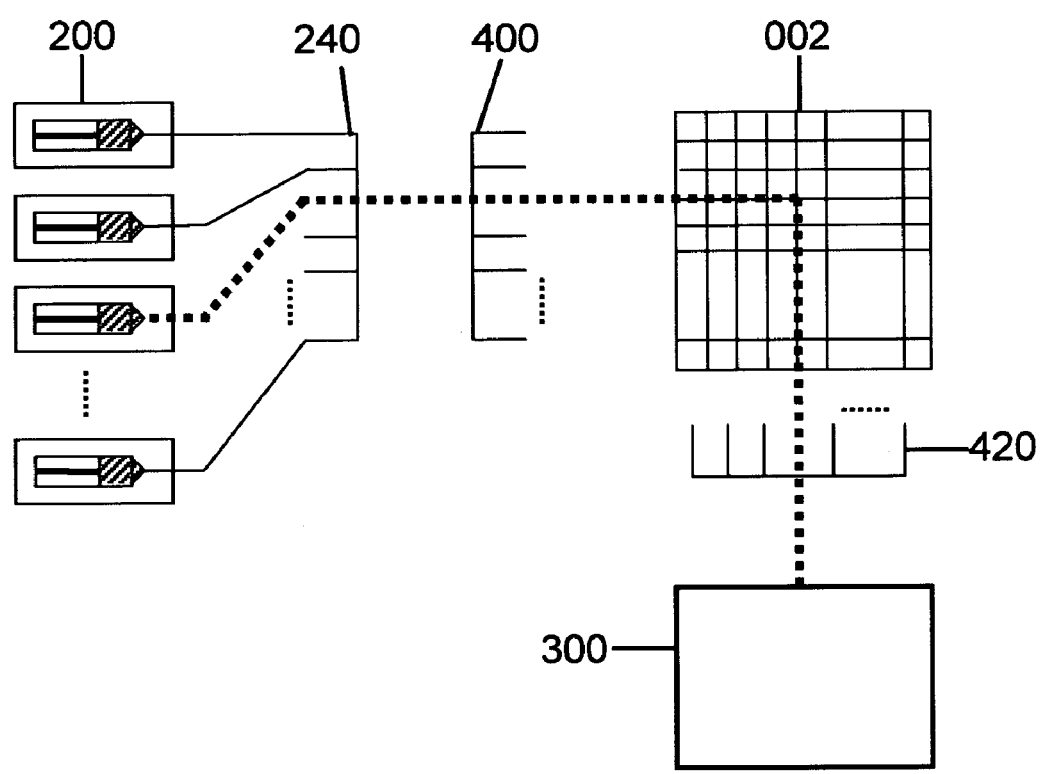
FIG. 32 shows how the pumping and valving scheme of FIG. 29, employing positive pressure source reservoirs, can be extended to work with a crossed array of n row channels and 2n column channels (n ordinary column channels plus n rinse column channels). This requires a 2n×1 output valve manifold. Similarly, the scheme of FIG. 30, employing a negative pressure waste reservoir, can be extended to work with an array incorporating rinse channels.

FIG. 32 shows how the pumping and valving scheme of FIG. 29, employing positive pressure source reservoirs, can be extended to work with a crossed array of n row channels and 2n column channels (n ordinary column channels plus n rinse column channels). This requires a 2n×1 output valve manifold (420). In general, for every additional rinse channel k* that is added, one additional valve is added to the valve manifold connected to the column channels. Similarly, the scheme of FIG. 30, employing a negative pressure waste reservoir, can be extended to work with an array incorporating rinse channels (130).

Dual-Pumped Designs

Flow through a fluid pathway {(j,k), (j,n), (m,k), (m,n) . . . etc.} or more generally through any length of tubing is caused by a continuous pressure gradient that exists along the length of the pathway or tubing. Control of this pressure gradient by means of pressures applied at the inputs and outputs of the fluid pathways requires that there not be leakage of flow across the walls of the pathway. Leakage also compromises the proper dosing of compounds to the wells for drug screening. The sealing of the walls of the pathways must be adequate for the gauge pressures that are likely to be applied. For fluid flow rates of roughly a few millimeters per minute, path lengths not greater than a few centimeters, and channel cross sections on the order of 100 mm×100 mm, the Hagen-Poiseuille law predicts that the required end-to-end pressure differential $\Delta P$ is less than 1 atmosphere (1 atm.$\approx$14 pounds per square inch). Nevertheless, considering that various materials and structures known in the art can be implemented for the device of the invention, the possibility of leakage between neighboring wells is minimized by reducing the gauge pressure exerted across the walls of the system. Towards this end, the present device can use positive pressure source reservoirs with a negative pressure waste reservoir (i.e., a "double-pumped" system) to essentially cut in half the maximum gauge pressures which must be applied to achieve a given total end-to-end pressure differential.

For a "single-pumped" system, i.e., a system that is open to atmospheric pressure at one end and that is pumped at the other end (either to a positive or to a negative gauge pressure, $\pm\Delta P$), the pressure difference exerted across the walls of the system is a maximum at the location of the pumped reservoir, i.e., (200) of FIGS. 27 and 29; or (320, 340) of FIGS. 28 and 30. Leakage is most likely to occur at these points of maximum gauge pressure, with positive pressure tending to expel fluid out of the pathway and negative pressure tending to draw fluid into the pathway from a neighboring well or channel. (This assumes that the neighboring channels and wells are held at zero gauge pressure when not subjected to flow. Another method to control the pressure differentials across the system walls is to apply matching pressures to the neighboring pathways while they are not under flow.) At intermediate points along the fluid pathway, the pressure differential across the system walls has values between $\pm\Delta P$ and zero for positive and negatively pumped systems, respectively.

The same end-to-end pressure differential $\Delta P$ is exerted across the pathway by establishing pressures $\pm\Delta P/2$ at the input and output reservoirs, respectively. In this case, the maximum gauge pressures exerted across the walls of the system are $\pm\Delta P/2$ and occur at the corresponding endpoints of the system. Moreover, the applied gauge pressure within the device is close to zero if the wells are roughly at the midpoint between the input and output reservoirs along the length of the pathway. At the endpoints of the pathway, the maximum pressure differences $\pm\Delta P/2$ are more readily held without leakage within plastic tubing or silica capillaries. Detection of leakage is facilitated because it is likely to occur only at the system endpoints.

In one embodiment, the two syringes of a dual pumping system are the same diameter and volume, and because they are linked to the same actuator in a push-pull configuration, each syringe is moved the same linear distance, and identical volumes are exchanged for each increment of movement. As any particular source compound is pushed into the array, an equal volume of waste fluid is pulled out. Thus, the array of m source syringes also contains an array of m negative pressure waste reservoirs. This array of negative pressure waste reservoirs is multiplexed to the column channels by a 1×m valve-less manifold, just as the array of source reservoirs is multiplexed to the row columns.

Figure 31:
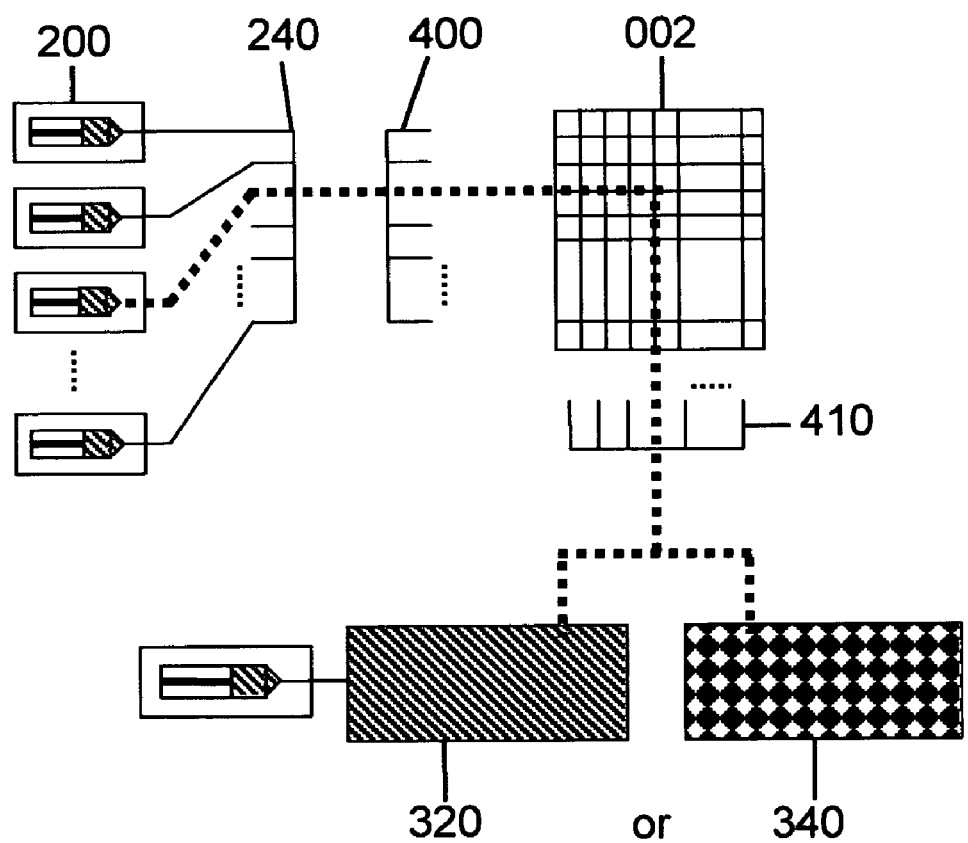
FIG. 31 shows an embodiment a dual-pumped system, in which there is only one waste negative pressure reservoir that must be actuated in coordinated fashion with the actuation of any particular positive pressure source reservoir. This negative pressure reservoir may function by either mechanical or thermodynamic (e.g., a capillary action pump) means. For the capillary action pump, the "actuation" of the pump is acheived by means of valves.

In another embodiment, the source and waste syringes are of different diameter, and the syringes must be controlled by two separate drivers that drive each syringe at a different linear rate, but yield the same volume changes in each syringe. For example, a smaller diameter syringe could be used for a compound, while a larger diameter syringe could be used as the waste receptacle. If the diameter ratio is a factor of 2, as the driver of the small syringe moves one linear unit to expel fluid, the driver of the large syringe moves only ¼ linear unit to withdraw fluid, but the volumes exchanged are identical. FIG. 31 shows one particular case of this embodiment of a "dual-pumped" system, in which there is only one waste syringe pump that must be actuated in coordinated fashion (e.g., by means of computer control) with the actuation of any particular source syringe pump. Alternatively, the negative pressure pump may be a capillary action pump, also shown in FIG. 31. For the capillary action pump, the "actuation" of the pump is achieved by means of valves.

In summary, the dual-pumped system has the following advantages:
1) reduction in the maximum applied gauge pressure,
2) the applied gauge pressure is small near the midpoint of the pathway, and
3) leakage is readily detected and most likely to occur at the system endpoints.

Higher-Level Multiplexing

The use of multi-port flow manifolds between the pumped reservoirs and the crossed channel array allows m different pumps (200) or reservoirs (220) in these various embodiments, with m different liquid or vapor mixtures to selectively and sequentially produce flow in each well (j,k) of the n×n well array (002). More generally, a set of wells defining a single fluid pathway {(j,k), (j,n), (m,k), (m,n) . . . etc.} can be defined by this system. Flow of only one liquid or vapor mixture can occur through only one fluid pathway at a time. Higher level multiplexing, allowing simultaneous flow of different liquid or vapor mixtures through different pathways, is possible with a more complex system of flow manifolds. Such a system is easily constructed as a generalization of the present design.

Control of Diffusion

The principle of this embodiment is that the valve element (520) and the valve seat (540) are shaped to allow flow in one direction and to suppress diffusion when flow is stopped.

Furthermore, the restoring forces on all valves are applied "passively" and constantly. No detailed control system for the check valves is needed, because the control of fluidic pressure gradients is the means by which individual valves are opened.

The use of crossed microchannels with a large number of open pathways between, for example, the 2n microchannels and the $n^2$ wells, may in some embodiments of the invention be augmented by additional methods to control the diffusion of compounds between wells and microchannels. Unlike prior art systems, the microfluidic system of the present invention does not need a detailed control system within the device for control of well-to-well diffusion. Two exemplary means of controlling inter-well diffusion are disclosed that do not require the active control of on-board valves. Both of these methods block inter-well diffusion by means of fluid flow control from valves, pumps, and manifolds that are external to the array of wells, and thus conform to the overall design principles of the invention: the optimal imaging of sub-arrays of wells in a class of fluidic architectures that requires fewer channels and permits smaller inter-well spacings.

The first method uses the insertion of segments of air between different fluid segments. The positive and/or negative pressure methods given in the above embodiments are employed to insert these air segments. In general, the application of differential pressure in appropriate sequences across a particular rows {j} and columns {k} or {k*} can place a number of separate air segments in the input channels {j} between a number of different fluids. In particular, appropriate sequencing can direct one fluidic segment to one well (j,k) and direct another fluidic segment to another well (j, k−1), while also inserting and maintaining an air segment in row j between these two wells. Subsequently, the air segment can be passed out of the system through an unused well or via a rinse channel k* (130)(FIG. 35).

Figure 36:
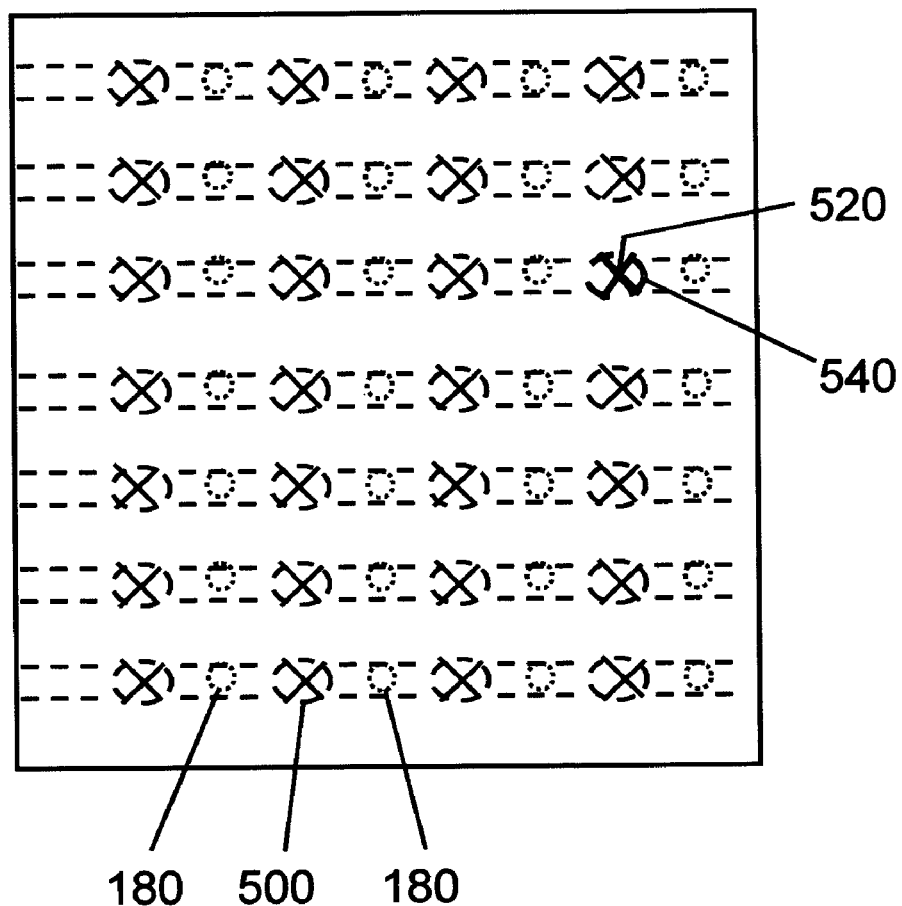
FIG. 36 depicts a method of diffusion control using "normally-closed" check valves, comprising a valve element and a valve seat, between every pair of adjacent vias that connect the channels to the fluidic locations.

The second method of diffusion control uses "normally-closed" check valves (500) between every pair of adjacent vias (via k and via k+1) (180) that connect the channels j to the wells (j, k) and (j, k+1) (FIG. 36). Similarly, check valves may be used in architectures incorporating rinse column channels {k*}. In other embodiments, check valves may be placed within the vias (160, 180) that connect wells to microchannels or row channels to rinse column channels. These valves are closed unless a pressure gradient is applied across a fluid pathway of the array. Then only those valves distributed along the selected fluid pathway are pushed open. When flow is stopped and the valves return to the closed position, the valves suppress diffusion of compounds between wells and microchannels, or row channels and rinse channels. The restoring force that closes each valve element (520) in its corresponding valve seat (540) may be provided by any number of methods known in the art. The strength of the restoring force must allow the valves to open upon the application of pressure gradients that yield appropriate flow rates (typically less than 1 cm/min.). Methods for application of restoring forces include mechanical force by the deformation of metallic, semiconductor, or organic materials; pneumatic pressure; electrostatic force, magnetic force, and the force of gravity.

Figure 37:
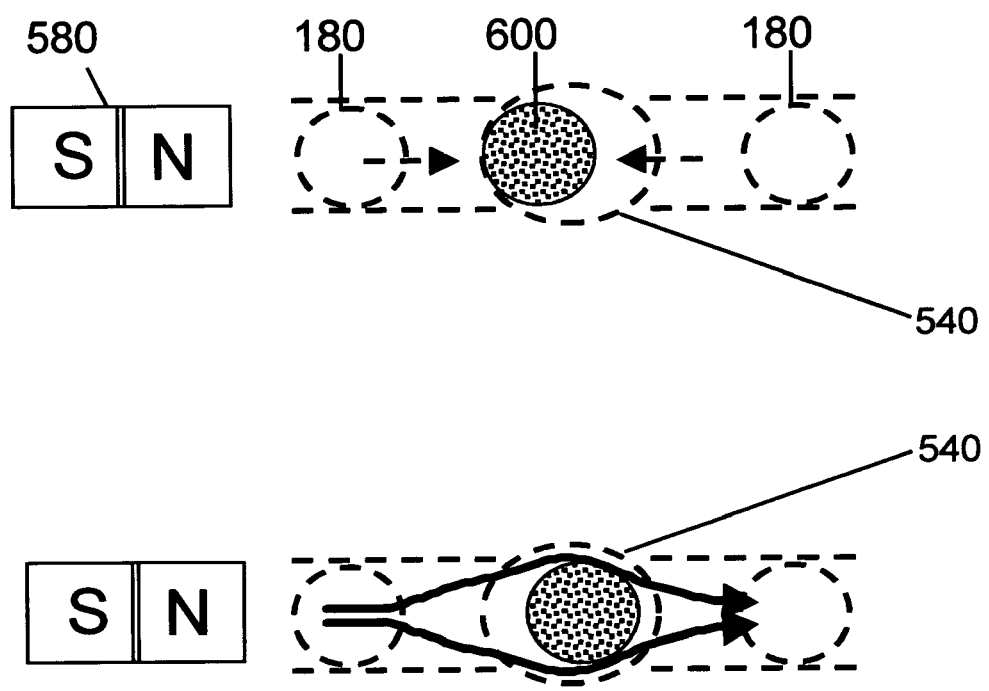
FIG. 37 depicts an embodiment wherein an externally-applied magnetic field gradient induces a restoring force on valve elements and valve seat that incorporate a magnetic material.

In another embodiment, an externally-applied magnetic field gradient (620) induces a restoring force on valve elements (520) that incorporate a magnetic material. This includes but is not limited to the use of paramagnetic beads (600) (e.g., supplied by Dynal Corp.) as shown in FIG. 37. These paramagnetic beads (600) serve as balls in micro ball valves that are fabricated within and along each row and column channel. U.S. Pat. Nos. 5,643,738 and 5,681,484 describe a magnetically-actuated microball check valve. However, these patents particularly describe an actively-controlled valve that would permit closure of the ball valve "on demand," and has as its purpose to stop flow that is imposed by some external pressure. In the instant case, the particular advantage to the microfluidic architectural system is that a mild restoring force is simultaneously applied to a large ensemble of ball valves throughout the array, and no active control is required. The movement of selected balls (whenever it is desired to open the valves) along a fluid pathway is achieved by means of causing the fluid itself to flow. The ball valve is controlled by the flow of fluid, not the flow of fluid is controlled by the ball valve. Moreover, in this embodiment, the valve seat is particularly designed so that a seal is not obtained in one direction, as opposed to the other direction, where a mild seal sufficient to stop diffusion is obtained.

In one embodiment, one micro ball valve is located between every pair of adjacent vias (via k and via k+1) that connect the channels j to the wells (j, k) and (j, k+1). Each micro ball valve opens only when a pressure gradient is applied across a pathway that includes that valve. The design of the valve seat (540) on one side is shaped (e.g., with grooves) so that flow is not stopped when fluidic pressure moves the ball in the direction of flow. When no pressure gradient is applied (and no fluid is flowing) at the site of a particular ball valve, a magnetic restoring force presses that paramagnetic ball back against the other side of the valve seat (540)(where the seat is shaped to fit the ball) to suppress diffusion of compounds across that portion of the microchannel. This restoring force is induced by a magnetic field gradient applied to the entire array, so that all valves are normally closed.

In another embodiment, an externally-applied magnetic field gradient (620) induces a restoring force on valve elements (520) that incorporate a ferromagnetic material. For example precision chrome steel balls are available from Glenn Mills Inc., Clifton, N.J. in a range of sub-mm to few mm diameters.

Figure 38:
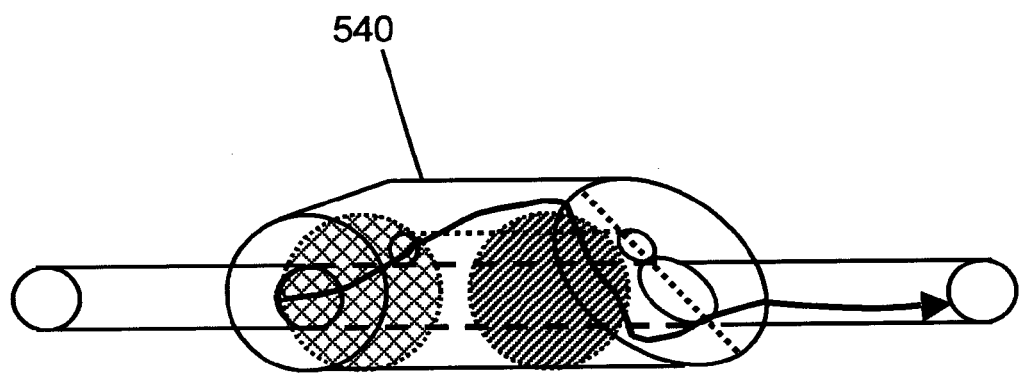
FIG. 38 shows an embodiment of a shaped valve seat wherein diffusion past the ball is stopped when the externally-applied restoring force presses the ball to the left into a round opening in the valve seat.

FIG. 38 shows an embodiment of a shaped valve seat that exemplifies this design principle. Specifically, diffusion past the ball is stopped when the externally-applied restoring force presses the ball to the left into a round opening in the valve seat. When flow is actuated by externally-applied pressures, the ball is forced to the right, but the ball does not stop the flow because the right side of the valve seat is oval shaped and includes a groove-like deformation at along one side, forming path for fluid to bypass the ball in this open position of the valve.

Figure 39:
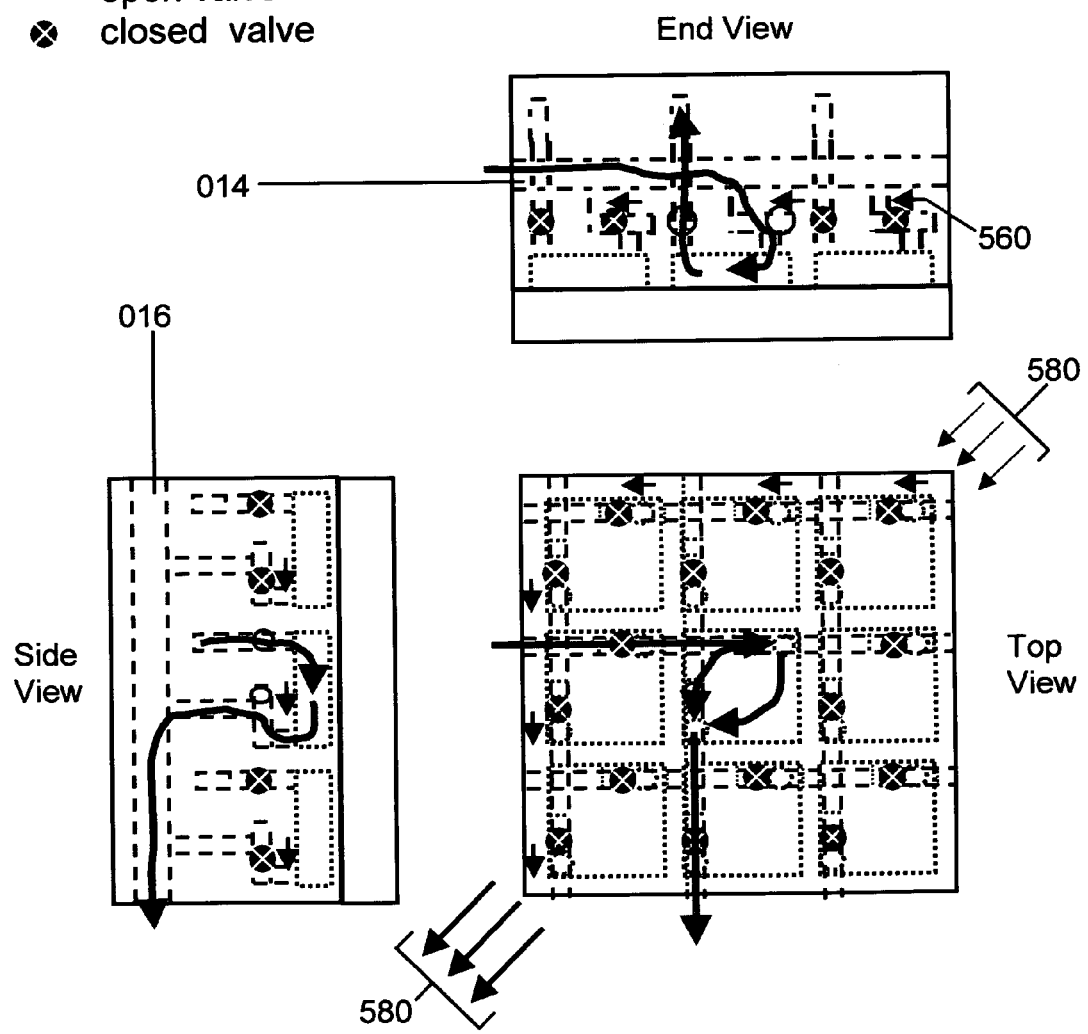
FIG. 39 shows an embodiment that allows a single magnetic field gradient applied to the whole microfluidic device to induce force on both a set of ball valves of the input channels and a set of ball valves of the output channels.

FIG. 39 shows an embodiment that allows a single magnetic field gradient applied to the whole cassette of the invention to induce force on both a set of ball valves of the input channels and a set of ball valves of the output channels.

In one embodiment the direction of the magnetic field gradient is parallel to the plane of the array, but oriented at 45 degrees to both the row and column channels. Thus each ball experiences a component of force in the direction of the "closed" side of its corresponding valve seat (540). In other embodiments, the magnetic field gradient is applied perpendicular to the plane of the array, and the ball valves operate in the vertical direction within the horizontal microchannels or within the vertical vias. In the latter case (vertically-actuated ball valves within vertical vias) the via architecture must again allow each ball to be subjected to a component of magnetic force in the direction of the "closed" side of its corresponding valve seat (540).

An example has been given of a ferromagnetic or paramagnetic valve element (520) of spherical shape, but other shapes and other restoring forces may generally be used that function in the same manner.

Well Dimensions and Characteristics

In another aspect, the present invention provides a cassette for cell screening, comprising a substrate having a surface, wherein the surface contains a plurality of cell binding locations; a fluid delivery system for delivering reagents to the plurality of cell binding locations, wherein the fluid delivery system comprises a multi-level chamber that mates with the substrate, wherein the multi-level chamber comprises a crossed array of microfluidic input channels and output channels and a plurality of fluidic locations in fluid connection with the microfluidic input channels and output channels; and a plurality of wells, wherein an individual well comprises the space defined by the mating of one cell binding location and one fluidic location, and wherein the wells are present at a density of at least about 20 wells per square centimeter. In a preferred embodiment, the well density is between about 20 wells per square centimeter and about 6400 wells per square centimeter.

In a preferred embodiment, the cassette of this aspect of the invention further comprises one or more input manifolds in fluid connection with the microfluidic input channels one or more output manifolds in fluid connection with the microfluidic output channels. In another preferred embodiment, the cassette of this aspect of the invention further comprises at least one source receptacle in fluid connection with the one or more input manifolds and at least one waste receptacle in fluid connection with one or more output manifolds. The various control devices in these embodiments are as described above.

No limitation is placed on the well shape geometry in the instant invention, as the well shape may differ in different embodiments of the invention. While a rectangular well shape allows for the minimum distance and area between wells in the array, this shape has the disadvantage of potential differences in cell culture or fluidic properties in the corner regions of the wells. Therefore, a well shape that is circular or that is rectangular with rounded corners is used in a preferred embodiment of the invention.

The array system of the present invention is designed for the imaging of individual cells within a field of cells in a drug screening assay system. Screening with imaging assays that involve the measurement of each individual cell within a field of cells, in parallel, is referred to as High Content Screening (HCS), because detailed information about intracellular processes is contained within the image of a single cell. Screening with lower resolution imaging or with detectors that integrate a signal over a population of cells is referred to as High Throughput Screening (HTS), because it is faster. In HCS, the cells are typically identified by imaging the nuclei of the cells, which are spherical or ellipsoidal in shape with a long-axis length that ranges typically from 5 μm to 15 μm. The cell array used in the present invention optimizes the rate of HCS by using a higher-density multiwell format compared to conventional 96-well plates.

For HCS, the number of cells that provide a statistically-relevant sample as well as the number of cells that are required per unit surface area varies depending on the type of assay and the type of cell being cultured. Thus, the minimum size of the well required by statistical criteria for each assay is different. Nevertheless, no matter what that minimum or optimum well size is, the rate at which wells can be read with adequate image resolution to resolve individual cell nuclei is optimized by the present device, which allows several wells to be imaged at one time in parallel. This is done most efficiently if there is minimal wasted space between wells, and the cell-plated area within the entire image is therefore maximized.

Moreover, the present array system optimizes the flexible implementation of both HTS and HCS on the same optical imaging cell-based screening system. The required pixel density (pixels per micron) is lower for HTS (for example, 0.001 to 0.1 pixels per micron) and higher for HCS (for example, 0.1 to 4.0 or more pixels per micron). The present system provides seamless, combined use of HTS and HCS, where a "hit" identified in HTS is also read in HCS mode for more detailed analysis. In fact, the availability of HCS on the same platform and with the same sample, greatly increases the information associated with "hits" identified in the HTS mode. Nevertheless, the fastest possible rate of HCS is advantageous to allow maximum overall screening throughput whenever HCS is used. The minimum pixel density required for HCS in combination with the maximum well density of the array are the two critical parameters that define the maximum rate at which wells can be read in the HCS mode. This invention describes how the design of the present array system can maximize this HCS rate, as well as the HTS rate.

In use with 96-well microplates, a conventional microscope imaging system can image square fields that are 0.1 mm to 10 mm wide centered on each 7-mm diameter well. The wells are imaged or "read" in series. At each position of the stage, typically, only one area of a well is read. To read the entire array (either in HTS or HCS modes) the sample stage must move the microplate at least 96 times.

In this invention, we define a novel cell screening method in which many wells are read at one time. Because the present array has well widths and inter-well distances that are roughly 10 times smaller than in the 96-well microplate (wells that are sub-millimeter in width and overall plate dimensions of several millimeters rather than several centimeters wide), a cell screening system, such as that disclosed in the present invention, can image many wells simultaneously. Thus, the sample stage is moved fewer times per plate and several wells are read in parallel (FIG. 39).

This essentially involves the serial imaging of "sub-arrays" (020) of the entire microwell array (040), while acquiring data from all wells of each sub-array in parallel. For example, the imaging of 3×3 well sub-arrays requires 9 times fewer movements of the sample stage, and allows a roughly 9-times faster rate of data acquisition.

For a given CCD detector array (080), the magnification of the optical system (060) determines the area of the sub-array (020) that is projected onto the detector. For example, an image pixel density of 1 pixel per micron is achieved for a 1000 μm×1000 μm sub-array of wells by using 10× optical magnification and a 1000×1000 pixel CCD array of 10 μm×10 μm elements. In a second example, a 2000 μm×2000 μm sub-array of wells can be imaged onto a 2000×2000 pixel CCD array at the same magnification to yield the same image pixel density. In a third example, an image pixel density of 0.1 pixel per micron is achieved for a 10 mm×10 mm sub-array of wells by using 1.0× optical magnification and a 1000×1000 pixel CCD array of 10 μm×10 μm elements. In a fourth example, a 10 mm×10 mm sub-array of wells can be imaged onto a 2000×2000 pixel CCD array at 2.0× magnification to yield the same image pixel density.

Below we give embodiments of particular embodiments of well sizes and spacings according to the present invention that optimize the imaging of sub-arrays. These well sizes must be large enough to contain a desired number of cells bound to a desired number of cell binding sites within each location of the array. Due to the considerable range of desired cell densities to be cultured on the cell binding sites (i.e.: cultures of very widely spaced cells, or of confluent monolayers may be desired), the desired well size may range from that which contains only one cell on a very small cell binding site of about 10 μm in diameter (i.e.: a well size of 20 to 50 microns), to that which contains either one large cell binding site or an array of many cell binding sites (i.e.: a well size of 1 to 2 mm) comprising a single location of the array. The former case leads to higher well densities, and the latter to lower well densities.

For both high and low well densities, and for wells that contain one or many cell binding sites, the class of microfluidic architectures according to the present invention permit the optimal spacing of wells, the minimal wasted space between the wells, and the maximum number of wells that can be simultaneously imaged in a sub-array and still obtain adequate pixel resolution in the image.

We now use the four examples of optical resolution given above to illustrate how for a preferred range of sub-array sizes, optical magnifications, and pixel resolutions, and based on the advantages of the microfluidic architecture described herein, the present device supports well sizes and spacings that enable great increases in the speed at which the wells can be imaged or read. Additional sub-array sizes, optical magnifications, and pixel resolutions are supported by the methods and devices of the invention. The scope of the invention is not limited by the current state of the art in the number of available pixels, nor in the pixel sizes in electronic imaging systems.

1. For the first example above, a 1000 μm×1000 μm sub-array of wells is imaged onto a 1000×1000 pixel CCD camera (with image resolution of 1 pixel per micron). We now give four examples of well sizes and densities that are supported by this invention. (a) First, a 2×2 sub-array of 300 μm×300 μm wells with 200 μm-thick walls and a well density of 400 wells per cm². Imaging these wells in groups of 4 yields a 4-fold speed increase compared to reading the plate one well at a time. (b) Second, a 3×3 subarray of 200 μm×200 μm wells with 100 μm walls yields a 9-fold increase in speed and a well density of 1111 wells per cm². The number of wells per unit area is a factor of 80 greater than that provided by the current highest density commercial microplate (the 1536 well plate). (c) Third, a 5×5 sub-array of 100 μm×100 μm wells and 100 μm walls yields a 25-fold speed increase and a density of 2500 wells per cm². (d) Fourth, for an even higher density of wells and a greater speed advantage, the well can be 25 μm×25 μm with 100 μm walls, yielding an 8×8 sub-array, a 64-fold speed increase, and a well density of 6400 cells per cm².

2. For a 2000 μm×2000 μm sub-array of wells imaged onto a 2000×2000 pixel CCD camera (with image resolution of 1 pixel per micron), one additional example of well density is considered in addition to the four examples considered above. (a) First, a 2×2 sub-array of 800 μm×800 μm wells with 200 μm-thick walls yields a 4-fold speed increase and a well density of 100 wells per cm². The number of wells per unit area is a factor of 5 greater than that provided by the current highest density commercial microplate (the 1536 well plate). (b) Second, a 4×4 sub-array of 300 μm×300 μm wells with 200 μm-thick walls yields a 16-fold speed increase and a well density of 400 wells per cm². (c) Third, a 6×6 sub-array of 200 μm×200 μm wells with 100 μm walls yields a 36-fold speed increase and a well density of 900 wells per cm². (d) Fourth, a 10×10 sub-array of 100 μm×100 μm wells with 100 μm walls yields a 100-fold speed increase and a well density of 2500 wells per cm². (e) Fifth, a 16×16 sub-array of 25 μM×25 μM wells with 100 μm walls yields a 256-fold speed increase and a well density of 6400 wells per cm².

3. For a 10 mm×10 mm sub-array of wells imaged onto a 1000×1000 pixel CCD camera (with image resolution of 0.1 pixel per micron), we again describe the four cases of well sizes and densities described in example 1 above. (a) First, a 20×20 sub-array of 300 μm×300 μm wells with 200 μm-thick walls yields a 400-fold speed increase and a density of 400 wells per cm². (b) Second, a 30×30 sub-array of 200 μm×200 μm wells with 100 μm walls yields a 900-fold speed increase and a well density of 1111 wells per cm². As before, this case supports a well density 80 times greater than that provided by the current highest density commercial microplate. (c) Third, a 50×50 sub-array of 100 μm×100 μm wells with 100 μm walls yields a 2500-fold speed increase and a well density of 2500 wells per cm². (d) Fourth, an 80×80 sub-array of 25 μm×25 μm wells with 100 μm walls yields a 6400-fold speed increase and a density of 6400 wells per cm². For an even higher density of wells and a greater (2500 fold) speed advantage, the wells can be 100 μm×100 μm with walls separating the wells that are 100 μm wide, yielding 2500 wells per sub-array, and 2500 wells per cm².

4. For a 10 mm×10 mm sub-array of wells imaged onto a 2000×2000 pixel CCD camera (with image resolution of 0.1 pixel per micron), the cases from example 2 above of 100, 400, 1111, 2500, and 6400 wells cm² again apply, but yield 100 times greater speed increases because the sub-arrays are 10 times wider on each side. Thus, the speed increases for well densities of 100, 400, 1111, 2500, and 6400 wells/cm2 are 400×, 1600×, 3600×, 10,000×, and 25,600×, respectively, in the 10 mm×10 mm array.

TABLE 2

The following table compares well pitches for various other devices:

| Type of plate | Reference | Well to well distance (mm) | Wells/cm² | Estimated Speed increase* |
|---|---|---|---|---|
| Standard 1536 well plate | | 2.25 | 20 | |
| 12 × 12 array in 1.5" × 1.5" area | Gen. Engr. News 18:12 (1998) | 3 | 11 | |
| 864 well plate: 24 × 26 array in std. microplate footprint of 108 cm² | U.S. Pat. No. 5,910,287 | 3 | 11 | |
| 9600 well plate: 80 × 120 array in a std. microplate footprint of 108 cm² | U.S. Pat. No. 5,910,287 | 0.9 | 123 | |
| | Present invention | | | |
| 1 mm × 1 mm subarray: 1000 × 1000 pixel CCD | Example 1(a) | 0.5 | 400 | 4X |
| | Example 1(b) | 0.3 | 1111 | 9X |
| | Example 1(c) | 0.2 | 2500 | 25X |
| | Example 1(d) | 0.125 | 6400 | 64X |
| 2 mm × 2 mm subarray: 2000 × 2000 pixel CCD | Example 2(a) | 1 | 100 | 4X |
| | Example 2(b) | 0.5 | 400 | 16X |
| | Example 2(c) | 0.3 | 1111 | 36X |
| | Example 2(d) | 0.2 | 2500 | 100X |
| | Example 2(e) | 0.125 | 6400 | 256X |
| 10 mm × 10 mm subarray: 1000 × 1000 pixel CCD | Example 3(a) | 0.5 | 400 | 400X |
| | Example 3(b) | 0.3 | 1111 | 900X |
| | Example 3(c) | 0.2 | 2500 | 2500X |
| | Example 3(d) | 0.125 | 6400 | 6400X |
| 10 mm × 10 mm subarray: | Example 4(a) | 1 | 100 | 400X |

TABLE 2-continued

The following table compares well pitches for various other devices:

| Type of plate | Reference | Well to well distance (mm) | Wells/cm$^2$ | Estimated Speed increase* |
|---|---|---|---|---|
| 2000 × 2000 pixel CCD | Example 4(b) | 0.5 | 400 | 1600X |
| | Example 4(c) | 0.3 | 1111 | 3600X |
| | Example 4(d) | 0.2 | 2500 | 10,000X |
| | Example 4(e) | 0.125 | 6400 | 25,600X |

*Estimated speed increase is a comparison of the speed at which the entire array could be imaged by sub-arrays compared to imaging by separately imaging each well All of these particular aspects of the instant microfluidic device—the crossed-channel, multilevel architectures, the high well density, the fluid flow control into these architectures, the arrangement of wells into spatially-optimized sub-arrays of wells, and the optional means of control of inter-well diffusion of compounds—are specifically selected and designed to form an integrated system that is compatible with the use of cell culture medium (a polar, aqueous solution containing biological macromolecules and salts), with the maintenance of desired, physiological levels of dissolved oxygen and carbon dioxide gases in the medium, and with the maintenance of desired, physiological temperature (typically 37° C., but other temperatures in the approximate range of 15° C. to 40° C. may be desired for particular cell types).

Particularly, the cell culture medium may be equilibrated in off-board vessels to the desired levels of temperature and dissolved carbon dioxide and oxygen. Then, using off-board vessels and valves, the medium is moved through the microchannels and to the wells. The sealing of these microchannels and wells from the atmosphere enables the partial pressures of gasses to be controlled by means of the equilibration of the external vessels. In a preferred embodiment, the level of carbon dioxide in the media within the wells may be established and maintained by equilibrating the media prior to its flow into the device, and/or by allowing exchange of a mixture of carbon dioxide and air with the media as it sits within the well. A number of different environmentally controlled chambers for live cell culture exist. (U.S. Pat. Nos. 5,552,321 and 4,974,952; Payne et al., J. Microscopy 147:329–335 (1987); Boltz et al., Cytometry 17:128–134 (1994); Moores et al., Proc. Natl. Acad. Sci. 93:443–446 (1996); Nature Biotech. 14:3621–362 (1996)).

Figure 12:
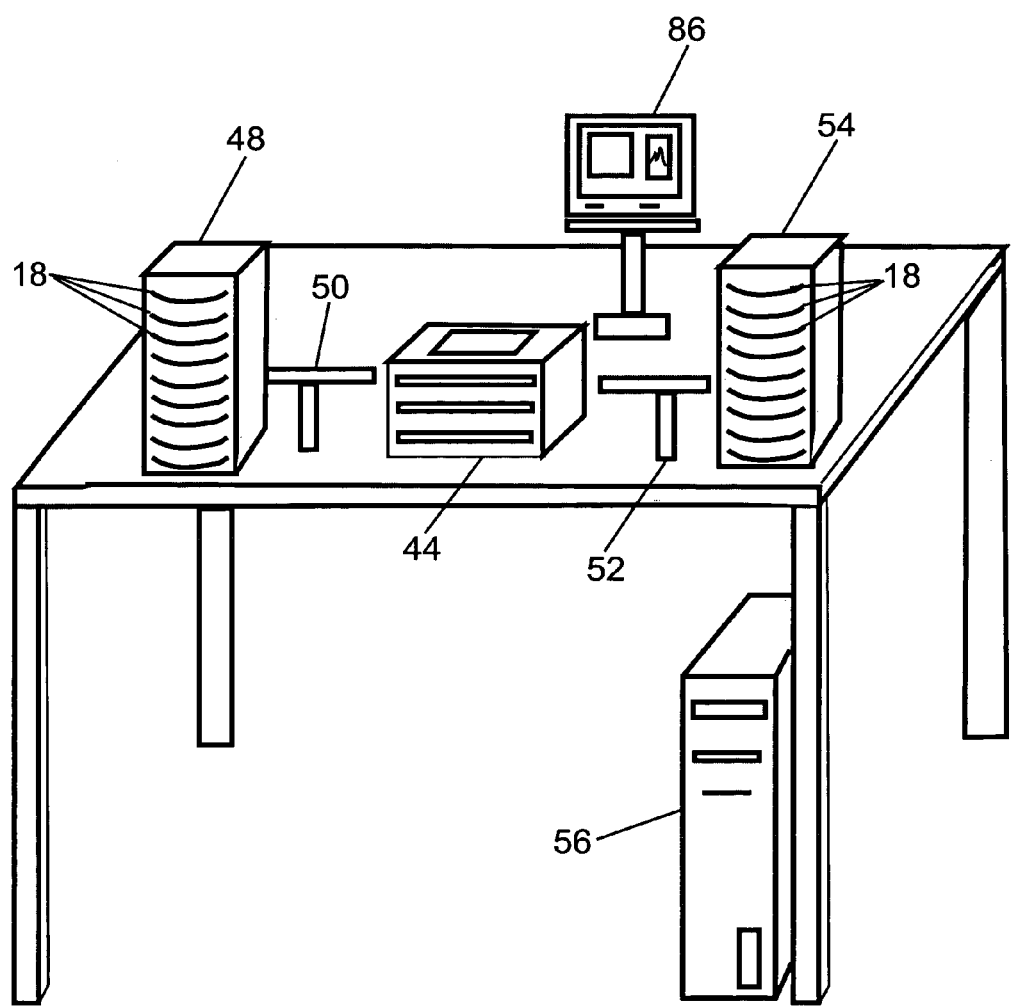
FIG. 12 is a diagram of the luminescence reader instrument.

In a further preferred embodiment, the temperature of the entire substrate is controlled by being in contact with, or composed integrally with, a heater and with a temperature sensor. An electronic temperature control system regulates the heater to attain a chosen temperature set point. Thus, the design of the microfluidic array system described in this invention is readily used in a way that supports live cell culture without an external incubator system. FIG. 12 shows how this invention provides for the automated reading of cassettes. The cassettes are kept under controlled environmental conditions within two storage compartments (48 and 54) before and after reading in the luminescence reader instrument 44. While being read by the luminescence reader instrument, the system maintains the appropriate temperature and composition of dissolved gasses in the cell culture media within the wells of the cassette. Temperature control within the wells is provided by heating device(s) and temperature sensor(s) within the cassette of the luminescence reader instrument. Control of dissolved gas composition within the wells is provided by equilibration of the media with a source of pre-mixed air and carbon dioxide (available commercially) prior to the flow of media into the wells of the cassette. Any type of controller for regulating gas partial pressures may be used with the instant invention. In a preferred embodiment, the system comprises a gas controller comprising a pre-mixed gas source connected to a reservoir or reservoirs containing cell culture media and/or test compounds. A gas pressure regulator and flow control valve control the rate of flow of this gas mixture and its pressure in the connected fluid reservoir(s). This equilibration of the gas mixture with the fluids may be carried out in reservoirs either on-board or off-board the cassette, but in any case, outside the matrix of the wells.

The present invention fulfills the need in the art for devices and methods that decrease the amount of time necessary to conduct high throughput and/or high content cell-based screening. The devices of the invention are also ideally suited as a cell support system for a hand-held diagnostic device (i.e.: a miniaturized imaging cell-based assay system). The drug discovery industry already uses 96-well microplates and is in transition towards the use of 384-well plates. Plates with up to 1536 wells are envisioned. Thus, there is a great advantage in both throughput and economy from the use of even higher density plates, such as that of the present invention.

The sealed containment of the cells in the cell array of the instant invention will provide a rugged system that is portable and usable in any orientation. For military and civilian toxin testing, the devices of the instant invention will provide two primary advantages. First, toxin testing based on cellular function is advantageous compared to toxin testing based on molecular structure (e.g., mass spectrometry or optical spectroscopies), because it tests the ultimate effect of the compound on tissue rather than a related property of the compound whose link to toxicity may be unknown or dependent on other conditions. Second, an automated, miniaturized, sturdy, and portable format for cellular-function based sensor would be advantageous compared to the current state-of-the-art that involves large microplates filled by large robotic pipetting systems and read by large microscopic readers.

Additionally, other assay capabilities can be integrated into the device of the present invention that are not possible in prior art devices, such as simple plastic microplates. For example, a mass spectrometric or capillary electrophoretic analytical device, or systems for DNA and/or protein analysis, can be integrated in the instant device to measure chemical and structural parameters of test compounds. Such integration would provide information that is complementary to the cell-based, functional parameters measured by a HCS or HTS system. For conventional microplates, such additional assay functions are external to the plate, and therefore require extensive additional equipment for both the transfer of samples from the microplate and for the analytical equipment itself. In the miniaturized format with integrated fluidics of the present invention, the sample is integrally pumped to a microanalytical system on the chip or on an integrally-connected second chip. Such microanalytical chips will reduce the cost and dramatically increase the speed of cell-based analysis. In this context, the marriage of a microscale live-cell analytical system with a microscale chemical analytical system is expected to provide great improvements over existing methods and devices.

EXAMPLE 4

Cell Patterning

Polymeric and glass surfaces in their native structures have been used as cellular growth substrates for decades. Differing techniques have been utilized to adjust the surface chemistry of these materials to make them more attractive for cell adhesion, including adsorption of cell adhesion molecules; sulfonisation of the material (European Patent Application 576184); co-polymer blends of extracellular matrix protein fragments such as RGD (U.S. Pat. No. 5,733,538); and chemical oxidation (using solution chemistry) of the surface for further chemical modification (using solution chemistry) (U.S. Pat. No. 5,330,911) such as silanes (U.S. Pat. No. 5,077,085) or thiols (U.S. Pat. No. 5,776,748).

In addition to adjusting the surface of these substrates to render them more attractive for cellular adhesion, techniques have been developed to render the surfaces repulsive for cellular adhesion. Cell repulsive surfaces have been achieved by utilizing extremely hydrophobic surfaces (contact angle >90°), which show cell repulsion for several days. (Dulcey et al., Science 252:551 (1991)). A more widely utilized method employs extremely hydrophilic surfaces (contact angle approximately 0°), by immobilizing sugars and oxygen-rich moieties to the surface through common linking chemistries. These surfaces demonstrate longer periods of cell repulsion before degrading and allowing cell adhesion. The most utilized molecule for cell repulsion is oxygen-rich poly(ethylene glycol) (PEG). PEG can be attached to polymeric and glass substrates by methods including chemically activating the substrate to react with a poly(ethylene imide)-PEG molecule (Brink, Colloids and Surfaces, 1992. 66: p. 149–156), aminating an activated surface and reacting it with bifunctional electrophilic molecules such as PEG-epoxide (Bergstrom, K., Journal of Biomedical Materials Research, 1992. 26: p. 779–790; WO 98/32466 EP0576184, Nilsson, D., in Methods in Enzymology, 1984. 104: p. 56–69; Sofia, S., Macromolecules, 1998. 31: p. 5059–5070), and photochemically through photolabile PEG-conjugates such as PEG-benzophenone and PEG-styrene co-polymer blends. (Becker, Makromolecular Chemistry, 1982. 3: p. 217–223; U.S. Pat. No. 5,502,107).

The techniques mentioned so far will lead to homomonolayers, containing one of the cell attractive or cell repulsive moieties. A combination of the above technologies can lead to the creation of hetero-monolayers. If the positioning of these cell adhesive and cell repulsive cues can be controlled to a high degree, cells can be patterned on the substrate of choice. Cell patterning has been achieved on glass and metalized glass substrates utilizing silanes (U.S. Pat. No. 5,077,085), thiols (U.S. Pat. No. 5,776,748), and azidos (U.S. Pat. No. 5,593,814). These methods provide selective localization of cells using a multi-step, equipment intensive process, and/or irreproducible techniques such as deep ultraviolet ablation of molecules, and/or printing by mechanical stamping, and/or require a polymer layer tens of nanometers (nm) in thickness, which changes the optical quality of the substrate.

Thus, there is a need in the art for affordable, facile, equipment insensitive, reproducible methods for cell patterning on durable substrates such as glass and plastic that do not decrease the optical quality of the substrate, as well as for the cell patterning substrates themselves. Most surface modification processes for glass and silicon wafers are not amenable to plastic due to the nature of the harsh solvents used. Thiols are unsuitable for coating on plastics as they require a coinage metal for forming a coordination bond with the substrate. Silanes, though amenable to coating on plastics, require a hydroxylated surface, such as presented by glass and silicon, to form a covalent bond with the substrate.

Thus, in one aspect, the present invention provides novel methods for making a substrate for selective cell patterning. In one embodiment, the method comprises
  a) providing a substrate with a surface, wherein the surface contains reactive hydroxyl groups;
  b) contacting the hydroxyl groups on the surface of the substrate with a bifunctional molecule comprising a hydroxy-reactive moiety and a nucleophilic moiety to form a monolayer;
  c) applying a stencil to the substrate;
  d) applying an electrophilic cell repulsive moiety to exposed regions of the monolayer to form a covalent bond between the cell repulsive moiety and the bifunctional nucleophile deposited in step b to form cell repulsive locations;
  e) removing the stencil; and
  f) applying cell adhesive molecules to the substrate to produce cell binding locations, wherein the cell adhesion molecules bind the substrate only in positions that were contacted by the stencil.

In another embodiment, the method comprises
  a) providing a substrate with a surface, wherein the surface comprises reactive hydroxyl groups on the surface of the substrate;
  b) contacting the hydroxyl groups on the surface of the substrate with a bifunctional molecule comprising a hydroxy-reactive moiety and a nucleophilic moiety to form a monolayer
  c) applying a stencil to the substrate;
  d) applying cell adhesive molecules to exposed regions on the monolayer to produce cell binding locations;
  e) removing the stencil; and
  f) applying an electrophilic cell repulsive moiety to the substrate to produce cell repulsive locations, wherein the cell repulsive moiety forms a covalent bond with the bifunctional nucleophile deposited in step b only in positions that were contacted by the stencil.

The surface reactive hydroxyl groups can either be naturally occurring, or can be introduced via any technique known in the art. For example, polymer or glass can be oxidized so that they present surface hydroxyl groups, which react with organosilanes to produce covalent Si—O-substrate (siloxane) linkages. (U.S. Pat. No. 5,077,085).

In a preferred embodiment, oxidation is accomplished by oxygen plasma treatment, which can be achieved using oxygen doped radio frequency glow discharge. This discharge is accomplished with an instrument that can produce charged particles (electrons and positive ions) that interact with the background gas (oxygen), to produce free radicals under the time-varying electric field in radio frequency. The sample is placed into a cylindrical reactor, a minimal amount of oxygen gas is introduced, and charged particles are evolved between parallel-plated electrodes resulting in the cleavage of the $O_2$ bond. After this cleavage, high-energy free radicals can insert themselves into the polymer backbone resulting in the formation of various oxygen moieties, among which are hydroxyl groups. (U.S. Pat. No. 5,357,005; U.S. Pat. No. 5,132,108).

As used herein, the bifunctional molecule comprises
(a) a hydroxyl-reactive electrophile, including but not limited to silanes, carboxymethyl groups, succinimides, succinimidyl succinates, benzotriazole carbonates, glycidyl ethers (or epoxides), oxycarbonylimidazoles, p-nitrophenylcarbonates, aldehydes, isocyanates, and tresylates; and
(b) a nucleophile, including but not limited to sulfhydryl groups, amine groups, hydroxyl groups, or proteins or fragments thereof, peptides, and synthetic ligands for cell surface receptors, wherein the nucleophile can bind to other molecules and/or cells.

In one embodiment, the bifunctional molecule comprises an organosilane, wherein silane is the electrophile, and the nucleophile includes, but is not limited to sulfhydryl groups, amine groups, hydroxyl groups, or proteins, peptides, and synthetic ligands for cell surface receptors, wherein the nucleophile can bind to other molecules and/or cells. As used herein, organosilanes fall into a larger class of molecules, which have the capability of forming self-assembled (SA) films. The general form of this molecule comprises $R_nSiX_{4-n}$, where n=1,2, or 3; X=Cl, $OCH_3$, or $OC_2H_5$, and R is the nucleophile as described above.

In a preferred embodiment, the bifunctional molecule comprises an aminosilane, wherein silane is the electrophile that attaches to the surface hydroxyl groups, and an amine group is the nucleophile that can bind to other molecules and/or cells.

In a more preferred embodiment, the aminosilane is selected from the group consisting of methoxy or ethoxy silanes, which include but are not limited to trimethoxysilylpropyldiethylenetriamine, trimethoxysilylethylenediamine, aminopropyl-triethoxysilane, trimethoxyaminopropylsilane, or chlorosilanes such as trichlorosilylethylenediamine, aminopropyltrichlorosilane. In a most preferred embodiment, the amino silane is trimethoxysilylpropyldiethylenetriamine.

As used herein, a cell adhesive molecule includes compounds that: (1) introduce charge; and/or (2) are polar; and/or (3) contain sulfur and/or amines; and/or (4) are capable of tethering cells or other cell binding moieties, such as proteins, peptides, and synthetic ligands for cell surface receptors, thereby creating a cell binding location.

As used herein, the term cell repulsive moiety includes compounds that are capable of directly inhibiting cell binding, or that bind to other moieties which inhibit cell binding to the location, including polyethylene glycol (PEG) and other oxygen-rich compounds, sugars, hydrogels, extremely hydrophilic surfaces, or extremely hydrophobic surfaces.

In all of these embodiments, the cell adhesive molecule and/or cell repulsive moiety can be applied to the substrate via solution or vapor phase deposition. In a preferred embodiment, vapor deposition of the cell adhesive molecule and/or cell repulsive moiety is utilized. For example, a por phase deposition of various silanes has been demonstrated. (Tripp et al., Langmuir 8:1120–1126 (1992); Moses et al., Analytical Chemistry 20:4 (1978) In most cases, rather than adding the sample to a solution of silane, a hydroxylated surface is placed in the presence of vaporized silane (achievable by traditional vacuum techniques). The reaction takes place at the surface and results in self-assembled monolayers similar to that of silane solution deposition.

A wider range of cell adhesive molecules and cell repulsive moieties can be used with vapor phase deposition, because a solvent is not needed. For example, many silane solvents would dissolve the polymeric substrate and destroy its optical quality. In this embodiment, the method circumvents the use of solvents altogether.

In another preferred embodiment, the cell repulsive moiety comprises an amine-reactive moiety, including but not limited to 2,2,2-trifluoroethanesulfonyl chloride (tresyl chloride)-activated polyethylene glycol (PEG), polyvinylpyrrolidone, polyvinylalcohol, or any other amine-reactive extremely hydrophilic compound such as sugars (mannitol) or PEG, where the amine-reactive part can include, but is not limited to, carboxymethyl groups, succinimides, succinimidyl succinates, benzotriazole carbonates, glycidyl ethers (or epoxides), oxycarbonylimidazoles, p-nitrophenylcarbonates, aldehydes, isocyanates, and tresylates; or any amine-reactive extremely hydrophobic compound such as tridecafluoro-1,1,2,2-tetrahydrooctyl groups (13f) where the amine-reactive part can include, but is not limited to carboxymethyl groups, succinimides, succinimydil succinates, benzotriazole carbonates, glycidyl ethers (or epoxides), oxycarbonylimidazoles, p-nitrophenylcarbonates, aldehydes, isocyanates, and tresylates. In a most preferred embodiment, the amine-reactive cell repulsive moiety comprises tresyl chloride-activated polyethylene glycol ("tresyl-chloride activated-PEG").

The chemistry of the tresyl-activated PEG can be used to regulate surface hydroxyl, amine, or sulfhydryl groups. Tresyl chloride will allow stable linkages to be formed between the nucleophile and the initial hydroxyl, amine, or sulfhydryl group carrying carbon. In a preferred embodiment, PEG is attached to a tresyl group for reaction with surface aminosilane groups.

In these preferred embodiments, cell adhesive cues can be defined by the use of a stencil, which has no size constraints. Cell repulsive cues, which also can be defined by the stencil, are tethered to an aminosilane monolayer. The cell binding locations may optionally be coated with cell adhesive proteins, protein fragments, or peptides, and seeded with cells resulting in a patterned array of cells.

This hydroxylated substrate is contacted with a bifunctional molecule comprising an electrophile and a nucleophile. This modified substrate is contacted with a textured elastomeric substrate (herein referred to as a 'stencil'), such as rubber, polyurethanes and poly(dimethyl) siloxanes ("PDMS"), to form a hermetic seal between defined regions of the stencil and the modified substrate. In a preferred embodiment, the stencil comprises PDMS. These materials are quite affordable, providing a significant benefit over traditional UV photolithography methods that employ a costly, high energy laser apparatus. (U.S. Pat. No. 5,077,085).

The stencil comprises a physical mask that enables physical protection of defined regions of the underlying substrate from the subsequent solution or vapor phase deposition of the cell repulsive or cell adhesive moiety. This disclosed method of using a 'physical mask' distinguishes itself from existing art that relies on the use of an 'optical mask' (Dulcey et al., Science 252:551 (1991) and U.S. Pat. Nos. 5,965,305 and 5,391,463) or 'contact imprinting' (U.S. Pat. Nos. 5,512,131 and 5,776,748). The use of optical masks for protecting or de-protecting defined regions of a substrate is limited to the use of photoactivatible chemistries and/or photolabile molecules. The use of 'contact imprinting' is limited to solution phase transfer of materials onto a surface while not enabling 'protection' or 'de-protection' of defined regions of the surface. Further, contact imprinting does not enable reproducible transfer of controlled amounts of material onto the surface. The use of a 'stencil', as disclosed in this invention, allows for protection of a region of the substrate to enable modification of unprotected regions with solution or vapor phase chemistries not limited to photoreactive/photolabile molecules.

The present invention is not constrained to one particular kind of substrate. The tethering chemistry of the primary monolayer, or the organosilane, is such that it reacts with surface hydroxyl groups. These hydroxyl groups can be introduced on the surface of virtually any plastic and glass by low temperature plasma treatment. The secondary tethering chemistry, tresyl chemistry, can react with surface amines, hydroxyl, and sulfhydryls, making it possible to attach to a wider array of surface chemistry. The desired effect is also achievable with high density surface hydroxyl groups, (which may eliminate any silane treatment). (Dust, Macromolecules, 1990. 23:3742–3746; U.S. Pat. No. 5,330, 911) All of these benefits make the disclosed method of patterning on glass and plastics affordable, facile, and accurate.

The benign nature of the chemistry employed makes it attractive for biological applications, allowing the array to be prepared on glass and any thermoplastic and thermoset of choice including, but not limited to poly(styrene), poly (olefin), poly(dimethyl) siloxane (PDMS), poly(carbonate), poly(vinyl) chloride, poly(ethylene), poly(ethylene) terapthalate, Teflon, and fluoronated ethylene co-poly(propylene) (FEP). The present methods also have the ease and flexibility to be applied to polymeric and glass substrates using the same method. Plastics such as poly(styrene), acrylics, and poly(olefin) have benefits over glass, ceramics and metals because of their affordability, flexibility of shape and size, ease of engineering, durability, low cost and control over its optical quality. The plastics are easily obtained at a minimal cost, can be molded into almost any shape conceivable, and are durable.

The present methods for preparing a substrate for selective cell patterning are more reproducible than are methods that employ contact printing, because there is less opportunity for operator error. There is operator dependence when contact printing due to the subjectivity of applying the stamp to the substrate (force by which the stamp is depressed, amount of solution on the stamp) and so the results will vary. (U.S. Pat. No. 5,776,748) The present method of using a stencil for masking while performing solution or vapor phase deposition of the cell adhesive molecules and/or cell repulsive moieties is operator independent, thus providing a scalable and manufacturable process.

The instantly disclosed method of cell patterning has a marked advantage over prior thiol chemistry. Previous technology of contact printing with thiols not only introduces operator error, but also requires a thin layer of gold to be evaporated on the surface of the tissue culture substrate. Due to the high temperature involved with gold evaporation, most plastics cannot be used. Optical quality is constrained and fluorescence light is absorbed due to the added layer of gold, which reduces the quality of information gathered when conducting cell-based screening. In addition to a lower optical quality, there is a high cost associated with gold coating. Furthermore, silane linkages are covalent, and are not subject to degradation, as are thiols on gold, which degrade over time due to impurities and the fact that a thiol bond is coordinate and not covalent. The methods of the present invention permit cell patterning on an optically clear substrate and give the added option of control over the substrate, so that one has the freedom to choose the most superior affordable plastic or glass for optical quality.

In a particular embodiment of the present method, oxygen plasma is used to activate the surface in the case of poly (styrene) and poly(olefin), and acid washing is used to activate the surface in the case of glass. Both surfaces can be further incubated with a mildly acidic alcoholic solution of aminosilane featuring a primary amine on the terminating end of the tethered molecule. Following silane treatment, a stencil is applied to the substrate. An aqueous solution of tresyl chloride-activated PEG is applied to the substrate around the stencil resulting in regions of exposed amine, and regions of PEG in carefully controlled proximity to one another. After surface modification, the surface can be primed with cell adhesive proteins, protein fragments, or peptides to speed the cell adhesion process. (U.S. Pat. No. 5,874,219).

In another aspect, the present invention provides novel patterned substrates for cell culture. In one aspect, the invention provides cell patterning substrates, comprising:

1. at least a first portion having a reactive surface to which a plurality of cell adhesive molecules are coupled;
2. and at least a second portion having an exposed surface to which a plurality of cell repulsive moieties are coupled; wherein the cell adhesive molecules are selected from the group consisting of silanes, and wherein the cell repulsive moieties comprise tresylchloride activated poly(ethylene) glycol.

In a preferred embodiment, the silane comprises $R_n SiX_{4-n}$, where n=1,2, or 3; X=Cl, $OCH_3$, or $OC_2H_5$; R=a nucleophile, including but not limited to sulfhydryl groups, amine groups, hydroxyl groups, charged groups, polar groups, or proteins, protein fragments, peptides, and synthetic ligands for cell surface receptors, wherein the nucleophile can bind to other molecules and/or cells. In a preferred embodiment, the silane is an aminosilane. In a more preferred embodiment, the aminosilane is selected from the group consisting of methoxy or ethoxy silanes, which include but are not limited to trimethoxysilylpropyldiethylenetriamine, trimethoxysilylethylenediamine, aminopropyltriethoxysilane, trimethoxyaminopropyl-silane, or chlorosilanes such as trichlorosilylethylenediamine, aminopropyltrichlorosilane. In a most preferred embodiment, trimethoxysilylpropyldiethylenetriamine is used.

In another embodiment, the substrate further comprises cell adhesive proteins, protein fragments, or peptides, including but not limited to fibronectin, laminin, collagen, vitronectin, osteopontin, RGD peptides, RGDS peptides, YIGSR peptides. The strength of cell adhesion to the cell adhesion promoters can be modified by varying the composition of the cell adhesive proteins, protein fragments, or peptides. In a further embodiment, the substrate further comprises cells bound to the cell binding locations, either directly or indirectly via cell adhesive proteins, protein fragments, or peptides. Any cell type may be used, including prokaryotic, eukaryotic, and archaebacterial cells.

The cell binding locations according to the various methods and substrates of the invention can be as small as the diameter of a single cell and as large as several hundred cell diameters. The distance between cell binding locations (i.e.: the cell repulsive locations) is cell size dependent, but is sufficiently large so that a cell cannot bridge the gap between cell binding locations (i.e.: 1 cell diameter), unless a particular application calls for interaction of cells in different cell binding locations.

In a further embodiment, the various cell patterning substrates are mated with a fluid delivery system to provide fluid and/or reagent flow to the cell binding location. In a preferred embodiment, the fluid delivery system is that described herein.

In another embodiment, the cell patterning substrate comprises a cell patterning substrate made by the methods of the invention, as disclosed above.

This aspect of the present invention may be better understood with reference to the accompanying preferred embodiments that are intended for purposes of illustration only and should not be construed to limit the scope of the invention, as defined by the claims appended hereto.

Materials and Methods:

Reagents and instrumentation that can be utilized in carrying out the methods of the invention include, but are not limited to, 60 and 35 mm petri dishes, microplates, thermoplastics, poly(olefin), plasma cleaner/sterilizer, digital convection gauges, trimethoxysilylpropyldiethylenetriamine, and 2,2,2-trifluoroethanesylphonyl-poly(ethylene)$_{5000}$ glycol.

Poly(styrene), poly(olefin), or other thermoplastic substrates such as poly(esters) and poly(ether) are oxygen plasma treated inside a plasma cleaner using the following method. Substrates are placed inside the glass tube chamber and the chamber is evacuated to a pressure of ~200 mtorr as indicated by a convection gauge. Oxygen is pulsed in through a regulation valve and the chamber is evacuated again to a pressure of ~200 mtorr. The above oxygen pulse is repeated 2 more times. After the last oxygen pulse, the gas is allowed to bleed constantly into the chamber, and the final equilibrium pressure (with the oxygen bleed valve on and the vacuum pump activated) should be ~300 mtorr. After the proper pressure is reached, the voltage switch is turned up to HI (100W) and the substrates are treated for 25 minutes.

Glass surfaces are activated using the following method. A 1M KOH solution is prepared in double distilled/deionized (DI) water. The glass surfaces are incubated for 10 minutes in 1M KOH. After 10 minutes, the substrates are rinsed 3 times in double DI water. Coverslips are soaked in HCl:MeOH (1:1) for 30 minutes. After the incubation, the coverslips are rinsed in double DI water, and transferred into a concentrated bath of sulfuric acid for 30 minutes, followed by 3 rinses with double DI water. The coverslips are then boiled in distilled water for 15 minutes, and the surfaces blown dry with a nitrogen gun.

Aminosilane treatment is the same for glass, poly(styrene), and poly(olefin). A 1% solution of trimethoxysilylpropyldiethylenetriamine is prepared in mildly acidified methanol (94% methanol, 5% water, and 0.004% glacial acetic acid) and incubated with the substrates for 15 minutes. Following silane treatment, the substrates are rinsed with methanol and baked in a 80° C. oven for 30 minutes.

The PDMS stencil is applied to the aminated glass or poly(styrene) (this embodiment includes but is not limited to 50, 100, 200 micron and 500 micron spots). Pressure is applied until the stencil makes a tight seal.

Tresyl-PEG treatment is the same for glass and poly (styrene). After stencil application, a 0.12M sodium bicarbonate solution is prepared in water. A 25% solution of tresyl-PEG (by weight) is prepared in the bicarbonate. The solution is applied around the stencil and allowed to pool around the PDMS, resulting in the liquid touching only exposed aminated surface areas. The substrates are incubated for 4 hours.

Following PEG treatment, the surfaces are rinsed with the 0.12M sodium bicarbonate solution. The substrates are allowed to incubate for 2 hours and rinsed under a stream of PBS. The substrates ("partially active") can be stored for more than 30 days in a dry box before protein coating and cell incubation.

As used herein, the term "partially active" substrates are glass or plastic substrates chemically and/or texturally modified to yield a patterned array of protein binding locations separated by cytophobic domains.

Protein Coating
1. The partially active substrates are incubated in a protein, protein fragment, or peptide solution, including but not limited to fibronectin, laminin, collagen, vitronectin, osteopontin, or fragments thereof, as well as RGD peptides, RGDS peptides, YIGSR peptides, at concentrations ranging from 1 µg/ml to 25 µg/ml, for 1–2 hours.
2. Post-incubation, the substrates are rinsed in a stream of PBS.
3. The protein/peptide coated substrates are lyophilized to preserve the protein/peptide structure. These "quasi-active" substrates can be stored in a dry box for >30 days. The silane linkages are covalent and not subject to degradation, as are thiols on gold, which degrade over time due to impurities and the fact that a thiol bond is coordinate and not covalent. As used herein, the term "quasi-active" substrates are glass or plastic substrates chemically and/or texturally modified to yield a patterned array of protein or peptide-rich domains separated by cytophobic domains.

Cell Seeding
1. Cells are prepared for seeding by standard techniques.
2. Partially active or quasi-active substrates are re-hydrated in cell culture medium for 5 minutes.
3. The cells are incubated at any desired seeding density with the partially or quasi active substrate for 30 minutes to 2 hours (depending on the cell type) in complete cell culture media at 37° C. and 5% $CO_2$.
4. The "fully active" substrates, arrayed with the cells, can then be used for cell screening assays. After cryopreservation or room temperature desiccation the fully active substrates can be stored long term. As used herein, the term "fully active" substrates are glass or plastic substrates chemically and/or texturally modified to yield a patterned array of cells separated by cytophobic domains. They can be derived from either partially or quasi-active substrates, although the use of quasi-active substrates is preferred.

EXAMPLE 5

Patterned Stem Cell and Differentiated Cell Substrates

Stem cells possess the intrinsic ability to: (1) undergo self renewal, or (2) produce differentiated progeny. Extrinsic factors (culture medium, growth factors, physico-chemical cues from the surrounding cellular milieu) mediate the developmental fate of stem cells. Tissue specific stem cells, also called determined stem cells, also exhibit pluripotency but not totipotency. Determined stem cells provide the ability to access a primary, partially committed cell that can be driven to either self-replication in culture, or selectively differentiated into a multitude of tissue specific progeny that in-vitro are close, genotypically and phenotypically, to the whole organism, in contrast to immortalized cells that are both genotypically and phenotypically far removed from their precursor cells in the organism.

The pharmacological relevance of using stem cell derived tissue-specific progeny over immortalized cells results from the genotypic and phenotypic match afforded by the former.

As a new chemical compound goes from being identified as "active" in a primary drug screen, it must pass through numerous tests designed to assess its pharmacological profile. Indices of bio-relevance such as cytotoxicity, bioavailablity, and specificity are evaluated together with potency to generate this profile, and require the use of cells genotypically and phenotypically matched to the organism. This increases the probability that the compound will be therapeutically relevant when it gets to the clinic beyond the animal testing stage. The use of primary cells (hepatocytes, neurons, chondrocytes, myocytes, adipocytes) are well documented in secondary and tertiary testing. However, the difficulty in obtaining the proper cells (access or amount), and culturing them in sufficient quantity to cover assay capacity remains a major problem. The use of stem cell derived primary cells can afford a solution to both higher relevance and a source of primary cells.

Other work has focused on the production of spatially oriented neo-vascular capillaries from endothelial cells that are bound to cell adhesion promoters patterned on a substrate. (Rudolph et al., U.S. Pat. No. 5,721,131) However, the resulting substrate contained only a single type of differentiated cell, because the method did not permit individually addressing the cell binding locations with differentiating reagents.

The present invention provides methods for preparing patterned cell substrates comprising a multitude of terminally differentiated cells from an ordered array of stem cells, as well as the substrates themselves. The use of these patterned cell substrates for drug discovery increases the confidence level and relevance of the in-vitro pharmacological screening data for extrapolation to in-vivo settings.

The methods and substrate of the present invention mimic events in developmental biology: formation of committed mature or terminally differentiated cells from stem cells using controlled delivery of differentiation factors (including, but not limited to extracellular matrix (ECM) derivatized substrates, autocrine/paracrine/endocrine factors, etc.). Prior technology teaches induction of cellular heterogeneity by "peppering" a cell substrate surface with a multitude of cell adhesive domains enabling selective adhesion of one or more immortalized, genotypically and phenotypically distinct cell types from solution. The limited number of "cell-specific cell adhesive moieties" limits the number of distinct cell types attainable on a single substrate. Prior technology does not take advantage of the intrinsic ability of stem cells to differentiate into a multitude of differentiated progeny.

In contrast, the present invention teaches induction of cellular heterogeneity on any substrate of choice (ceramics, metals, polymers, composites etc.) by the controlled differentiation of population(s) of stem cells into a multitude of differentiated cells. The controlled differentiation enables creation of "patterns of mixed cell types" in any number of variations and geometry. The present invention also enables creation of organ specific and tissue specific cell substrates that are close in genotypic and phenotypic relevance to the organism of choice, as well as substrates that model in vivo interactions between tissue specific and/or organ specific cells. This enables creation of a cell based screening platform capable of providing information with greater relevance to the organism or systemic level.

The preparation cell substrate of the present invention requires providing a patterned stem cell substrate, comprising:
  (a) a substrate surface;
  (b) a plurality of cell binding locations on the surface, wherein a cell binding location comprises:
    (1) one or more cell adhesive molecules; and
    (2) a plurality of stem cells bound to the cell adhesive molecules; and
  (c) a plurality of cell repulsive locations on the surface, wherein the cell repulsive locations comprise a cell repulsive moiety, wherein individual cell binding locations are separated by cell repulsive locations.

A single type, or multiple types of stem cells are bound to the cell binding locations in a patterned array. As used herein, the term "patterned stem cell substrate" means that the stem cells are arrayed on the substrate in a controlled pattern. The stem cells can comprise a single class of stem cells, or may comprise multiple stem cell types, in which case the positioning of the different stem cell types is also controlled.

As used herein, the term "stem cells" refers to any cell type that possesses the ability to produce at least one type of differentiated progeny. As such, stem cells include, but are not limited to cells capable of differentiation into any cell type and self-renewal (pluripotent cells); cells capable of differentiation into any cell type but not self-renewal (totipotent cells); cells capable of self-renewal and differentiation into many cell types (broad potential; multipotent stem cells), cells capable of limited self-renewal and differentiation into limited types of cells (progenitor cells); and cells that have committed to differentiation into a specific cell type, but have not yet completed differentiation (committed progenitor cells). (See, for example, Gage et al. Science 287:1433–1438 (2000).) In various embodiments, the stem cells are selected from the group consisting of neural stem cells, neural progenitor cells, glial progenitor cells, mesenchymal stem cells, hematopoietic stem cells, epithelial stem cells, hepatic stem cells, embryonic stem cells, or combinations thereof. Reference to specific classes of stem cells is provided below:

Hepatic stem cells are reviewed in Thorgeirsson, FASEB J 10:1249 (1996). Examples of hepatic stem cells include, but are not limited to, SEC cells, oval cells, as well as cultured WB-F344 cells, L2039 cells, and RLEΦ13 cells (Coleman et al., Am. J. Pathol. 151:353 (1997); Omori et al., Hepatology 26:720 (1997); Fiorino et al., In Vitro Cell Dev. Biol. Anim. 34:247–258 (1998); Agelli et al., Histochem. J. 29:205–217 (1997); Brill et al., Proc. Soc. Exp. Biol. Med. 204:261–269 (1993)).

Neural stem and progenitor cells: Examples of neuronal stem and progenitor cells include, but are not limited to, NT-2 cells (Pleasure et al., J. Neuroscience 12:1802–1815 (1992)), and those described in Gage, Science 287:1433–1438 (2000); Gritti et al., J of Neuroscience 16:1091–1100 (1996); Frederiksen et al., Neuron 1:439 (1988); Reynolds and Weiss, Science 255:1707 (1992); Davis and Temple, Nature 372:263 (1994); McKay, Science 276:66–71 (1997);. Vicario-Abejon et al., Neuron 15:105 (1995); Johe et al., Genes and Develop. 10:3129–3142 (1996); and U.S. Pat. Nos. 5,824,489; 6,001,654; 6,033,906).

Glial progenitor cells: Examples of glial progenitor cells include, but are not limited to SNB-19 cells and oligodendrocytes that can be diferentiated in vitro (Raible et al., J. Neurosci. Res. 34:287–294 (1993); (Welch et al., In Vitro Cell. Dev. Biol.-Animal 31:610–616 (1995)).

Mesenchymal stem cells are pluripotent progenitor cells that possess the ability to differentiate into a variety of mesenchymal tissue, including bone, cartilage, tendon, muscle, marrow stroma, fat and dermis. Such stem cells include, but are not limited to, C2C12 cells (Teboul et al., J. Biol. Chem. 270:28183–28187 (1995); Nishimura et al., J.

Biol. Chem. 273:1872–1879 (1998)); and cells such as those described in U.S. Pat. Nos. 5,486,359; 5,827,740; 5,942,225; 6,022,540.

Hematopoietic stem cells refer to any hematopoietic pluripotent progenitor cells capable of giving rise to a variety of differentiated hematopoietic cell types. Cell types within this definition include, but are not limited to CD34$^+$ bone marrow mononuclear cells (BMMC) (Berardi, et al., Blood 86:2123–2129, 1995), PBSC (Fritsch, et al., Bone Marrow Transplantation 17:169–178, 1996), cobblestone area forming cells (CAFC) (Lemieux, et al., Blood 86:1339–1347, 1995) and 5-FU BM cells (Alcorn and Holyoake, Blood Reviews 10:167–176, 1996); U.S. Pat. No. 5,807,744).

Epithelial stem cells refer to cells that are long-lived, relatively undifferentiated, have a great potential for cell division, and are ultimately responsible for the homeostasis of epithelium. Cells of this type include, but are not limited to, those described in U.S. Pat. No. 5,556,783; U.S. Pat. No. 5,423,778; Rochat et al., Cell 76:1063 (1994); Jones et al. Cell 73:713 (1993); Jones et al., Cell 80:83 (1995)) and Slack, Science 287:1431–1433 (2000).

The cell adhesive molecules of this aspect of the invention can comprise any compound that is capable of supporting stem cell adhesion to the substrate, such as those described above, including cell adhesion molecules, co-polymer blends of extracellular matrix proteins or protein fragments such as RGD-containing peptides, silanes or thiols. In one embodiment, aminosilanes, such as methoxy or ethoxy silanes as disclosed above, are used.

The cell repulsive moieties comprise moieties that are capable of directly inhibiting cell binding, or that bind to other moieties which inhibit cell binding to the cell repulsive location, including but not limited to polyethylene glycol (PEG) and other oxygen-rich compounds, sugars, hydrogels, extremely hydrophilic surfaces, or extremely hydrophobic surfaces, as described above.

The cell binding locations may also comprise inhibitors of uncontrolled differentiation of the stem cell, which can comprise any compound known in the art to prevent uncontrolled stem cell differentiation. Such compounds include, but are not limited to self-assembled monolayers of thiols or silanes coupled to cell adhesive ligands, which are utilized to enable the creation of cell binding locations, while preventing their uncontrolled differentiation. Another example is the addition of protease thrombin to cultures of the Neuro2A neuroblastoma cell line, which inhibits differentiation of the cells into neurite-containing neuronal cells. (Gurwitz et al., Proc. Natl. Acad. Sci. 85:3440–3444 (1988)) Thus, the cell binding promoter can also serve as an inhibitor of uncontrolled differentiation. Alternatively, the cell binding locations are covered with a feeder layer of cells to inhibit uncontrolled stem cell differentiation.

The substrate of this aspect of the invention can be made of any material known in the art, including but not limited to plastics, glass, ceramics and metals. Preferably, such patterned substrates are made on commercially viable plastic substrates such as polystyrene or poly(olefin). In a preferred embodiment, the substrates possess 100 μm–500 μm diameter circular cell binding locations separated by edge-to-edge spacing ranging from 25 μm to 125 μm. The overall footprint on the substrate will match the format of 96, 384, and 1536 well microplates, and be approximately 150-fold smaller in surface area compared to 1536 (32 rows×48 columns), 384 (16 rows×24 columns), and 96 wells (8 rows×12 columns) microplates.

In a further aspect, the present invention provides a patterned differentiated cell substrate comprising:

(a) a substrate surface;
(b) a first plurality of cell binding locations on the surface comprising:
 (i) one or more cell adhesive molecule;
 (ii) a first differentiated cell type;
(c) a second plurality of cell binding locations on the surface comprising:
 (i) one or more cell adhesive molecule;
 (ii) a second differentiated cell type; wherein the first and second differentiated cell types are arrayed on the substrate in a controlled pattern; and
(d) a plurality of cell repulsive locations on the surface, wherein the cell repulsive locations comprise a cell repulsive moiety, wherein individual cell binding locations are separated by cell repulsive locations.

As used herein, the term "patterned differentiated cell substrate" means that the differentiated cells are arrayed on the substrate in a controlled fashion, wherein the terminal differentiation is achieved post-patterning.

In one embodiment, the differentiated cells are derived from stem cells that were selectively differentiated on the substrate. In this embodiment, the stem cell type is selected from the group consisting of neural stem cells, neural progenitor cells, glial progenitor cells, mesenchymal stem cells, hematopoietic stem cells, epithelial stem cells, hepatic stem cells, embryonic stem cells, or combinations thereof. Alternatively, differentiation can be initiated prior to plating the cells (committed progenitor cells) on the substrate. One of skill in the art will be able to envision many permutations of this embodiment, including but not limited to the following:

1. Selective differentiation of a single stem cell type into two or more differentiated cell types in predetermined locations on a single substrate.
2. Selective differentiation of two or more stem cell types arrayed on a single substrate to generate two or more differentiated cell types.
3. Sequential, selective differentiation of a single or multiple stem cell types, whereby a single differentiated cell type is produced first, followed by selective differentiation of the stem cell type(s) in other cell binding locations.

Thus, in a preferred embodiment, the present invention results in a substrate with multiple types of differentiated cell types arranged in a pre-determined manner. The number of different cell types that can be arrayed is limited only by the differentiation potential of the stem cell, since the various cell binding locations can be individually addressed with differentiating agents, using devices including, but not limited to microspotters, and fluid delivery system such as, but not limited to those disclosed herein, and in U.S. Pat. Nos. 5,858,188; and 6,007,690. Selective addressing of the stem cells with differentiating agents enables controlled differentiation into the progeny of choice. In a preferred embodiment, the fluid delivery system of the present invention is combined with the patterned cell substrate to produce a microfluidic cassette, which can deliver differentiating compounds to the patterned undifferentiated stem cells.

In a preferred embodiment, the first and second differentiated cell types are cell types found in a single tissue, including but not limited to brain, vascular tissue, skin, pancreas, kidney, liver, lung, heart, intestine, and stomach.

In another preferred embodiment, the first and second differentiated cell types are cell types that are found in different tissues that interact in vivo, including but not limited to peripheral nerve-smooth and/or skeletal muscle; epithelial tissue-smooth muscle; vascular endothelium-smooth muscle; glial cells-endothelial cells of blood capillaries; adipose cells-axons of peripheral nerve cells and/or Schwann cells; and pancreatic B cells-pancreatic A cells.

In another preferred embodiment, the first and second differentiated cell types are selected from the group consisting of glial cells, neurons, adipocytes, smooth muscle cells, skeletal muscle cells, osteoblasts, chondrocytes, stromal cells, and myocytes.

In various most preferred embodiments, (a) the first differentiated cell type derived is a glial cell, and the second differentiated cell type is a neuronal cell, thus producing a cell substrate model for the brain; (b) the first differentiated cell type is an adipocyte and the second differentiated cell type is a muscle cell; (c) the first differentiated cell type a neuronal cell and the second differentiated cell type is a muscle cell.

In a further preferred embodiment, the patterned stem cell substrate or the patterned cell substrate is mated with a fluid delivery system chamber to form a cassette, wherein the fluid delivery system delivers reagents to the stem cells or differentiated cells, and comprises:
  (i) a plurality of domains matching the cell binding locations on the surface of the substrate, and
  (ii) microfluidic channels that supply reagents to the cell binding locations.

As used herein, "reagents" include differentiating agents, as well as cell culture medium and any cell culture supplements for cell culture, and test compounds for screening the effects of drug compound libraries and toxins on the cells.

In a most preferred embodiment, a single microfluidic channel supplies fluid to a single cell binding location on the substrate, to provide separate fluid flow to each cell binding location, thereby permitting selective differentiation of the stem cells, and/or selective treatment of the stem cells or differentiated cells in one or more cell binding locations with a test agent of choice.

In another aspect, the present invention provides a patterned differentiated cell substrate made by a method of selective differentiation of patterned stem cells, wherein the method comprises:
  (a) providing a patterned stem cell substrate, comprising
    (1) a substrate surface;
    (2) a first plurality of cell binding locations on the surface comprising
      (i) one or more cell adhesive molecules;
      (ii) a first differentiated cell type;
    (3) a second plurality of cell binding locations on the surface comprising:
      (i) one or more cell adhesive molecules;
      (ii) a second differentiated cell type; wherein the first and second differentiated cell types are arrayed on the substrate in a controlled pattern;
  (b) selectively contacting the cell binding locations with differentiating agents to provide controlled differentiation of the stem cells into a progeny of choice, wherein the selective contacting produces a patterned differentiated cell substrate.

In a preferred embodiment, the patterned cell substrate is mated with a fluid delivery system as described above.

In further preferred embodiments of the above aspects, the stem cells and the resulting differentiated cells possess at least one luminescent reporter molecule, for use in cell screening assays to determine the distribution, environment or activity of the luminescent reporter molecules on or in the cells or within or between subcellular compartments of the cells, in response to a test agent of choice. A variety of such luminescent reporter molecules can be used in this aspect of the invention, including but not limited to those described in U.S. Pat. No. 5,989,835; pending U.S. patent application Ser. Nos. 09/031,271 (filed Feb. 27, 1998); 09/352,171 (filed Jul. 12, 1999); 09/293,209 (filed Apr. 16, 1999); 09/293,209 (filed Apr. 16, 1999); 09/398,965 (filed Sep. 17, 1999); 09/430,656 (filed Oct. 29, 1999); 09/513,783 (filed Feb. 24, 2000); Giuliano et al., Ann. Rev. Biophys. Biomol. Struct. 24:405–434 (1995); and Giuliano et al., Trends in Biotech. 16:135–140 (1998), all references incorporated by reference herein in their entirety.

The luminescent probes can be small molecules, labeled macromolecules, or genetically engineered proteins, including, but not limited to green fluorescent protein chimeras. As used herein, "luminescent" probes include fluorescent, luminescent, and chemiluminescent probes.

In another embodiment, only one of the differentiated cell types possesses a luminescent reporter molecule, and when an interaction occurs between the first and second differentiated cell types, only one of the cell types reports the interaction, via the luminescent reporter molecule.

The luminescently labeled reporter molecule may be expressed by or added to the cells either before, together with, or after contacting the cells with a test compound. For example, the reporter molecule may be expressed as a luminescently labeled protein chimera by transfected stem cells. Alternatively, the luminescently labeled reporter molecule may be expressed, isolated, and bulk-loaded into the stem cells, or the reporter molecule may be luminescently labeled after isolation. As a further alternative, the reporter molecule can be expressed by the stem cell, which is subsequently contacted with a luminescent label, such as a labeled antibody, that detects the reporter molecule.

Preferably, the luminescent reporter molecules in the first differentiated cell type are spectrally distinguishable from the luminescent reporter molecules in the second differentiated cell type.

The present invention also provides methods for selective stem cell differentiation, comprising providing a patterned stem cell substrate as disclosed above, and selectively contacting the cell binding locations with differentiating agents to provide controlled differentiation of the stem cells into the progeny of choice, wherein the selective contacting produces a patterned differentiated cell substrate. Any method known in the art for differentiating the stem cells into differentiated cells can be used. References providing conditions for differentiating the various stem cells into differentiated progeny can be found, for example, in the following references, which are incorporated by reference herein in their entirety:

Mesenchymal stem cells: U.S. Pat. No. 5,827,740 (adipogenic differentiation); U.S. Pat. No. 6,022,540 (osteogenic differentiation); U.S. Pat. No. 5,942,225 (osteogenic, chondrogenic, tendenogenic, marrow stromal cell, and myogenic differentiation); Cuenda et al., J. Biol. Chem. 274: 4341–4346 (1999) (C2C12 myogenic differentiation); Nishimura et al., J. Biol. Chem. 273:1872–1879 (1998) (C2C12 osteoblastic differentiation); Teboul et al., J. Biol. Chem. 270:28183–28187 (1995) (C2C12 adipogenic differentiation).

Neural stem and progenitor cells: U.S. Pat. No. 5,824,489 (neurons and glia); U.S. Pat. No. 6,001,654 (neurons and smooth muscle cells); U.S. Pat. No. 6,033,906 (glial cells); Pleasure et al., J. Neurosci. 12:1802–1815 (1992) (NTera2 differentiation into neurons);

Glial and neural stem and progenitor cells: Welch et al., In Vitro Cell. Dev. Biol.-Animal 31:610–616 (1995) (SNB-19 glial differentiation); U.S. Pat. No. 5,824,489 (neurons and glia).

Hematopoietic stem cells: Lawman et al., J. Hemather. 1:251–259 (1992); Huss, Stem Cells 18:1–9 (2000); Zhang et al., Blood 95:138–146 (2000); Zhang et al., Blood 92:118–128 (1998).

Hepatic stem cells: Brill et al., Proc. Soc. Exp. Biol. Med. 204:261–269 (1993); Brill et al., Dig. Dis. Sci., 44:364–371 (1999); Fiorino et al., In Vitro Cell Dev. Biol. Anim. 34:247–258 (1998).

In various preferred embodiments, the substrate is mated with a fluid delivery system as disclosed above, and the stem cells possess at least one luminescent reporter molecule that serves to identify the phenotype of the progeny of choice.

In these embodiments, the stem cells are contacted with differentiating agents, to effect differentiation of the transfected patterned cells into differentiated progeny, using the appropriate differentiating agents applied either homogeneously to the substrate (for single progeny) or selectively to specific cell binding locations (multiple progeny). Differentiation of a single stem cell type into different progeny, or of different stem cells into different progeny, permits the formation of substrates with cell binding locations that bear different cell types in any desired juxtaposition. In this way, simple to moderately complex models of cellular differentiation are used to prepare multicellular tissue-specific and organ-specific cell substrates for use in cell based analysis for drug discovery and life sciences.

In one model system, neuronal and glial stem cells are engineered to express fluorescent protein reporter molecules to measure the dynamics of their cytoskeletal proteins. The cytoskeleton has become a well-characterized and valid drug discovery target for which there are likely to be many lead compounds in the drug discovery pipeline at any one time. Each of the stem cell lines express spectrally distinct reporter molecules such that they can be patterned into separate locations within a cell array as well as be patterned together, (co-cultured) within the same location. Alternatively, the different stem cells may be patterned into separate locations, wherein the locations are in close enough proximity to permit interactions between the cells in the different locations. The latter two aspect allow the simultaneous measurement of drug responses of the two cell types in an organotypic context where the cells are allowed to interact as they would within the brain tissue of a living animal. Because the reporter molecules contained within each cell type are spectrally distinct, the platform detects and assigns function to each cell type within the co-culture.

In a second model system, a pluripotent cell line, mouse C2C12 cells, is engineered with a luminescent reporter molecule, patterned into microarrays, and differentiated into two cell types, skeletal muscle myocytes and adipocytes. In this case, the stem cells are engineered to express a luminescent reporter molecule of carbohydrate metabolic flux, including but not limited to reporters of the phosphorylation state of PFK-1 and PFK-2, the measurement of cellular ATP levels (energy charge), the ratio of oxidation-reduction cofactors such as $NAD^+/NADH$, and the concentration of the second messenger cAMP, that are measured both in time and in space within each cell type. For muscle and adipose cells, carbohydrate metabolism plays an important role in regulating the physiological function of each cell type; contraction and relaxation of the muscle cells and fat storage and mobilization in adipocytes. Therefore, this model system permits measurement of the effect of lead compounds on the same molecular pathway within two tissue types. Moreover, this multiple tissue type screening platform permits the efficient addressing of lead compound efficacy, specificity, and toxicology.

A third, more complex model system involves the co-cultivation of neuronal and skeletal muscle stem cells with both types being engineered to express spectrally distinct luminescent reporter molecules. The cells are patterned and differentiated on the substrate. The effect of lead compounds on the complex interaction of neurons and skeletal muscle cells is measured using the luminescent reporter molecules engineered into each cell type. The co-cultivation of differentiated neuronal and muscle cells permits direct measurement of excitation-contraction coupling events and the effects that lead compounds have on these events.

These approaches can be generalized to interactions between other tissue types and interactions between multiple cell types within an organ, including but not limited to peripheral nerve-smooth or skeletal muscle; epithelial tissue-smooth muscle; vascular endothelium-smooth muscle; glial cells-endothelial cells of blood capillaries; adipose cells-axons of peripheral nerve cells and Schwann cells; and pancreatic B cells-pancreatic A cells.

The present invention further provides methods for cell based screening, wherein the stem cells and/or differentiated cells possess at least one luminescent reporter molecule, for use in cell screening assays to determine the distribution, environment or activity of the luminescent reporter molecules on or in the cells or within or between subcellular compartments of the cells, in response to a test agent of choice. A variety of such luminescent reporter molecules can be used in this aspect of the invention, including but not limited to those described in U.S. Pat. No. 5,989,835; pending U.S. patent application Ser. Nos. 09/031,271 (filed Feb. 27, 1998); 09/352,171 (filed Jul. 12, 1999); 09/293,209 (filed Apr. 16, 1999); 09/293,209 (filed Apr. 16, 1999); 09/398,965 (filed Sep. 17, 1999); 09/430,656 (filed Oct. 29, 1999); 09/513,783 (filed Feb. 24, 2000); Giuliano et al., Ann. Rev. Biophys. Biomol. Struct. 24:405–434 (1995); and Giuliano et al., Trends in Biotech. 16:135–140 (1998), all references incorporated by reference herein in their entirety.

In this embodiment of the method, the patterned stem cell arrays and patterned differentiated cell arrays are used to analyze changes in the distribution, environment or activity of the luminescent reporter molecules on or in the cells or within or between subcellular compartments of the cells in response to a test compound. The cells are imaged and/or scanned using a cell screening system comprising an optical system with a stage adapted for holding a substrate containing cells, a detection device that is capable of creating a digital image, a means for directing fluorescence or luminescence emitted from the cells to the detection device, and a computer for receiving and processing data from the detection device. A preferred embodiment of such a device is disclosed in U.S. Pat. No. 5,989,835; and pending U.S. patent application Ser. No. 09/031,271 (filed Feb. 27, 1998), both references incorporated by reference herein in their entirety. Utilizing the cell screening system, luminescent signals from the reporter molecules are converted into digital data; and the digital data is used to determine changes in the distribution, environment or activity of the reporter molecules in response to the test agent.

Such digital data can be used to report the effect of a test compound on distribution of the reporter molecule between: cytoplasm-nucleus, cell membrane-cytoplasm, endoplasmic reticulum-Golgi apparatus, as well as to report on apoptosis; receptor internalization; transcription factor activation; protein kinase activation; protease activity; organelle structure, distribution, and function; macromolecule distribution; gene expression; microtubule cytoskeletal structure; actin cytoskeletal structure; nuclear shape; nuclear area; nuclear size; nuclear perimeter; mitochondrial potential; cell shape; cell motility; cell size; and cell perimeter. (For example, see U.S. Pat. No. 5,989,835; pending U.S. patent application Ser. Nos. 09/031,271 (filed Feb. 27, 1998); 09/352,171 (filed Jul. 12, 1999); 09/293,209 (filed Apr. 16, 1999); 09/398,965 (filed Sep. 17, 1999); 09/430,656 (filed Oct. 29, 1999); and 09/513,783 (filed Feb. 24, 2000).

The use of a fluid delivery system in the method, including but not limited to that disclosed above, or the use of automated precision instruments such as microspotters, permits the delivery of specific cell binding locations with a differentiating agent of choice.

EXAMPLES

Organotypic Differentiation Model Systems

Glial differentiation: Cells taken from a highly aggressive human glioblastoma tumor have been shown to grow indefinitely in culture and to exhibit altered morphological and growth characteristics in the presence of a differentiation agent. These cells, named SNB-19 (Welch et al., 1995), are engineered to express a luminescent reporter molecule (see below) and patterned onto cell substrates, either by themselves or in combination with neuronal stem cells. To induce differentiation, a mixture of 1 mM dibutyryl-cAMP and 1 mM isobutylmethyl xanthine (a phosphodiesterase inhibitor) is added to the culture, and the cells are allowed to incubate for 12–24 hours. These agents induce the cells to elaborate multiple processes that often interact with other glia in the same culture (Welch et al., 1995), as well as cause the cells to stop dividing.

The glial stem cells are transfected to express a green fluorescent protein (GFP)-glial fibrillary acidic protein (GFAP) chimera. GFAP is a component of the intermediate filament cytoskeleton, and is a major cytoskeletal protein found in glial stem cells and differentiated glia.

Neuronal differentiation: Several neuronal stem cell lines exist that can be used in the instant invention. NT2 cells from a human teratocarcinoma cell line (Pleasure et al., 1992) are unique in that they can be induced to differentiate into stable, post-mitotic human neurons, and they have been shown to be a vehicle for the expression of diverse gene products. (Pleasure et al., 1992) NT2 cells are engineered to express a blue fluorescent protein (BFP)-β-tubulin chimera. β-tubulin is a major component of the cytoskeleton. The cells are then patterned onto cell substrates, either by themselves or in combination with glial stem cells. To induce differentiation, NT2 cells initially enter a program of differentiation that begins with a two week treatment of retinoic acid ($10^{-5}$ M), mitotic inhibitors, and a specialized extracellular matrix. The partially differentiated cells are transferred to the substrates where they undergo the final stages of differentiation by elaborating processes that form axons and dendrites. The cells become post-mitotic, but retain the ability to express functional proteins, such as the luminescent protein reporter molecule.

Mixed glial-neuronal differentiation: NT2 stem cells in the final stages of differentiation are added with SNB-19 cells to the same substrate. After both cell types attach, the co-cultures are treated with 1 mM dibutyryl-cAMP and 1 mM isobutylmethyl xanthine. The two cell types are allowed to interact as they differentiate. Because the NT2 cells are committed to differentiation, the dibutyryl-cAMP has little to no effect on neuronal cell differentiation, and may even enhance it, since cAMP is known to induce the differentiation of several cell types.

Adipose and skeletal muscle tissue from a common stem cell: The mouse C2C12 cell line is pluripotent and has been shown capable of differentiating into skeletal muscle (Cuenda and Cohen, 1999), adipocytes (Teboul et al., 1995), and osteoblasts (Nishimura et al., 1998). The C2C12 cells are first engineered to express a luminescent reporter molecule of carbohydrate metabolism (see below). The cells are patterned onto substrates where the growth medium contains <1% calf serum. This large decrease in serum concentration (10% originally) induces the C2C12 cells, over a period of 24–48 hours, to stop dividing, fuse into elongated, multi-nucleated cells, and form contractile myotubes. To induce adipocyte differentiation, the cells are treated with a mix of 5 µM thiazolidinedione and 100 µM fatty acid (Teboul et al., 1995). Differentiation occurs after 24–48 hours and is accompanied by the slowing of cell growth and the uptake of fatty acids by the cells and their incorporation into lipid droplets.

The C2C12 cells are transfected with a reporter molecule comprising 6-phosphofructo-2-kinase/fructose-2,6-bisphosphatase (PFK-2), which plays a key role in balancing cellular energy utilization and storage. The activity of this bifunctional enzyme can act to switch a cell between carbohydrate oxidation (energy yielding) and carbohydrate synthesis (energy requiring). The phosphorylation state of PFK-2 dictates whether the enzyme will stimulate cellular carbohydrate breakdown or synthesis. (Kurland and Pilkis, Protein Science 4:1023–1037 (1995). The amino acid sequence containing the PFK-2 phosphorylation site is inserted into a specific site within the coding sequence for GFP that tolerates insertions (Baird et al., Proc. Natl. Acad. Sci., 96:11241–11246 (1999)), wherein the fluorescence properties of GFP are altered upon phosphorylation of PFK-2.

Nerve and muscle tissue interaction: Cellular components from the other model systems are combined to model tissue—tissue interactions. Neuronal NT2 cells are combined with C2C12 cells to allow their interaction during differentiation, much like tissues interact develop during normal development. Three scenarios are tested:

1. NT2 and C2C12 cells are arrayed together and allowed to differentiate together;
2. NT2 cells are arrayed on the substrate and differentiated, followed by addition and differentiation of C2C12 cells;
3. C2C 12 muscle stem cells are arrayed on the substrate and differentiated, followed by addition and differentiation of neuronal NT2 stems.

Other Examples

Neural crest stem cells can be treated with poly-D-lysine and fibronectin to produce peripheral neurons and glia, as disclosed in U.S. Pat. No. 6,033,906. The same stem cells when treated with fibronectin only produce glial cells but not neurons.

Mesenchymal stem cells treated with 100 nM dexamethasone +10 mM β-glycerophosphate are induced to undergo osteogenesis. (U.S. Pat. No. 5,942,225) The same stem cells treated with 5 ng/ml BMP are induced to undergo chondrogenesis; if treated with 5-azacytidine, they are induced to undergo myogenesis. Finally, the same stem cells treated with 10 u/ml IL-1α differentiate into stromal cells.

U.S. Pat. No. 5,827,740 teaches treating mesenchymal stem cells with glucocorticoids and phosphodiesterase inhibitor to induce adipogenesis.

EXAMPLE 6

Fluorescent Biosensor Toxin Characterization

As used herein, "toxin" refers to any organism, macromolecule, or organic or inorganic molecule or ion that alters normal physiological processes found within a cell, or any organism, macromolecule, or organic or inorganic molecule or ion that alters the physiological response to modulators of known physiological processes. Thus, a toxin can mimic a normal cell stimulus, or can alter a response to a normal cell stimulus.

Living cells are the targets of toxic agents that can comprise organisms, macromolecules, or organic or inorganic molecules. A cell-based approach to toxin detection, classification, and identification would exploit the sensitive and specific molecular detection and amplification system developed by cells to sense minute changes in their external milieu. By combining the evolved sensing capability of cells with the luminescent reporter molecules and assays described herein, intracellular molecular and chemical events caused by toxic agents can be converted into detectable spatial and temporal luminescent signals.

When a toxin interacts with a cell, whether it is at the cell surface or within a specific intracellular compartment, the toxin invariably undermines one or more components of the molecular pathways active within the cell. Because the cell is comprised of complex networks of interconnected molecular pathways, the effects of a toxin will likely be transmitted throughout many cellular pathways. Therefore, our strategy is to use molecular markers within key pathways likely to be affected by toxins, including but not limited to cell stress pathways, metabolic pathways, signaling pathways, and growth and division pathways.

We have developed and characterized three classes of cell based luminescent reporter molecules to serve as reporters of toxic threat agents. These 3 classes are as follows:
(1) Detectors: general cell stress detection of a toxin;
(2) Classifiers: perturbation of key molecular pathway(s) for detection and classification of a toxin; and
(3) Identifiers: activity mediated detection and identification of a toxin or a group of toxins.

Thus, in another aspect of the present invention, living cells are used as biosensors to interrogate the environment for the presence of toxic agents. In one embodiment of this aspect, an automated method for cell based toxin characterization is disclosed that comprises providing an array of locations containing cells to be treated with a test substance, wherein the cells possess at least a first luminescent reporter molecule comprising a detector and a second luminescent reporter molecule selected from the group consisting of a classifier or an identifier; contacting the cells with the test substance either before or after possession of the first and second luminescent reporter molecules by the cells; imaging or scanning multiple cells in each of the locations containing multiple cells to obtain luminescent signals from the detector; converting the luminescent signals from the detector into digital data to automatically measure changes in the localization, distribution, or activity of the detector on or in the cell, which indicates the presence of a toxin in the test substance; selectively imaging or scanning the locations containing cells that were contacted with test sample indicated to have a toxin in it to obtain luminescent signals from the second reporter molecule; converting the luminescent signals from the second luminescent reporter molecule into digital data to automatically measure changes in the localization, distribution, or activity of the classifier or identifier on or in the cell, wherein a change in the localization, distribution, structure or activity of the classifier identifies a cell pathway that is perturbed by the toxin present in the test substance, or wherein a change in the localization, distribution, structure or activity of the identifier identifies the specific toxin that is present in the test substance. In a preferred embodiment, the cells possess at least a detector, a classifier, and an identifier. In a further preferred embodiment, the digital data derived from the classifier is used to determine which identifier(s) to employ for identifying the specific toxin or group of toxins.

As used herein, the phrase "the cells possess one or more luminescent reporter molecules" means that the luminescent reporter molecule may be expressed as a luminescent reporter molecule by the cells, added to the cells as a luminescent reporter molecule, or luminescently labeled by contacting the cell with a luminescently labeled molecule that binds to the reporter molecule, such as a dye or antibody, that binds to the reporter molecule. The luminescent reporter molecule can be expressed or added to the cell either before or after treatment with the test substance.

The luminescent reporters comprising detectors, classifiers, and identifiers may also be distributed separately into single or multiple cell types. For example, one cell type may contain a toxin detector, which, when activated by toxic activity, implies to the user that the same toxin sample should be screened with reporters of the classifier or identifier type in yet another population of cells identical to or different from the cells containing the toxin detector.

The detector, classifier, and identifier can comprise the same reporter molecule, or they can comprise different reporters.

Screening for changes in the localization, distribution, structure or activity of the detectors, classifiers, and/or identifiers can be carried out in either a high throughput or a high content mode. In general, a high-content assay can be converted to a high-throughput assay if the spatial information rendered by the high-content assay can be recoded in such a way as to no longer require optical spatial resolution on the cellular or subcellular levels. For example, a high-content assay for microtubule reorganization can be carried out by optically resolving luminescently labeled cellular microtubules and measuring their morphology (e.g., bundled vs. non-bundled or normal). A high-throughput version of a microtubule reorganization assay would involve only a measurement of total microtubule polymer mass after cellular extraction with a detergent. That is, destabilized microtubules, being more easily extracted, would result in a lower total microtubule mass luminescence signal than unperturbed or drug-stabilized luminescently labeled microtubules in another treated cell population. The luminescent signal emanating from a domain containing one or more cells will therefore be proportional to the total microtubule mass remaining in the cells after toxin treatment and detergent extraction.

The methods for detecting, classifying, and identifying toxins can utilize the same screening methods described throughout the instant application, including but not limited to detecting changes in cytoplasm to nucleus translocation, nucleus or nucleolus to cytoplasm translocation, receptor internalization, mitochondrial membrane potential, signal intensity, the spectral response of the reporter molecule, phosphorylation, intracellular free ion concentration, cell size, cell shape, cytoskeleton organization, metabolic processes, cell motility, cell substrate attachment, cell cycle events, and organellar structure and function.

In all of these embodiments, the methods can be operated in both toxin-mimetic and toxin-inhibitory modes.

Such techniques to assess the presence of toxins are useful for methods including, but not limited to, monitoring the presence of environmental toxins in test samples and for toxins utilized in chemical and biological weapons; and for detecting the presence and characteristics of toxins during environmental remediation, drug discovery, clinical applications, and during the normal development and manufacturing process by virtually any type of industry, including but not limited to agriculture, food processing, automobile, electronic, textile, medical device, and petroleum industries.

We have developed and characterized examples of luminescent cell-based reporters, distributed across the 3 sensor classes. The methods disclosed herein can be utilized in conjunction with computer databases, and data management, mining, retrieval, and display methods to extract meaningful patterns from the enormous data set generated by each individual reporter or a combinatorial of reporters in response to toxic agents. Such databases and bioinformatics methods include, but are not limited to, those disclosed in U.S. patent application Ser. No. 09/437,976, filed Nov. 10, 1999; 60/145,770 filed Jul. 27, 1999 and U.S. patent application Ser. No. to be assigned, filed Feb. 19, 2000. (98,068-C).

Any cell type can be used to carry out this aspect of the invention, including prokaryotes such as bacteria and archaebacteria, and eukaryotes, such as single celled fungi (for example, yeast), molds (for example, Dictyostelium), and protozoa (for example, Euglena). Higher eukaryotes, including, but not limited to, avian, amphibian, insect, and mammalian cells can also be used.

TABLE 3

Examples of Biosensors

| # | Name | Class | Cell Types | Response to model toxins Positive | Negative |
|---|---|---|---|---|---|
| 1 | Mitochondrial Potential [Donnan Equilibrium Dye] | D | LLCPK (pig epithelia) Rat primary hepatocytes | Valinomycin (10 nM– 100 μM) FCCP (10 nM– 100 μM) | Oligomycin (10 nM) |
| 2 | Heat Shock Protein (Hsp 27, Hsp 70) GFP-chimera | D | HeLa 3T3 | Cadmium (10 mM) | TNF-α (100 ng/ml) |
| 3 | Tubulin-cytoskeleton [β-tubulin-GFP chimera] | C | BHK HeLa LLCPK | Paclitaxel (10 nM– 20 μM) Curacin-A (5 nM– 10 μM) Nocadazole (7 nM– 12 μM) Colchicine (5 nM– 10 μM) Vinblastine (5 nM– 10 μM) | Staurosporine (1 nM–1 μM) |
| 4 | pp38 MAPK-stress signaling [antibody and GFP-chimera] | C | 3T3 LLCPK | Anisomycin (100 μM) Cadmium (10 μM) | TNF-α (100 ng/ml) |
| 5 | NF-κB-stress signaling [antibody and GFP-chimera] | C | HeLa 3T3 BHK SNB19 HepG2 LLCPK | TNF-α (100 ng/ml– 0.38 pg/ml) IL-1 (4 ng/ml– .095 pg/ml) Nisin (2– 1000 μg/ml) Streptolysin (10 μg/ml) Anisomycin (100 μM) | Anisomycin (10 nM– 10 μM) Cadmium (1–10 μM) Penitrem A (10 μM) Valinomycin (1 μM) |
| 6 | IκB [complement to NF-κB] | C | In many cell types | | |
| 7 | Tetanus Toxin [Protease activity-based sensor] | I | In many cell types | | |
| 8 | Anthrax LF [Protease activity-based sensor] | I | In many cell types | | |

Sensor Class: D = Detector of toxins; C = Classifier of toxins; I = Identifier of toxin or group of toxins The model toxins can generally be purchased from Sigma Chemical Company (St. Louis, MO)

Examples of Detectors: This class of sensors provides a first line signal that indicates the presence of a toxic agent. This class of sensors provides detection of general cellular stress that requires resolution limited only to the domain over which the measurement is being made, and they are amenable to high content screens as well. Thus, either high throughput or high content screening modes may be used, including but not limited to translocation of heat shock factors from the cytoplasm to the nucleus, and changes in mitochondrial membrane potential, intracellular free ion concentration detection (for example, $Ca^{2+}$; H+), general metabolic status, cell cycle timing events, and organellar structure and function.

1. Mitochondrial Potential

A key to maintenance of cellular homeostasis is a constant ATP energy charge. The cycling of ATP and its metabolites ADP, AMP, inorganic phosphate, and solution-phase protons is continuously adjusted to meet the catabolic and anabolic needs of the cell. Mitochondria are primarily responsible for maintaining a constant energy charge throughout the entire cell. To produce ATP from its constituents, mitochondria must maintain a constant membrane potential within the organelle itself. Therefore, measurement of this electrical potential with specific luminescent probes provides a sensitive and rapid readout of cellular stress.

We have utilized a positively charged cyanine dye, JC-1 (Molecular Probes, Eugene, Oreg.), which diffuses into the cell and readily partitions into the mitochondrial membrane, for measurement of mitochondrial potential. The photophysics of JC-1 are such that when the probe partitions into the mitochondrial membrane and it experiences an electrical potential >140 mV, the probe aggregates and its spectral response is shifted to the red. At membrane potential values <140 mV, JC-1 is primarily monomeric and its spectral response is shifted toward the blue. Therefore, the ratio of two emission wavelengths (645 nm and 530 nm) of JC-1 partitioned into mitochondria provides a sensitive and continuous measure of mitochondrial membrane potential.

We have been making live cell measurements in a high throughput mode as the basis of a generalized indicator of toxic stress. The goal of our initial experiments was to determine the ratio of J-aggregates of JC-1 dye to its monomeric form both before and after toxic stress.

Procedure

1. Cells were plated and cultured up to overnight.
2. Cells were stained with JC-1 (10 μg/ml) for 30 minutes at 37° C. in a $CO_2$ incubator.
3. Cells were then washed quickly with HBSS at 37° C. (2 times, 150 μl/well), the toxins were added if required, and the entire plate was scanned in a plate reader. The JC-1 monomer was measured optimally with a 485 nm excitation/530 nm emission wavelength filter set, and the aggregates were best measured with a 590 nm excitation/645 nm emission wavelength set.

Results

The mitochondrial potential within several types of living cells, and the effects of toxins on the potential were measured using the fluorescence ratio Em 645 (590)/ Em 530 (485) (excitation wavelengths in parentheses). For example, we measured the effect of 10 μM valinomycin on the mitochondrial potential within LLCPK cells (pig epithelia). Within seconds of treatment, the toxin induced a more rapid and higher magnitude decrease (an approximately 50% reduction) in mitochondrial potential than that found in untreated cells. Hepatocytes were also determined to be sensitive to valinomycin, and the changes in mitochondrial potential were nearly complete within seconds to minutes after addition of various concentrations of the toxin.

These results are consistent with mitochondrial potential being a model intracellular detector of cell stress. Because these measurements require no spatial resolution within individual cells, mitochondrial potential measurements can be made rapidly on an entire cell array (e.g. high throughput). This means, for example, that complex arrays of many cell types can be probed simultaneously and continuously as a generalized toxic response. Such an indicator can provide a first line signal to indicate that a general toxic stress is present in a sample. Further assays can then be conducted to more specifically identify the toxin using cells classifier or identifier type reporter molecules.

2. Heat Shock Proteins

Most mammalian cells will respond to a variety of environmental stimuli with the induction of a family of proteins called stress proteins. Anoxia, amino acid analogues, sulfhydryl-reacting reagents, transition metal ions, decouplers of oxidative phosphorylation, viral infections, ethanol, antibiotics, ionophores, non-steroidal antiinflammatory drugs, thermal stress and metal chelators are all inducers of cell stress protein synthesis, function, or both. Upon induction, cell stress proteins play a role in folding and unfolding proteins, stabilizing proteins in abnormal configurations, and repairing DNA damage.

There is evidence that at least four heat shock proteins translocate from the cytoplasm to the nucleus upon stress activation of the cell. These proteins include the heat shock proteins HSP27 and HSP70, the heat shock cognate HSC70, and the heat shock transcription factor HSF1. Therefore, measurement of cytoplasm to nuclear translocation of these proteins (and other stress proteins that translocate from the cytoplasm to the nucleus upon a cell stress) will provide a rapid readout of cellular stress.

We have tested the response of an HSP27-GFP biosensor in two cell lines (BHK and HeLa) using a library of heavy metal chemical compounds as biological toxin stimulants to stress the cells. Briefly, cells expressing the HSP27-GFP biosensor are plated into 96-well microplates, and allowed to attach. The cells are then treated with a panel of cell stress-inducing compounds. Exclusively cytoplasmic localization of the fusion protein was found in unstimulated cells.

Other similar heat shock protein biosensors (HSP-70, HSC70, and HSF1 fused to GFP) can also be used as detectors.

Examples of Classifiers:

This class of sensors detects the presence of, and further classifies toxins by identifying the cellular pathway(s) perturbed by the toxin. As such, this suite of sensors can detect and/or classify toxins into broad categories, including but not limited to "toxins affecting signal transduction," "toxins affecting the cytoskeleton," and "toxins affecting protein synthesis". Either high throughput or high content screening modes may be used. Classifiers can comprise compounds including but not limited to tubulin, microtubule-associated proteins, actin, actin-binding proteins including but not limited to vinculin, α-actinin, actin depolymerizing factor/cofilin, profilin, and myosin; NF-κB, IκB, GTP-binding proteins including but not limited to rac, rho, and cdc42, and stress-activated protein kinases including but not limited to p38 mitogen-activated protein kinase.

1. Tubulin-Cytoskeleton

The cell cytoskeleton plays a major role in cellular functions and processes, such as endo- and exocytosis, vesicle transport, and mitosis. Cytoskeleton-affecting toxins, of proteinaceous and non-proteinaceous form, such as C2 toxin, and several classes of enterotoxins, act either directly on the cytoskeleton, or indirectly via regulatory components controlling the organization of the cytoskeleton. Therefore, measurement of structural changes in the cytoskeleton can provide classification of the toxin into a class of cytoskeleton-affecting toxins. This assay can be conducted in a high content mode, as described previously, or in a high throughput mode. For high throughput as discussed previously.

Such measurements will be valuable for identification of toxins including, but not limited to anti-microtubule agents, agents that generally affect cell cycle progression and cell proliferation, intracellular signal transduction, and metabolic processes.

For microtubule disruption assays, LLCPK cells stably transfected with a tubulin-GFP biosensor plasmid were plated on 96 well cell culture dishes at 50–60% confluence and cultured overnight at 37° C., 5% $CO_2$. A series of concentrations (10–500 nM) of 5 compounds (paclitaxel, curacin A, nocodazole, vinblastine, and colchicine) in normal culture media were freshly prepared from stock, and were added to cell culture dishes to replace the old culture media. The cells were then observed with the cell screening system described above, at a 12 hour time point.

Our data indicate that the tubulin chimera localizes to and assembles into microtubules throughout the cell. The microtubule arrays in cells expressing the chimera respond as follows to a variety of anti-microtubule compounds:

| Drug | Response |
|---|---|
| Vinblastine | Destabilization |
| Nocodazole | Destabilization |
| Paclitaxel | Stabilization |
| Colchicine | Destabilization |
| Curacin A | Destabilization |

Similar data were obtained using cells expressing the tubulin biosensor that were patterned onto cell arrays (such as those described in U.S. patent application Ser. No. 08/865,341 filed May 29, 1997, incorporated by reference herein in its entirety) and dosed as above.

2. NF-κB

NF-κB is cytoplasmic at basal levels of stimulation, but upon insult translocates to the nucleus where it binds specific DNA response elements and activates transcription of a number of genes. Translocation occurs when IkB is degraded by the proteosome in response to specific phosphorylation and ubiquitination events. IkB normally retains NF-κB in the cytoplasm via direct interaction with the protein, and masking of the NLS sequence of NF-κB. Therefore, although not the initial or defining event of the whole signal cascade, NF-κB translocation to the nucleus can serve as an indicator of cell stress.

NF-κB Immunolocalization

For further studies, we characterized endogenous NF-κB activation by immunolocalization in toxin treated cells. The NF-κB antibodies used in this study were purchased from Santa Cruz Biotechnology, Inc. (Santa Cruz, Calif.), and secondary antibodies are from Molecular Probes (Eugene, Oreg.).

For the 3T3 and SNB19 cell types, we determined the effective concentrations that yield response levels of 50% of the maximum (EC50), expressed in units of mass per volume (ng/ml) and units of molarity. Based on molecular weights of 17 kD for both TNFα and IL-1α, the EC50 levels for these two compounds with 3T3 and SNB19 cell types are given in units of molarity in Table 3. Our results demonstrated reproducibility of the relative responses from zero to maximum dose, but from sample to sample there have been occasional shifts in the baseline intensities of the response at zero concentration.

For these experiments, either 10 or 100 TNFα-treated 3T3 or SNB19 cells/well were tested. On the basis of the standard deviations measured for these samples, and by taking t-values for the student's t-test, we have estimated the minimum detectable doses for each case of cell type, compound, number of cells per well, and for different choices of how many wells are sampled per condition. The latter factor determines the number of degrees of freedom that are provided in the sample of data. Increasing the number of wells from 4 to 16, and increasing the number of cells per well from 10 to 100, improves the minimum detectable doses considerably. For 3T3 cells, which show lower minimum detectable doses than the SNB19 cells, and for the case of 1% false negative and 1% false positive rates, we estimate that 100 cells per well and a sampling of 12 or 16 wells are sufficient to detect a dose approximately equal to the EC50 value of 0.15 ng/ml. If the false positive rate is relaxed to 20%, a concentration of approximately half that value can be detected (0.83 ng/ml). One hundred cells can conveniently be sampled over a cell culture surface area of less than 1 mm².

TABLE 3

EC50 levels for TNFα and IL-1α (based on molecular weights of 17 kD for both)

| Compound | Cell Type | EC50 ($10^{-12}$ moles/liter) |
|---|---|---|
| TNFα | 3T3 | 8.8 |
| | SNB19 | 5.9 |
| IL-1α | 3T3 | 0.24 |
| | SNB19 | 59 |

3. Phospho-p38 Mitogen Activated Protein Kinase (pp38MAPK)

MAPKs play a role in not only cell growth and division, but as mediators of cellular stress responses. One MAPK, p38, is activated by chemical stress inducers such as hyperosmolar sorbitol, hydrogen peroxide, arsenite, cadmium ions, anisomycin, sodium salicylate, and LPS. Activation of p38 is also accompanied by its translocation into the nucleus from the cytoplasm.

MAPK p38 lies in a pathway that is a cascade of kinases. Thus, p38 is a substrate of one or more kinases, and it acts to phosphorylate one or more substrates in time and space within the living cell.

The assay we present here measures, as one of its parameters, p38 activation using immunolocalization of the phosphorylated form of p38 in toxin-treated cells. The assay was developed to be flexible enough to include the simultaneous measurement of other parameters within the same individual cells. Because the signal transduction pathway mediated by the transcription factor NF-κB is also known to be involved in the cell stress response, we included the activation of NF-κB as a second parameter in the same assay.

Figure 46:
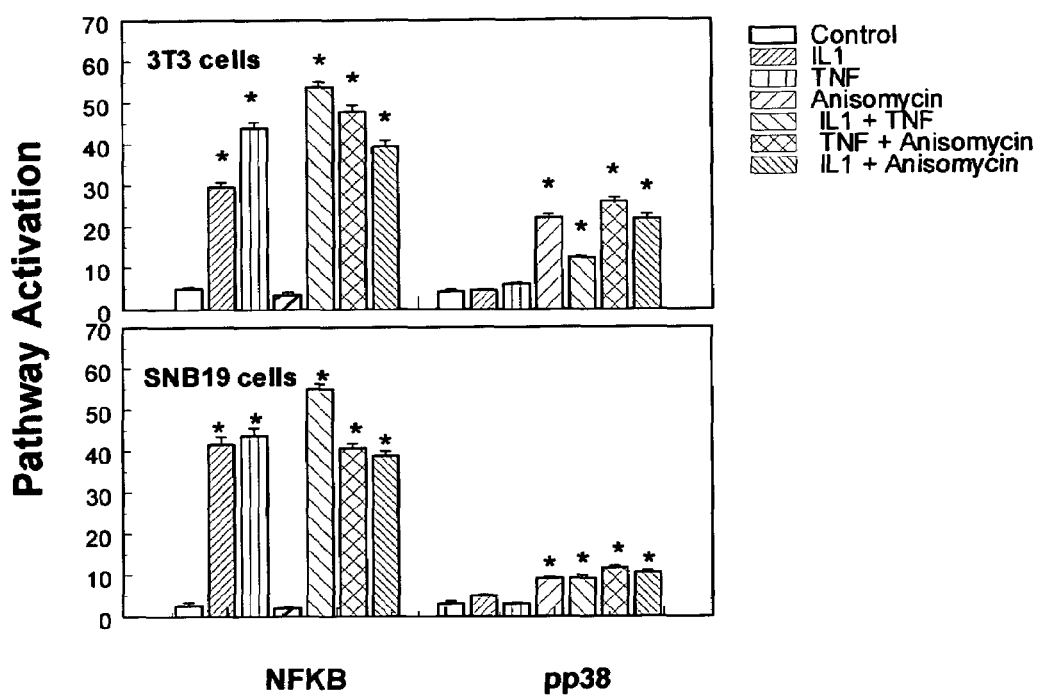
FIG. 46 shows the differential response in a dual labeling assay of the p38 MAPK and NF-κB pathways across three model toxins and two different cell types. Treatments marked with an asterisk are different from controls at a 99% confidence level (p<0.01).

Our experiments demonstrate an immunofluorescence approach can be used to measure p38 MAPK activation either alone or in combination with NF-κB activation in the same cells. Multiple cell types, model toxins, and antibodies were tested, and significant stimulation of both pathways was measured in a high-content mode. The phospho-p38 antibodies used in this study were purchased from Sigma Chemical Company (St. Louis, Mo.). We report that at least two cell stress signaling pathways can not only be measured simultaneously, but are differentially responsive to classes of model toxins. FIG. 46 shows the differential response of the p38 MAPK and NF-κB pathways across three model toxins and two different cell types. Note that when added alone, three of the model toxins (IL1α, TNFα and Anisomycin) can be differentiated by the two assays as activators of specific pathways.

IκB chimera

IkB degradation is the key event leading to nuclear translocation of NF-κB and activation of the NFkB-mediated stress response. We have chosen this sensor to complement the NF-κB sensor as a classifier in a high-throughput mode: the measurement of loss of signal due to degradation of the IκB-GFP fusion protein requires no spatial resolution within individual cells, and as such we envision IkB degradation measurements being made rapidly on an entire cell substrate.

This biosensor is based on fusion of the first 60 amino acids of IkB to the Fred25 variant of GFP. This region of IkB contains all the regulatory sequences, including phosphorylation sites and ubiquitination sites, necessary to confer proteosome degradation upon the biosensor. Knowing this, stimulation of any pathway that would typically lead to NFkB translocation results in degradation of this biosensor. Monitoring the fluorescence intensity of cells expressing IkB-GFP identifies the degradation process.

Examples of Identifiers:

In our toxin identification strategy, the first two levels of characterization ensure a rapid readout of toxin class without sacrificing the ability to detect many new mutant toxins or dissect several complex mixtures of known toxins. The third level of biosensors are identifiers, which can identify a specific toxin or group of toxins. In one embodiment, an identifier comprises a protease biosensor that responds to the activity of a specific toxin. Other identifiers are produced with reporters/biosensors specific to their activities. These include, but are not limited to post-translational modifications such as phosphorylation or ADP-ribosylation, translocation between cellular organelles or compartments, effects on specific organelles or cellular components (for example, membrane permeabilization, cytoskeleton rearrangement, etc.)

ADP-ribosylating toxins—These toxins include *Pseudomonas* toxin A, diptheria toxin, botulinum toxin, pertussis toxin, and cholera toxin. For example, *C. botulinum* C2 toxin induces the ADP-ribosylation of Arg177 in the cytoskeletal protein actin, thus altering its assembly properties. Besides the construction of a classifier assay to measure actin-cytoskeleton regulation, an identifier assay can be constructed to detect the specific actin ADP-ribosylation. Because the ADP-ribosylation induces a conformational change that no longer permits the modified actin to polymerize, this conformational change can be detected intracellularly in several possible ways using luminescent reagents. For example, actin can be luminescently labeled using a fluorescent reagent with an appropriate excited state lifetime that allows for the measurement of the rotational diffusion of the intracellular actin using steady state fluorescence anisotropy. That is, toxin-modified actin will no longer be able to assemble into rigid filaments and will therefore produce only luminescent signals with relatively low anisotropy, which can be readily measured with an imaging system. In another embodiment, actin can be labeled with a polarity-sensitive fluorescent reagent that reports changes in actin-conformation through spectral shifts of the attached reagent. That is, toxin-treatment will induce a conformational change in intracellular actin such that a ratio of two fluorescence wavelengths will provide a measure of actin ADP-ribosylation.

Cytotoxic phospholipases—Several gram-positive bacterial species produce cytotoxic phospholipases. For example, *Clostridium perfringens* produces a phospholipase C specific for the cleavage of phosphoinositides. These phosphoinositides (e.g., inositol 1,4,5-trisphosphate) induce the release of calcium ions from intracellular organelles. An assay that can be conducted as either high-content or high-throughput can be constructed to measure the release of calcium ions using fluorescent reagents that have altered spectral properties when complexed with the metal ion. Therefore, a direct consequence of the action of a phospholipase C based toxin can be measured as a change in cellular calcium ion concentration.

Exfoliative toxins—These toxins are produced by several Staphylococcal species and can consist of several serotypes. A specific identifier for these toxins can be constructed by measuring the morphological changes in their target organelle, the desmosome, which occur at the junctions between cells. The exfoliative toxins are known to change the morphology of the desmosomes into two smaller components called hemidesmosomes. In the high-content assay for exfoliative toxins, epithelial cells whose desmosomes are luminescently labeled are subjected to image analysis. An method that detects the morphological change between desmosomes and hemidesmosomes is used to quantify the activity of the toxins on the cells.

Most of these identifiers can be used in high throughput assays requiring no spatial resolution, as well as in high content assays.

Several biological threat agents act as specific proteases, and thus we have focused on the development of fluorescent protein biosensors that report the proteolytic cleavage of specific amino acid sequences found within the target proteins.

A number of such protease biosensors (including FRET biosensors) are disclosed above, such as the caspase biosensors, anthrax, tetanus, Botulinum, and the zinc metalloproteases. FRET is a powerful technique in that small changes in protein conformation, many of which are associated with toxin activity, can not only be measured with high precision in time and space within living cells, but can be measured in a high-throughput mode, as discussed above.

As described above, one of skill in the art will recognize that the protease biosensors of this aspect of the invention can be adapted to report the activity of any protease, by a substitution of the appropriate protease recognition site. These biosensors can be used in high-content or high throughput screens to detect in vivo activation of enzymatic activity by toxins, and to identify specific activity based on cleavage of a known recognition motif. These biosensors can be used in both live cell and fixed end-point assays, and can be combined with additional measurements to provide a multi-parameter assay.

Anthrax LF

Anthrax is a well-known agent of biological warfare and is an excellent target for development of a biosensor in the identifier class. Lethal factor (LF) is one of the protein components that confer toxicity to anthrax, and recently two of its targets within cells were identified. LF is a metalloprotease that specifically cleaves Mek1 and Mek2 proteins, kinases that are part of the MAP-kinase signaling pathway. Green fluorescent protein (GFP) is fused in-frame at the amino terminus of either Mek1 or Mek2 (or both), resulting in a chimeric protein that is retained in the cytoplasm due to the presence of a nuclear export sequence (NES) present in both of the target molecules. Upon cleavage by active lethal factor, GFP is released from the chimera and is free to diffuse into the nucleus. Therefore, measuring the accumulation of GFP in the nucleus provides a direct measure of LF activity on its natural target, the living cell.

Multi-Parametric Screens

Multiparameter high-content assays for toxin activity within a single population of cells has several advantages over single parameter assays:

1. The reagent and cell-handling overhead is greatly reduced over multiple single parameter assays.
2. The time requirements for sample preparation and analysis are greatly reduced.
3. Reagents can be conserved.
4. Most importantly, the biological analysis and the building of cellular knowledge can be greatly enhanced when multiple toxin activity parameters are measured within single cells.

Presented here is an analysis of multiple physiological targets within multiple single cell types. The results are consistent with toxin identification and characterization. The specific toxins chosen for the demonstration were *Staphylococcus* Enterotoxin B, (SEB), tumor necrosis factor alpha (TNFα), and botulinum toxin.

To complete the analysis, the following strategy was pursued:

1. Choose intracellular targets known to be modulated by SEB and botulinum toxins and substitute analogs that can be used to verify the assay. SEB is known to activate p38 MAPK in some cell types. The botulinum toxin C3 exoenzyme is known to affect the organization of the actin-cytoskeleton through its ADP-ribosylation activity. One well-characterized effect of TNFα is the stimulation of NF-κB transcriptional activity. Furthermore, it is also known that there is cross talk between the pathways activated by all three of the above toxins. Therefore, a combinatorial approach was used to measure the activation of cytoskeletal, MAPK, and NF-κB pathways within the same single cells.
2. Choose toxin analogs known to stimulate the above pathways. To simulate the activity of the above toxins, the following compounds and ions were proposed for use as toxin analogs:
   i) Anisomycin [SEB analog]—This drug is known to activate the p38 MAPK pathway through increased phosphorylation of p38. Measurement is done using antibodies against the phosphorylated (activated) form of p38 and the cytoplasm to nuclear translocation application.
   ii) TNFα [TNFα]—This cytokine is known to activate the NF-κB pathway and is measurable as the cytoplasm to nuclear translocation of the transcription factor.
   iii) Latrunculin [botulinum C3 exoenzyme analog]—This drug is known to affect the equilibrium between globular and filamentous actin in living cells. This shift in equilibrium is measurable as a change in the intensity of fluorescent phalloidin labeling of single cells.

Cell plating and drug treatment. Swiss 3T3 cells were plated at 15,000 cells per well in a 96-well microplate 8 hours before drug treatment. Columns consisting of 8 wells within the plate were treated with the following concentration ranges of drugs: TNFα, 0.781–10 ng/ml; anisomycin, 7.81–1000 nM; and latrunculin, 2.5–320 nM. The cells were treated with the drugs for 30 minutes at 37° C. in a humidified 5% $CO_2$ atmosphere.

Cell labeling. After drug incubation, the medium was removed from the wells and replaced with a solution (175 µl/well) containing 4% formaldehyde and 10 µg/ml Hoechst 33342 in Hank's Balanced Salt Solution (HBSS). The cells were incubated in this solution for 20 minutes at room temperature. The wells were rinsed once with HBSS (200 µl/well), and then treated for 5 minutes at room temperature with a solution (200 µL/well) containing 0.5% (v/v) Triton X-100 in HBSS. After this detergent extraction, the cells were rinsed as above and incubated with a solution (50 µl/well) containing a 1:500 dilution of a mouse monoclonal antibody to phosphorylated p38 MAPK, a 1:200 dilution of a rabbit polyclonal antibody to NF-κB, and a 1:400 dilution of Alexa 488 labeled phalloidin for 1 hour at room temperature. After rinsing as above, the cells were incubated one last time with a solution (50 µl/well) containing a 1:150 dilution of Alexa 568-labeled polyclonal anti-mouse antibody solution and a 1:150 dilution of a Cy5-labeled polyclonal anti-rabbit antibody solution for 1 hour at room temperature. The cells were rinsed as above, and stored at 4° C. in a sealed plate containing HBSS (200 µl/well).

High-content analysis of labeled cells. The 96-well microplate containing the multiply labeled cells was scanned with a cell screening system, including but not limited to those disclosed in U.S. Pat. No. 5,989,835 and in U.S. patent application Ser. No. 09/031,271 filed Feb. 27, 1998, both incorporated by reference herein in their entirety. Cytoplasm to nuclear ratios were made for p38 MAPK, NF-κB, and actin within the same population of cells.

Results and Discussion

Table 4 shows the results of the multiparameter measurement of three intracellular activities as a function of the concentration of three different toxins. NF-κB translocation is shown to be sensitive to TNFα concentration, but p38 MAPK and actin-cytoskeleton assembly state in the same cells are relatively insensitive. p38 MAPK activation is more sensitive than NF-κB translocation to increasing anisomycin concentration. Here again, actin-cytoskeletal assembly state is relatively unaffected by this drug. High concentrations of latrunculin induce a reorganization of the actin-cytoskeleton, but have relatively little effect on p38 MAPK activation or NF-κB translocation in the same cells.

TABLE 4

| | Maximal Cellular Response Relative to Control* | | |
|---|---|---|---|
| Analog | NF-κB | p38 MAPK | Actin |
| TNFα | 1.8 (>25 nM) | 1.2 (>200 nM) | 1.0 |
| Anisomycin | 1.0 | 1.4 (>200 nM) | 1.0 |
| Latrunculin | 1.0 | 1.0 | 1.2 (>150 nM) |

*A maximal cellular response of 1.0 indicates no significant difference over control values.

The analysis of cellular data using multiparameter high-content assays demonstrated here provides new insights into the mechanisms of both known and unknown toxin activity. For example, TNFα acts as a toxin through a molecular pathway that uses NF-κB translocation to activate specific cellular genes, while anisomycin action is consistent with the activation of both p38 MAPK and NF-κB pathways. The further application of this multiparameter approach where comparisons are made at the single cell level also greatly increases the resolution to which toxin action can be dissected and therefore improves the precision and sensitivity of toxin detection.

EXAMPLE 12

Matrix for Toxin Detection and Organ Localization

In another aspect, the present invention provides a cassette for cell screening, comprising a substrate having a surface; and a fluid delivery system mated with the substrate, wherein the fluid delivery system comprises (1) a matrix of openings or depressions, wherein each region of the substrate enclosed by the opening or depression in the matrix comprises an individually addressable domain; and (2) microfluidic channels that supply fluid to the domains. The architecture of the fluidic channels is governed by the laws of fluid flow in microchannels alone.

In this aspect, the microfluidic device consists of a matrix of either openings or depressions with dimensions ranging from 1 µm to 10,000 µm per side, or 1 µm to 10,000 µm in diameter with depths ranging from 10 µm to 10,000 µm. Such a matrix can comprise any desired number of rows and columns.

In one embodiment, a 3×3 matrix comprises openings, which when bonded to the substrate permits modification of the substrate surface with adhesion chemistry and cells. Subsequently, the openings are closed, and the closed cassette is used for screening by pumping fluids and reagents into the assay domains via the microfluidic channels. The microfluidic device can be bonded to the substrate via such non-limiting means as anodic bonding, electrofusion, thermal bonding, adhesive bonding, and pressure bonding. Each region on the substrate enclosed by an opening or depression now constitutes a "domain" on the substrate.

In another embodiment of this aspect of the invention, the substrate comprises cell binding locations separated by cell repulsive regions, and cells are arrayed on the cell binding locations. In a preferred embodiment, each domain on the substrate comprises a single cell type. The nine domains on the substrate are thus preferably arrayed with between one and nine different cell types, with each cell type bearing one or more biosensors reporting on one or more intracellular pathways. In further preferred embodiments, at least three different cell types are arrayed on the substrate; and the different cell types arrayed on the substrate are specific for different tissue types, including but not limited to cells specific for connective tissue, neuronal tissue, and the immune system.

As such, each of the nine domains has a single cell type arrayed on cell binding locations. Each of the nine domains are individually addressable by a fluid of choice using the microfluidic device. If the fluid delivery device comprises a matrix of openings, the top of the device is sealed from the environment with a glass or plastic film, or an air permeable and water impermeable membrane such as BREATH-EASY™ (Sigma Chemical Co.), by means such as, but not limited to anodic bonding, anodic bonding, electrofusion, thermal bonding, adhesive bonding, and pressure bonding. The semi-permeable membrane enables oxygen and carbon dioxide diffusion for long-term viability and functionality of the cells.

Cell adhesion promoters and inhibitors that can be used include, but are not limited to, those discussed throughout the application. In a most preferred embodiment, the cell adhesion promoter comprises a silane, and the cell repulsive moiety comprises tresyl-activated PEG. The surface modifications can be achieved by either transferring cell adhesive molecules onto the substrate in select regions, or by coating select regions of the substrate with cell repulsive molecules via any method, including but not limited to those described above. The substrate so modified is arrayed with cells in each of the regions enclosed by the square openings or depressions. Alternatively, the substrate can be modified with cell adhesive and cell selective chemistries after bonding to the microfluidic device. Where the fluid delivery system comprises a matrix of openings, the chemistries and cells can be arrayed on the substrate either via the microfluidic channels, or via the openings in the fluid delivery system, after which the wells are closed with a glass film, plastic film, or air permeable and water impermeable membrane as described above. Where the fluid delivery system comprises a matrix of depressions, the chemistries and cells can be delivered via the microfluidic channels.

In another aspect, the invention provides a method for cell screening, comprising providing the cassette for cell screening described in this example, providing an optical system to obtain images of the cells; contacting the domains with a test compound; and obtaining images of the cells to determine an effect of the test compound on the cells. Such screening can be conducted in either a high content mode, a high throughput mode or a combination of the two. The high throughput mode permits optical detection of signals arising from all domains on the substrate in one pass, while the high content mode permits sub-cellular resolution and detection of signals arising from each individual cell within each domain.

In a preferred embodiment, the method detects the pathway and organ localization of a toxin, wherein the substrate comprises multiple cell types each with one or more biosensors that are affected by a toxin; contacting the domains with a test sample potentially comprising a toxin, and obtaining images of the cells to determine an effect of the toxin on the different cell types, wherein an effect of the toxin on the cell types indicates the toxin pathway and organ localization. As used herein, "organ localization" means that a particular toxin has an effect on cells from a particular organ, and thus its toxicity may be mediated, at least in part, through that organ. The term does not imply that cells from other organs are not affected by the toxin.

In a further preferred embodiment, the biosensors expressed by the cells are selected from the group consisting of detectors, classifiers, and identifiers, as described above.

In a further aspect, the invention further provides an automated method for cell based toxin detection and organ localization comprising providing an array of locations containing cells to be treated with a test substance, wherein the array comprises at least a first cell type and a second cell type, and wherein the first cell type and the second cell type are not contained on the same location in the array; wherein the first and second cell types are derived from different organ types; wherein each of the cell types comprises at least one luminescent reporter molecule; wherein the localization, distribution, structure, or activity of the at least one luminescent reporter molecule is altered by a toxin to be detected;

contacting the at least first cell type and second cell type with the test substance either before or after possession of the at least one luminescent reporter molecules by the first cell type and the second cell type;

imaging or scanning multiple cells in each of the locations containing the first cell type or the second cell type to obtain luminescent signals from the luminescent reporter molecule in the first cell type and the second cell type;

converting the luminescent signals into digital data;

utilizing the digital data to automatically measure the localization, distribution, structure or activity of the at least one luminescent reporter molecule on or in the first cell type and the second cell type, wherein a change in the localization, distribution, structure or activity of the luminescent reporter molecule indicates the presence of a toxin and an organ localization of the toxin.

In a preferred embodiment, the array further comprise a third cell type, wherein the first, second, and third cell types are not contained on the same location in the array; and wherein the first, second, and third cell types are derived from different organ types.

In a further preferred embodiment, the cell types further comprise at least a second luminescent reporter molecule; wherein the localization, distribution, structure, or activity of the second luminescent reporter molecule is altered by a toxin to be detected.

For developing a 3×3 matrix of assays and toxin analogs for multi-parametric toxin identification and organ localization, several factors were considered, including the cellular events or pathways that are affected by toxic agents, the critical biochemical targets that undergo a measurable change in response to a toxin, and whether such changes in the critical biochemical target are measurable. The following are representative examples of such assays, toxins, and toxin analogs that can be used in accordance with the present invention. One of skill in the art will recognize that many other such assays, toxins, and toxin analogs can be used according to the teachings of the present invention, all of which are encompassed by the present invention.

The shape of a cell is determined in large part by its actin cytoskeleton. Upon loss of F-actin, cells undergo profound shape changes. Botulinum C3 toxin is a member of a class of toxins that target the Ras signaling pathway. Botulinum C3 toxin inactivates Rho, leading to actin depolymerization, thus causing a detectable change in cell morphology, particularly a decrease in cell area. Similarly to Botulinum C3, cytochalasin D binds to actin and prevents polymerization, leading to loss of cytoskeletal organization. Thus, cytochalasin D can be used as a Botulinum C3 analog to demonstrate the ability of the toxin assay to classify a toxin present in the sample as affecting cell morphology in a manner similar to Botulinum C3. F-actin can be labeled with fluorescent phalloidin to reveal the cytoskeletal structure, and changes in such structure can be measured in response to a test sample containing cytochalasin D. Thus, the present assay serves to classify the toxin as one that perturbs the cell's actin filament structure.

Botulinum C3 also induces the expression of cell stress proteins, and thus would be detected as a toxin by a cell stress protein biosensor, such as those described above. Botulinum C3 also affects membrane trafficking.

The p38 MAP kinase, (pp38MAPK, discussed above), is phosphorylated and translocates to the nucleus upon activation of the MAP kinase pathway. Antibodies specific for phosphorylated p38 (the target of pp38MAPK) report its location in the cell. pp38MAPK is also a target of Staphylococcal enterotoxin B (SEB) and T2 Toxin. SEB alters the function of immune cells and stimulates p38 activation and translocation in some T-cell lines. Certain tricothecene mycotoxins (e.g. T2 toxins such as T2 triol) inhibit protein synthesis and induce p38 activity. Anisomycin also inhibits protein synthesis and induces p38 translocation to the nucleus as discussed above, and thus can be used as an analog of SEB and T2 toxin, to demonstrate the ability of the toxin assay to classify a toxin present in the sample as affecting p38 activation and/or localization in a manner similar to SEB and/or T2 toxins. Furthermore, by utilizing cells specific for the immune system, the assay provides information on toxin localization in the body.

SEB also induces the expression of cell stress proteins, and thus could be detected in a test sample as a toxin by a cell stress protein biosensor, such as those described above. SEB also affects microtubule structure, and its presence in a test sample would lead to a classification of the test sample as containing a toxin that perturbs the cell microtubule structure.

Cells respond to environmental agents of stress (as discussed above) through specific signaling cascades. As discussed above, NFkB is a transcription factor that activates production of proteins as part of the cellular defense response to general cell stress. NFKB resides in the cytoplasm but translocates to the nucleus upon release from a complex with IκB. Antibody staining reveals the subcellular localization of NFkB. TNF-a is a strong inducer of NF-κB translocation to the nucleus, and thus can be used as an analog of toxins that induce cell stress, including but not limited to cholera toxin.

TABLE 5

Matrix 1: Dissection of pathway and organ localization of 1 toxin per cassette

| | Toxin 1 1 | Toxin 1 2 | Toxin 1 3 |
|---|---|---|---|
| A | SD3T3 (HSP) | SD3T3 (NF-kB) | SD3T3 (β-tubulin) |
| B | SNB19 (HSP) | SNB19 (NF-kB) | SNB19 (β-tubulin) |
| C | RAW (HSP) | RAW (NF-kB) | RAW (β-tubulin) |

This example permits addressing the effect of a single toxin on connective tissue, neuronal tissue, and immune specific cells as measured through cell stress, transcription factor activation, and cytoskeleton reorganization. Each cassette has a 3×3 matrix of square openings, and a total of nine domains. Three different cell types are each arrayed in three of the domains, with the cells in a single domain expressing a single toxin biosensor. Each cell type expresses a different toxin bio sensor in each of the domains in which it is arrayed.

Cell Types:
(A) SD3T3: connective tissue cell type: Serum-deprived 3T3 fibroblast (ATCC CCL-92)
(B) SNB19: neuronal tissue cell type: Human glioblastoma (ATCC#CRL-2219)
(C) RAW: Immune specific cell type: Murine macrophage cell line (ATCC#TIB-71)

Column 1 (A1/B1/C1) will provide a "low resolution" image of the sample. If the sample contains the minimum detectable concentration of either SEB, Cholera Tox, or Bot. Tox, it will elicit a positive cell stress response from each of the 3 tissue specific cells. A positive response in Column 1 would entail a "higher resolution" probe of the sample in Columns 2 and 3. The modality of action and tissue specificity of the toxin are dissected in Columns 2 and 3, using the NF-κB and β-tubulin biosensors.

TABLE 6

Matrix 2: Dissection of pathway and organ localization of 1 toxin per cassette plus an internal control

| | Toxin 1 1 | Toxin 1 2 | PBS 3 |
|---|---|---|---|
| A | SD3T3 (HSP) | SD3T3 (NF-kB + β-tubulin) | SD3T3 (NF-kB + β-tubulin) |
| B | SNB19 (HSP) | SNB19 (NF-kB + β-tubulin) | SNB19 (NF-kB + β-tubulin) |
| C | RAW (HSP) | RAW (NF-kB + β-tubulin) | RAW (NF-kB + β-tubulin) |

Each cassette with a 3×3 array of the 3 cell types with each of the 3 toxin biosensors enables addressing the effect of a single toxin on connective tissue, neuronal tissue, and immune specific cells as measured through cell stress, transcription factor activation, and cytoskeleton reorganization. Columns 2 and 3 have cells expressing 2 fluorescent protein biosensors each. This enables simultaneous detection of 2 different sets of macromolecules representing two different pathways within the same cells.

TABLE 7

Matrix 3: Dissection of pathway and organ localization of 3 toxins per cassette

| | Toxin 1 1 | Toxin 2 2 | Toxin 3 3 |
|---|---|---|---|
| A | SD3T3 (HSP + NF-kB + β-tubulin) | SD3T3 (HSP + NF-kB + β-tubulin) | SD3T3 (HSP + NF-kB + β-tubulin) |
| B | SNB19 (HSP + NF-kB + β-tubulin) | SNB19 (HSP + NF-kB + β-tubulin) | SNB19 (HSP + NF-kB + β-tubulin) |
| C | RAW (HSP + NF-kB + β-tubulin) | RAW (HSP + NF-kB + β-tubulin) | RAW (HSP + NF-kB + β-tubulin) |

Each cell on the substrate has the capacity to simultaneously report the effect of a toxin on cell stress, transcription factor activation and translocation, and reorganization of the cytoskeletal proteins.

Experimental Design and Results of 3×3 Matrix Model System

The following matrix of toxins, analogs, and assays were used for 3×3 matrix study based on the above examples, except that the Swiss 3T3 cells were exposed to the toxin analogs for 45 minutes. In each assay, the analogs were used at the following concentrations:

| Medium exchange | negative control |
|---|---|
| TNF α | 1.8 nM |
| Anisomycin | 30 μM |
| Cytochalasin D | 2 μM |

Cell Stress Target

Figure 47:
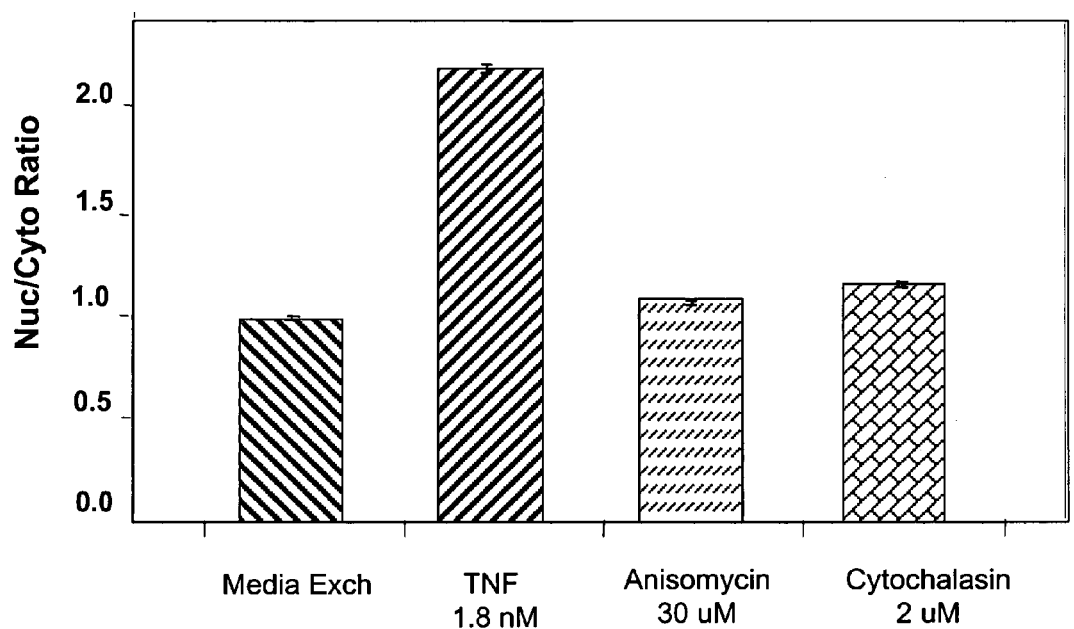
FIG. 47 is a bar graph showing quantitative results for the proportion of NFKB protein in the nucleus versus the cytoplasm for wells treated by medium exchange (negative control), TNF α (1.8 nM), Anisomycin (30 μM), and Cytochalasin D (2 μM) after exposure of Swiss 3T3 cells for 45 minutes. The dominant response is obtained for TNF α. Mean+/−SEM n=1500 cells totaled across 16 wells.

Quantitative results were determined based on data obtained from 1500 cells totaled across 16 wells. The proportion of NF-kB protein in the nucleus versus the cytoplasm for wells treated by the toxin analogs is shown in FIG. 47. The dominant response was obtained for TNF α.

SEB/T2 Target

Figure 48:
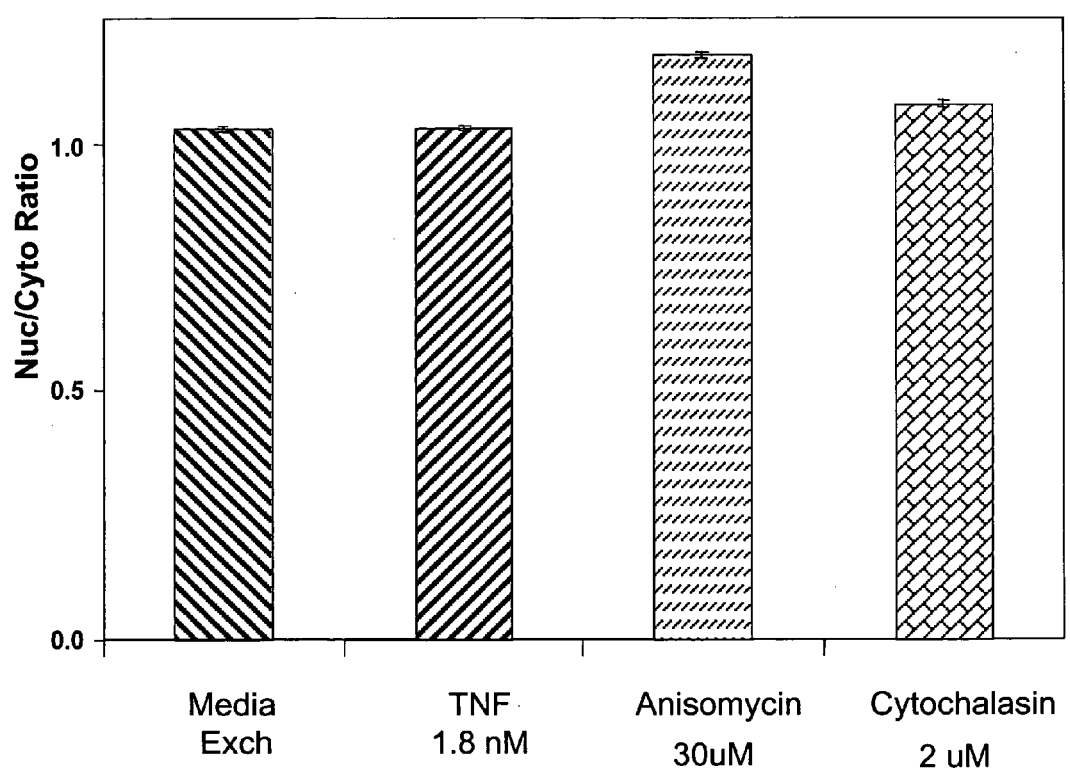
FIG. 48 is a bar graph showing quantitative results for the proportion of phosphorylated p38 MAPK in the nucleus versus the cytoplasm for wells treated by medium exchange (negative control), TNF α (1.8 nM), Anisomycin (30 μM), and Cytochalasin D (2 μM) after exposure of Swiss 3T3 cells for 45 minutes. The dominant response is obtained for Anisomycin. Mean+/−SEM n=1500 cells totaled across 16 wells.

Quantitative results were determined based on data obtained from 1500 cells totaled across 16 wells. Phosphorylated p38 MAPK in the nucleus versus the cytoplasm for wells treated by the toxin analogs was as shown in FIG. 48. The dominant response was obtained for anisomycin.

Botulinum C2 Target

Quantitative results were obtained based on results from 500 cells totaled across 6 wells.

Figure 49:
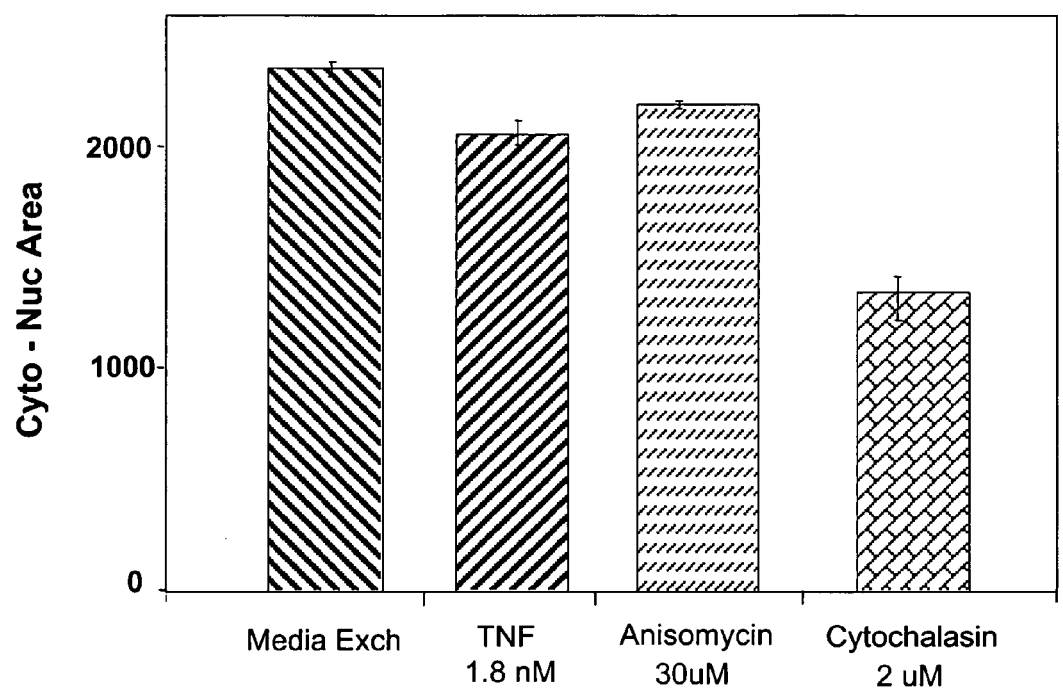
FIG. 49 is a bar graph showing quantitative results for the proportion of phosphorylated p38 MAPK in the nucleus versus the cytoplasm for wells treated by medium exchange (negative control), TNF α (1.8 nM), Anisomycin (30 μM), and Cytochalasin D (2 μM) after exposure of Swiss 3T3 cells for 45 min. The dominant response is obtained for Anisomycin. Mean+/−SEM n=1500 cells totaled across 16 wells.

Cell area for cells treated with the toxin analogs was as shown in FIG. 49. The dominant response was obtained for cytochalasin D.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

We claim:

1. An automated method for cell based toxin detection and organ localization comprising providing an array of locations containing cells to be treated with a test substance, wherein the array comprises at least a first cell type and a second cell type, and wherein the first cell type and the second cell type are not contained on the same location in the array; wherein the first and second cell types are derived from different organ types; wherein each of the cell types comprises at least one luminescent reporter molecule; wherein the localization, distribution, structure, or activity of the at least one luminescent reporter molecule is altered by a toxin to be detected;

contacting the at least first cell type and second cell type with the test substance either before or after possession of the at least one luminescent reporter molecules by the first cell type and the second cell type;

imaging or scanning multiple cells in each of the locations containing the first cell type or the second cell type to obtain luminescent signals from the luminescent reporter molecule in the first cell type and the second cell type;

converting the luminescent signals into digital data;

utilizing the digital data to automatically measure the localization, distribution, structure or activity of the at least one luminescent reporter molecule on or in the first cell type and the second cell type, wherein a change in the localization, distribution, structure or activity of the luminescent reporter molecule indicates the presence of a toxin and an organ localization of the toxin.

2. The method of claim 1, wherein the array further comprises a third cell type, wherein the first, second, and third cell types are not contained on the same location in the array; and wherein the first, second, and third cell types are derived from different organ types.

3. The method of claim 1 or 2 wherein one or more of the cell types further comprises at least a second luminescent reporter molecule; wherein the localization, distribution, structure, or activity of the second luminescent reporter molecule is altered by a toxin to be detected.

4. The method of claim 3, wherein one or more of the cell types further comprises at least a third luminescent reporter molecule; wherein the localization, distribution, structure, or activity of the third luminescent reporter molecule is altered by a toxin to be detected.

5. The method of claim 1, wherein the at least first cell type and the at least second cell type further comprise at least a second luminescent reporter molecule; wherein the localization, distribution, structure, or activity of the at least second luminescent reporter molecule is altered by a toxin to be detected.

6. The method of claim 5, wherein the at least one luminescent reporter molecule is a detector, wherein the detector detects a toxin present in the test substance; and the second luminescent reporter molecule is selected from the group consisting of a classifier or an identifier, wherein the classifier detects a toxin present in the test substance and identifies a cell pathway affected by a toxin present in the test substance, and the identifier detects the presence of a toxin present in the test substance and identifies a specific toxin or group of toxins present in the test substance.

7. The method of claim 6, wherein the second luminescent reporter is a classifier, and the digital data derived from the classifier is used to select an identifier for identification of the specific toxin or group of toxins.

* * * * *